United States Patent
Travers et al.

(10) Patent No.: US 12,378,586 B2
(45) Date of Patent: *Aug. 5, 2025

(54) SYSTEMS, METHODS, AND COMPOSITIONS FOR THE GLYCOSYLATION OF CANNABINOID COMPOUNDS

(71) Applicant: Trait Biosciences, Inc., Los Alamos, NM (US)

(72) Inventors: Timothy Travers, Los Alamos, NM (US); Erick LeBrun, Los Alamos, NM (US)

(73) Assignee: Trait Biosciences, Inc., Los Alamos, NM (US)

( * ) Notice: Subject to any disclaimer, the term of this patent is extended or adjusted under 35 U.S.C. 154(b) by 84 days.

This patent is subject to a terminal disclaimer.

(21) Appl. No.: 17/905,047

(22) PCT Filed: Feb. 26, 2021

(86) PCT No.: PCT/US2021/020040
§ 371 (c)(1),
(2) Date: Aug. 25, 2022

(87) PCT Pub. No.: WO2021/174092
PCT Pub. Date: Sep. 2, 2021

(65) Prior Publication Data
US 2023/0212625 A1   Jul. 6, 2023

Related U.S. Application Data

(60) Provisional application No. 62/983,019, filed on Feb. 28, 2020.

(51) Int. Cl.
*C12N 9/10* (2006.01)
*A61K 31/00* (2006.01)
*A61K 31/7034* (2006.01)
*C12P 17/06* (2006.01)

(52) U.S. Cl.
CPC ............ *C12P 17/06* (2013.01); *C12N 9/1051* (2013.01); *C12Y 204/01035* (2013.01)

(58) Field of Classification Search
None
See application file for complete search history.

(56) References Cited

U.S. PATENT DOCUMENTS

| 2008/0267966 A1 | 10/2008 | Masignani et al. |
| 2010/0011456 A1 | 1/2010 | Mathur et al. |
| 2019/0085347 A1* | 3/2019 | Sayre ............... C12N 9/0065 |
| 2019/0153460 A1 | 5/2019 | Sayre et al. |
| 2021/0071209 A1* | 3/2021 | Anderson ............... C12N 9/88 |

OTHER PUBLICATIONS

Hardman et al, 2017, bioRxiv, Cannabinoid glycosides: In vitro Production of a New Class of Cannabinoids with Improved Physiochemical Properties, p. 1-37.*
Madhav et al, 2013, Plant Physiology and Biochemistry, 63:245-253.*
Aizpurua-Olaizola et al, 2016, J. Nat. Prod., 79:324-331.*
Gertsch et al, 2010, British Journal of Pharmacology, 160:523-529.*
Sirikantaramas et al, *Cannabis sativa* L.—Botany and Biotechnology, 2017, section 8.*
Morimoto et al, 2007, The Journal of Biological Chemistry, 282:20739-20751.*
Peč et al, 2010, Biotechnol Lett, 32:935-941.*
Flores-Sanchez et al, 2009, Journal of Biotechnology, 143:157-168.*
Wrobel et al, 2018, Biotechnol Lett, 40:445-454.*
Cerdeno-Tarraga et al (2005, Science, 307:1463-1465.*
Sobhanifar et al. Structure and Mechanism of *Staphylococcus aureus* Tars, the Wall Teichoic Acid beta-glycosyltransferase Involved in Methicillin Resistance. PLoS Pathogens. Dec. 14, 2016, vol. 12, No. 12, e1006067; especially abstract; p. 18, para 1-2.
International Search Report and Written Opinion dated Jul. 22, 2021 in International Application No. PCT/US2021/020040, 22 pages.
Janee'. Hardman et al: "Cannabinoid glycosides: In vitro production of a new class of cannabinoids with improved physicochemical properties", BIORXIV, [Online] Jan. 30, 2017 (Jan. 30, 2017), XP055564615, DOI: 10.1101/104349 Retrieved from the Internet: URL:https://www.biorxiv.org/content/biorxiv/early/2017/01/30/104349.full.pdf&[retrieved on Jan. 29, 2024] * p. 3, paragraph 4-p. 7, paragraph 1; figure S5 *.
Muedlmmad Tayyab Akhtar et al: "Hydroxylation and glycosylation of [Delta] 9-tetrahydrocannabinol by Catharanthus roseus cell suspension culture", Biocatalysis and Biotransformation., vol. 33, No. 5-6, Feb. 29, 2016 (Feb. 29, 2016), pp. 279-286, XP055560191, GB ISSN: 1024-2422, DOI: 10.3109/10242422.2016.1151006 * p. 282, right-hand column, paragraph 1-p. 285, left-hand column, paragraph 1; figure 2 *.
Harish Madhav et al: Functional and structural variation of uridine diphosphate glycosyltransferase (UGT) gene of Stevia rebaudiana-UGTSr involved in the synthesis of rebaudioside Arr Plant Physiology and Biochemistry, vol. 63, Dec. 17, 2012 (Dec. 17, 2012), pp. 245-253, XP055111642, ISSN: 0981-9428, DOI: 10.1016/j.plaphy.2012.11.029 * the whole document *.
De Bruyn Frederik et al: Biotechnological advances in UDP-sugar based glycosylation of small moleculesrr Biotechnology Advances., vol. 33, No. 2, Feb. 16, 2015 (Feb. 16, 2015), pp. 288-302, XP093124872, GB ISSN: 0734-9750, DOI: 10.1016/j.biotechadv.2015.02.005 * the whole document *.

(Continued)

*Primary Examiner* — Jason Deveau Rosen
(74) *Attorney, Agent, or Firm* — Berg Hill Greenleaf Ruscitti LLP.

(57) ABSTRACT

The present invention relates generally to the identification novel UDP-glucosyltransferases enzymes having specific activity towards cannabinoid compounds. The present invention further relates generally to the use of novel UGT enzymes having specific activity towards cannabinoid compounds to generate water-soluble cannabinoid glycoside compounds.

4 Claims, 14 Drawing Sheets
Specification includes a Sequence Listing.

(56) References Cited

OTHER PUBLICATIONS

Supplementary European Search Report dated Jan. 30, 2024, 11 pages.

* cited by examiner

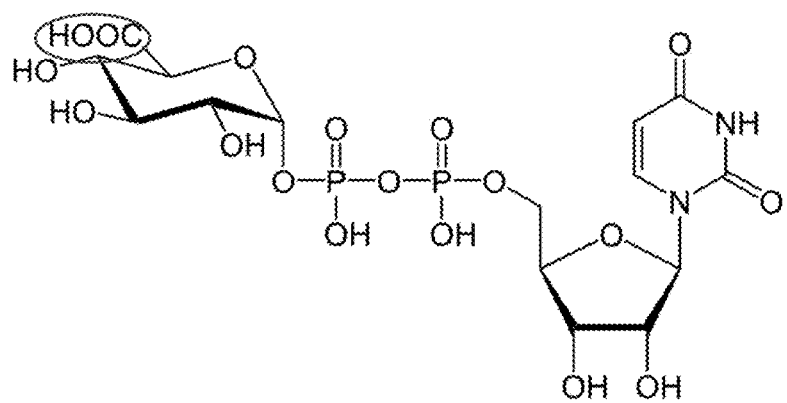
UDP- Glucuronic Acid
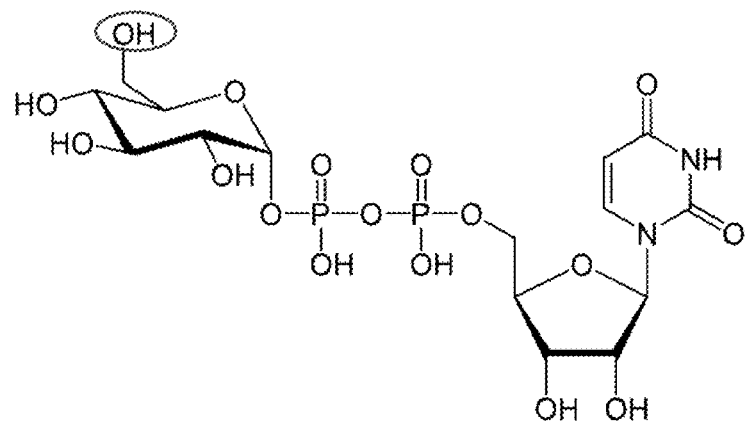
UDP-Glucose
FIG. 12

SYSTEMS, METHODS, AND COMPOSITIONS FOR THE GLYCOSYLATION OF CANNABINOID COMPOUNDS

CROSS-REFERENCE TO RELATED APPLICATION

This application is a national stage application under 35 U.S.C. 371 of PCT Application No. PCT/US2021/020040 having an international filing date of Feb. 26, 2021, which designated the United States, which PCT application claimed the benefit of U.S. Application Ser. No. 62/983,019, filed Feb. 28, 2020, both of which are incorporated by reference in their entirety.

SEQUENCE LISTING

The instant application contains contents of the electronic sequence listing (90425-00322-Sequence-Listing.xml; Size: 13,966,724 bytes; and Date of Creation: Aug. 25, 2022) is herein incorporated by reference in its entirety.

TECHNICAL FIELD

The present invention relates generally to the identification novel UDP-glucosyltransferases enzymes having specific activity towards cannabinoid compounds. The present invention further relates generally to the use of novel UGT enzymes having specific activity towards cannabinoid compounds to generate water-soluble cannabinoid glycoside compounds.

BACKGROUND

Cannabinoids are a class of specialized compounds synthesized by *Cannabis*. They are formed by condensation of terpene and phenol precursors. They include these more abundant forms: 49-tetrahydrocannabinol (THC), cannabidiol (CBD), cannabichromene (CBC), and cannabigerol (CBG). Another cannabinoid, cannabinol (CBN), is formed from THC as a degradation product and can be detected in some plant strains. Typically, THC, CBD, CBC, and CBG occur together in different ratios in the various plant strains. These cannabinoids are generally lipophilic, nitrogen-free, mostly phenolic compounds and are derived biogenetically from a monoterpene and phenol, the acid cannabinoids from a monoterpene and phenol carboxylic acid and have a C21 base. Cannabinoids also find their corresponding carboxylic acids in plant products. In general, the carboxylic acids have the function of a biosynthetic precursor. For example, the tetrahydrocannabinols $\Delta^9$- and $\Delta^8$-THC arise in vivo from the THC carboxylic acids by decarboxylation and likewise, CBD from the associated cannabidiolic acid.

Importantly, cannabinoids are hydrophobic small molecules and, as a result, are highly insoluble. Due to this insolubility, cannabinoids such as THC and CBD may need to be efficiently solubilized to facilitate transport, storage, and adsorption through certain tissues and organs. For example, the metabolism of cannabinoids in the human body goes through the classic two-phases detoxification process of oxidation followed by glucuronidation-which is a form of glycosylation involving the addition of a sugar from UDP-Glucuronic Acid to a cannabinoid. As shown below, the chemical structures of UDP-glucuronic acid and UDP-glucose are similar. As described in, U.S. Pat. No. 8,410,064 by Pandya et al., cannabinoids may be subject to cytochrome P450 oxidation and subsequent UDP-glucuronosyltransferase dependent glucuronidation in the body after consumption. (see FIG. 12) The resulting glucuronide of the oxidized cannabinoids is the main metabolite found in urine, and thus, this solubilization process plays a critical role in the metabolic clearance of cannabinoids. In another embodiment outlined in PCT/US18/24409 and PCT/US18/41710 (both of which are incorporated herein in their entirety by reference, including examples 1-19, and all specific materials and method), by Sayre et al., cannabinoids may be glycosylated to form water-soluble glycoside compounds. In preferred embodiment, such water-soluble cannabinoid glycoside may include one or more sugar moieties, and preferably 1-3 sugar moieties, also referred to a glycosylation sites.

One area where water-soluble cannabinoids has seen renewed interest is in the fields of cannabinoid-infused consumer products. However, the ability to effectively solubilize cannabinoids has limited their applicability. To overcome these limitations, many manufacturers of cannabinoid-infused products have adopted the use of traditional pharmaceutical delivery methods of using nanoemulsions of cannabinoids. This nanoemulsion process essentially coats the cannabinoid in a hydrophilic compound, such as oil or other similar compositions. However, the use of nanoemulsions is limited both technically, and from a safety perspective:

First, a large number of surfactants and cosurfactants are required for nanoemulsion stabilization. Moreover, the stability of nanoemulsions is inherently unstable, and may be disturbed by slight fluctuations in temperature and pH and is further subject to the "oswald ripening effect" or ORE. ORE describes the process whereby molecules on the surface of particles are more energetically unstable than those within. Therefore, the unstable surface molecules often go into solution shrinking the particle over time and increasing the number of free molecules in solution. When the solution is supersaturated with the molecules of the shrinking particles, those free molecules will redeposit on the larger particles. Thus, small particles decrease in size until they disappear, and large particles grow even larger. This shrinking and growing of particles will result in a larger mean diameter of a particle size distribution (PSD). Over time, this causes emulsion instability and eventually phase separation.

Second, nanoemulsions may not be safe for human consumption. For example, nanoemulsions were first developed as a method to deliver small quantities of pharmaceutical compounds having poor solubility. However, the ability to "hide" a compound, such as a cannabinoid, in a nanoemulsion may allow the cannabinoid to be delivered to parts of the body where it was previously prevented from entering, as well as accumulating in tissues and organs where cannabinoids and nanoparticles would not typically be found. Additionally, such nanoemulsions, as well as other water-compatible strategies, do not address one of the major-shortcomings of cannabinoid-infused commercial consumables, namely the strong unpleasant smell and taste. Moreover, such water-compatible strategies deliver inconsistent and delayed cannabinoid uptake in the body which may result in consumers ingesting a higher dose of cannabinoid-infused product than is recommended, as well as delayed, inconsistent, and unpredictable medical and/or psychotropic experiences. As will be discussed in more detail below, the current inventive technology overcomes the limitations of traditional cannabinoid emulsion systems while meeting the objectives of a truly effective and scalable cannabinoid production, solubilization, and isolation system.

SUMMARY OF THE INVENTION

One aspect of the present invention relates generally to the identification novel UDP-glucosyltransferases (UDP-UGTs or UGTs) enzymes having glycosylation activity towards one or more cannabinoid compounds. In one preferred aspect, the present invention includes the identification of novel UGTs according to the amino acid sequences identified as SEQ ID NOs. 1-9181, and UGTs having 90% sequence identity with SEQ ID NOs. 1-9181, that have glycosylation activity towards one or more cannabinoid compounds, and preferably THC and CBD.

One aspect of the present invention further relates generally to the use of novel UGT enzymes having specific activity towards one or more cannabinoid compounds to generate water-soluble cannabinoid glycoside compounds in in vitro, ex vivo, and in vivo systems. In one preferred aspect, the present invention use of novel UGT enzymes according to the amino acid sequences identified as SEQ ID NOs. 1-9181, and UGTs having 90% sequence identity with SEQ ID NOs. 1-9181, that have glycosylation activity towards one or more cannabinoid compounds, and preferably THC and CBD, in in vitro, ex vivo, and in vivo systems. In one preferred aspect of the invention, an in vivo system may include a whole organism system, such as a plant, or cell culture, such as a plant cell culture, an algal cell culture, a fungi cell culture, or a microorganism cell culture, such as a bacterial or yeast cell culture.

One aspect of the present invention further relates generally to novel methods of generating water-soluble cannabinoid glycoside compounds, and preferably THC-glycosides and CBD-glycosides, comprising the step of introducing one or more cannabinoids to a UGT enzyme having specific activity towards one or more cannabinoid compounds according to the amino acid sequences identified as SEQ ID NOs. 1-9181, and UGTs having 90% sequence identity with SEQ ID NOs. 1-9181, that have glycosylation activity towards one or more cannabinoid compounds, in in vitro, ex vivo, and in vivo systems. In one preferred aspect of the invention, an in vivo system may include a whole organism system, such as a plant, or cell culture, such as a plant cell culture, an algal cell culture, a fungi cell culture, or a microorganism cell culture, such as a bacterial or yeast cell culture. In other embodiments, an ex vivo system may include a bioreactor system. In other aspects, an in vitro system may include chemical conversion of cannabinoids into water-soluble cannabinoid glycoside compounds.

Yet, another aspect of the current inventive technology may include the generation of genetically modified organisms configured to produce water-soluble cannabinoid glycoside compounds. In one preferred aspect, a plant, a plant cell, an algal cell, a fungi, a bacteria, or a yeast cell, may be genetically modified to express a nucleotide sequence encoding one or more UGTs that have glycosylation activity towards one or more cannabinoid compounds, and preferably a UGT selected from the group of nucleotide sequences consisting of: a nucleotide sequence encoding an amino acid sequence according to SEQ ID NOs. 1-9181, and a nucleotide sequence encoding an amino acid sequence having 90% sequence identity with SEQ ID NOs. 1-9181.

Another aspect of the current inventive technology includes the isolated amino acid sequences encoding one or more UGTs that have glycosylation activity towards one or more cannabinoid compounds according to SEQ ID NOs. 1-9181, and amino acid sequence having 90% sequence identity with SEQ ID NOs. 1-9181.

Another aspect of the current inventive technology includes a nucleotide sequence encoding one or more UGTs that have glycosylation activity towards one or more cannabinoid compounds according to SEQ ID NOs. 1-9181, and a nucleotide sequence encoding an amino acid sequence having 90% sequence identity with SEQ ID NOs. 1-9181.

Another aspect of the current inventive technology includes an expression vector having a nucleotide sequence encoding one or more UGTs that have glycosylation activity towards one or more cannabinoid compounds according to SEQ ID NOs. 1-9181, and a nucleotide sequence encoding an amino acid sequence having 90% sequence identity with SEQ ID NOs. 1-9181, operably linked to a promoter.

Another aspect of the current inventive technology includes one or more organisms, such as a plant, plant cell, bacteria, algae, fungi, or yeast cell, transformed by an expression vector having a nucleotide sequence encoding one or more UGTs that have glycosylation activity towards one or more cannabinoid compounds according to SEQ ID NOs. 1-9181, and a nucleotide sequence encoding an amino acid sequence having 90% sequence identity with SEQ ID NOs. 1-9181, operably linked to a promoter.

One aspect of the present invention further relates generally to novel methods of generating water-soluble cannabinoid glycoside compounds, and preferably THC-glycosides and CBD-glycosides, comprising the step of introducing one or more cannabinoids to a UGT enzyme having specific activity towards one or more cannabinoid compounds according to the amino acid sequences identified as belonging to the Gram+of class of UGTs as described herein, in an in vitro, ex vivo, and in vivo systems. In this preferred embodiment, the Gram+of class of UGTs may include the following structural groups: 5tzk (SEQ ID NOs. 1-1182), 3bcv (SEQ ID NOS. 1183-1222), 5hea (SEQ ID NOs. 1223-1805), 6h21 (SEQ ID NOs. 1806-1825), and UGTs having 90% sequence identity with SEQ ID NOs. 1-1825, that have glycosylation activity towards one or more cannabinoid compounds. In one preferred aspect of the invention, an in vivo system may include a whole organism system, such as a plant, or cell culture, such as a plant cell culture, an algal cell culture, a fungi cell culture, or a microorganism cell culture, such as a bacterial or yeast cell culture. In other embodiments, an ex vivo system may include a bioreactor system. In other aspects, an in vitro system may include chemical conversion of cannabinoids into water-soluble cannabinoid glycoside compounds.

In another aspect, one or more of cannabinoid glycoside compounds identified as: 10B, 10C, 10D, 11A, 11B, 11C, 11D, 11E and 11F, may be generated through the step of introducing one or more cannabinoids to a UGT enzyme having specific activity towards one or more cannabinoid compounds according to the amino acid sequences identified as belonging to the Gram+of class of UGTs as described herein, in an in vitro, ex vivo, and in vivo systems. In this preferred embodiment, the Gram+of class of UGTs may include the following structural groups: 5tzk (SEQ ID NOs. 1-1182), 3bcv (SEQ ID NOs. 1183-1222), 5hea (SEQ ID NOs. 1223-1805), 6h21 (SEQ ID NOs. 1806-1825), and UGTs having 90% sequence identity with SEQ ID NOs. 1-1825, that have glycosylation activity towards one or more cannabinoid compounds.

Yet, another aspect of the current inventive technology may include the generation of genetically modified organisms configured to produce water-soluble cannabinoid glycoside compounds. In one preferred aspect, a plant, a plant cell, an algal cell, a fungi, a bacteria, or a yeast cell, may be genetically modified to express a nucleotide sequence encoding one or more Gram+class of UGTs that have glycosylation activity towards one or more cannabinoid compounds, and preferably a UGT selected from the group of nucleotide sequences consisting of: a nucleotide sequence encoding an amino acid sequence according to SEQ ID NOs. 1-1825, and a nucleotide sequence encoding an amino acid sequence having 90% sequence identity with SEQ ID NOs. 1-1825.

Another aspect of the current inventive technology includes the isolated amino acid sequences encoding one or more Gram+class of UGTs that have glycosylation activity towards one or more cannabinoid compounds according to SEQ ID NOs. 1-1825, and amino acid sequence having 90% sequence identity with SEQ ID NOs. 1-1825.

Another aspect of the current inventive technology includes a nucleotide sequence encoding one or more Gram+class of UGTs that have glycosylation activity towards one or more cannabinoid compounds according to SEQ ID NOs. 1-1825, and a nucleotide sequence encoding an amino acid sequence having 90% sequence identity with SEQ ID NOs. 1-1825.

Another aspect of the current inventive technology includes an expression vector having a nucleotide sequence encoding one or more Gram+class of UGTs that have glycosylation activity towards one or more cannabinoid compounds according to SEQ ID NOs. 1-9181, and a nucleotide sequence encoding an amino acid sequence having 90% sequence identity with SEQ ID NOs. 1-1825, operably linked to a promoter.

Another aspect of the current inventive technology includes one or more organisms, such as a plant, plant cell, bacteria, algae, fungi, or yeast cell, transformed by an expression vector having a nucleotide sequence encoding one or more Gram+class of UGTs that have glycosylation activity towards one or more cannabinoid compounds according to SEQ ID NOs. 1-1825, and a nucleotide sequence encoding an amino acid sequence having 90% sequence identity with SEQ ID NOs. 1-1825, operably linked to a promoter.

One aspect of the present invention further relates generally to novel methods of generating water-soluble cannabinoid glycoside compounds, and preferably THC-glycosides and CBD-glycosides, comprising the step of introducing one or more cannabinoids to a UGT enzyme having specific activity towards one or more cannabinoid compounds according to the amino acid sequences identified as belonging to the GT-A of class of UGTs as described herein, in an in vitro, ex vivo, and in vivo systems. In this preferred embodiment, the GT-A of class of UGTs may include the following structural groups: 1g9r (SEQ ID NOs. 1826-1828), 2286 (SEQ ID NOs. 1829-1985), 3ckj (SEQ ID NOs. 1986-2453), 3e25 (SEQ ID NOs. 2454-3126), 3fly (SEQ ID NOs. 3127-3430), 4dec (SEQ ID NOs. 3431-3481), 5mlz (SEQ ID NOs. 3482-3639), 5nv4 (SEQ ID NOs. 3640-3693), 6fsn (SEQ ID NOs. 3694-4699), 6p61 (SEQ ID NOs. 4700-5259) and UGTs having 90% sequence identity with SEQ ID NOs. 1826-5259, that have glycosylation activity towards one or more cannabinoid compounds. In one preferred aspect of the invention, an in vivo system may include a whole organism system, such as a plant, or cell culture, such as a plant cell culture, an algal cell culture, a fungi cell culture, or a microorganism cell culture, such as a bacterial or yeast cell culture. In other embodiments, an ex vivo system may include a bioreactor system. In other aspects, an in vitro system may include chemical conversion of cannabinoids into water-soluble cannabinoid glycoside compounds.

In another aspect, one or more of cannabinoid glycoside compounds identified as: 10B, 10C, 10D, 11A, 11B, 11C, 11D, 11E and 11F, may be generated through the step of introducing one or more cannabinoids to a UGT enzyme having specific activity towards one or more cannabinoid compounds according to the amino acid sequences identified as belonging to the Gram+of class of UGTs as described herein, in an in vitro, ex vivo, and in vivo systems. In this preferred embodiment, the GT-A of class of UGTs may include the following structural groups: 1 g9r (SEQ ID NOs. 1826-1828), 2286 (SEQ ID NOs. 1829-1985), 3ckj (SEQ ID NOs. 1986-2453), 3c25 (SEQ ID NOs. 2454-3126), 3fly (SEQ ID NOs. 3127-3430), 4dec (SEQ ID NOs. 3431-3481), 5mlz (SEQ ID NOs. 3482-3639), 5nv4 (SEQ ID NOs. 3640-3693), 6fsn (SEQ ID NOs. 3694-4699), 6p61 (SEQ ID NOs. 4700-5259) and UGTs having 90% sequence identity with SEQ ID NOs. 1826-5259, that have glycosylation activity towards one or more cannabinoid compounds.

Yet, another aspect of the current inventive technology may include the generation of genetically modified organisms configured to produce water-soluble cannabinoid glycoside compounds. In one preferred aspect, a plant, a plant cell, an algal cell, a fungi, a bacteria, or a yeast cell, may be genetically modified to express a nucleotide sequence encoding one or more GT-A class of UGTs that have glycosylation activity towards one or more cannabinoid compounds, and preferably a UGT selected from the group of nucleotide sequences consisting of: a nucleotide sequence encoding an amino acid sequence according to SEQ ID NOs. 1826-5259, and a nucleotide sequence encoding an amino acid sequence having 90% sequence identity with SEQ ID NOs. 1826-5259.

Another aspect of the current inventive technology includes the isolated amino acid sequences encoding one or more GT-A class of UGTs that have glycosylation activity towards one or more cannabinoid compounds according to SEQ ID NOs. 1826-5259, and amino acid sequence having 90% sequence identity with SEQ ID NOs. 1826-5259.

Another aspect of the current inventive technology includes a nucleotide sequence encoding one or more GT-A class of UGTs that have glycosylation activity towards one or more cannabinoid compounds according to SEQ ID NOs. 1826-5259, and a nucleotide sequence encoding an amino acid sequence having 90% sequence identity with SEQ ID NOs. 1826-5259.

Another aspect of the current inventive technology includes an expression vector having a nucleotide sequence encoding one or more GT-A class of UGTs that have glycosylation activity towards one or more cannabinoid compounds according to SEQ ID NOs. 1826-5259, and a nucleotide sequence encoding an amino acid sequence having 90% sequence identity with SEQ ID NOs. 1826-5259, operably linked to a promoter.

Another aspect of the current inventive technology includes one or more organisms, such as a plant, plant cell, bacteria, algae, fungi, or yeast cell, transformed by an expression vector having a nucleotide sequence encoding one or more GT-A class of UGTs that have glycosylation activity towards one or more cannabinoid compounds according to SEQ ID NOs. 1826-5259, and a nucleotide sequence encoding an amino acid sequence having 90% sequence identity with SEQ ID NOs. 1826-5259, operably linked to a promoter.

One aspect of the present invention further relates generally to novel methods of generating water-soluble cannabinoid glycoside compounds, and preferably THC-glycosides and CBD-glycosides, comprising the step of introducing one or more cannabinoids to a UGT enzyme having specific activity towards one or more cannabinoid compounds according to the amino acid sequences identified as belonging to the GT-B of class of UGTs as described herein, in an in vitro, ex vivo, and in vivo systems. In this preferred embodiment, the GT-B of class of UGTs may include the following structural groups: 2acv (SEQ ID NOs. 5260-6290), 2iya (SEQ ID NOs. 6290-6953), 3hbf (SEQ ID NOs. 6954-7484), 5g15 (SEQ ID NOs. 7485-7998), 3c48 (SEQ ID NOs. 7999-8243), 5nlm (SEQ ID NOs. 8244-8486), 5du2 (SEQ ID NOs. 8487-8612), 2clx (SEQ ID NOS. 8613-8688), 5zfk (SEQ ID NOs. 8689-8758), 4rel (SEQ ID NOs. 8759-8816), 3otg (SEQ ID NOs. 8817-8873), 5v2j (SEQ ID NOs. 8874-8921), 2r60 (SEQ ID NOs. 8922-8965), 4amg (SEQ ID NOs. 8966-9007), 4n9w (SEQ ID NOs. 9008-9046), 2pq6 (SEQ ID NOs. 9047-9082), 4wyi (SEQ ID NOs. 9083-9111), 6bk0 (SEQ ID NOs. 9112-9133), 6inf (SEQ ID NOs. 9134-9149), 3ia7 (SEQ ID NOs. 9150-9158), 5d01 (SEQ ID NOs. 9159-9165), 6ij9 (SEQ ID NOs. 9166-9170), 6d9t (SEQ ID NOs. 9171-9175), 2jjm (SEQ ID NOs. 9176-9180), 3mbo (SEQ ID NO. 9181) and UGTs having 90% sequence identity with SEQ ID NOs. 5260-9181, that have glycosylation activity towards one or more cannabinoid compounds. In one preferred aspect of the invention, an in vivo system may include a whole organism system, such as a plant, or cell culture, such as a plant cell culture, an algal cell culture, a fungi cell culture, or a microorganism cell culture, such as a bacterial or yeast cell culture. In other embodiments, an ex vivo system may include a bioreactor system. In other aspects, an in vitro system may include chemical conversion of cannabinoids into water-soluble cannabinoid glycoside compounds.

In another aspect, one or more of cannabinoid glycoside compounds identified as: 10B, 10C, 10D, 11A, 11B, 11C, 11D, 11E and 11F, may be generated through the step of introducing one or more cannabinoids to a UGT enzyme having specific activity towards one or more cannabinoid compounds according to the amino acid sequences identified as belonging to the Gram+of class of UGTs as described herein, in an in vitro, ex vivo, and in vivo systems. In this preferred embodiment, the GT-B of class of UGTs may include the following structural groups: 2acv (SEQ ID NOs. 5260-6290), 2iya (SEQ ID NOs. 6290-6953), 3hbf (SEQ ID NOs. 6954-7484), 5g15 (SEQ ID NOs. 7485-7998), 3c48 (SEQ ID NOs. 7999-8243), 5nlm (SEQ ID NOs. 8244-8486), 5du2 (SEQ ID NOs. 8487-8612), 2clx (SEQ ID NOs. 8613-8688), 5zfk (SEQ ID NOS. 8689-8758), 4rel (SEQ ID NOs. 8759-8816), 3otg (SEQ ID NOs. 8817-8873), 5v2j (SEQ ID NOS. 8874-8921), 2r60 (SEQ ID NOs. 8922-8965), 4amg (SEQ ID NOs. 8966-9007), 4n9w (SEQ ID NOs. 9008-9046), 2pq6 (SEQ ID NOs. 9047-9082), 4wyi (SEQ ID NOs. 9083-9111), 6bk0 (SEQ ID NOs. 9112-9133), 6inf (SEQ ID NOs. 9134-9149), 3ia7 (SEQ ID NOs. 9150-9158), 5d01 (SEQ ID NOs. 9159-9165), 6ij9 (SEQ ID NOs. 9166-9170), 6d9t (SEQ ID NOs. 9171-9175), 2jjm (SEQ ID NOs. 9176-9180), 3mbo (SEQ ID NO. 9181) and UGTs having 90% sequence identity with SEQ ID NOs. 5260-9181, that have glycosylation activity towards one or more cannabinoid compounds.

Yet, another aspect of the current inventive technology may include the generation of genetically modified organisms configured to produce water-soluble cannabinoid glycoside compounds. In one preferred aspect, a plant, a plant cell, an algal cell, a fungi, a bacteria, or a yeast cell, may be genetically modified to express a nucleotide sequence encoding one or more GT-B class of UGTs that have glycosylation activity towards one or more cannabinoid compounds, and preferably a GT-B class of UGT selected from the group of nucleotide sequences consisting of: a nucleotide sequence encoding an amino acid sequence according to SEQ ID NOs. 5260-9181, and a nucleotide sequence encoding an amino acid sequence having 90% sequence identity with SEQ ID NOs. 1-9181.

Another aspect of the current inventive technology includes the isolated amino acid sequences encoding one or more GT-B class of UGTs that have glycosylation activity towards one or more cannabinoid compounds according to SEQ ID NOs. 5260-9181, and amino acid sequence having 90% sequence identity with SEQ ID NOs. 5260-9181.

Another aspect of the current inventive technology includes a nucleotide sequence encoding one or more GT-B class of UGTs that have glycosylation activity towards one or more cannabinoid compounds according to SEQ ID NOs. 5260-9181, and a nucleotide sequence encoding an amino acid sequence having 90% sequence identity with SEQ ID NOs. 5260-9181.

Another aspect of the current inventive technology includes an expression vector having a nucleotide sequence encoding one or more GT-B class of UGTs that have glycosylation activity towards one or more cannabinoid compounds according to SEQ ID NOs. 1-9181, and a nucleotide sequence encoding an amino acid sequence having 90% sequence identity with SEQ ID NOs. 5260-9181, operably linked to a promoter.

Another aspect of the current inventive technology includes one or more organisms, such as a plant, plant cell, bacteria, algae, fungi, or yeast cell, transformed by an expression vector having a nucleotide sequence encoding one or more GT-B class of UGTs that have glycosylation activity towards one or more cannabinoid compounds according to SEQ ID NOs. 5260-9181, and a nucleotide sequence encoding an amino acid sequence having 90% sequence identity with SEQ ID NOs. 5260-9181, operably linked to a promoter.

One aspect of the current inventive technology includes improved systems and methods for the bioconversion of cannabinoid compounds into water-soluble cannabinoid glycosides, or water-soluble acetyl cannabinoid glycosides in a bacterial, yeast, or plant cell culture system. In another preferred aspect, a preferred plant cell culture system may include a *Cannabis* suspension cell culture, or a tobacco plant cell culture.

Another aspect of the current inventive technology includes one or more consumer products, or pharmaceutical preparations having at least one cannabinoid glycoside generated in an in vitro, ex vivo, or in vivo system by the action of one or more UGTs that have glycosylation activity towards one or more cannabinoid compounds according to SEQ ID NOs. 1-9181, and a nucleotide sequence encoding an amino acid sequence having 90% sequence identity with SEQ ID NOs. 1-9181.

Additional aspects of the current invention may include one or more of the following preferred embodiments:
1. A method of generating a water-soluble cannabinoid comprising the steps:
   establishing a suspension cell culture of genetically modified yeast cells that express a nucleotide sequence encoding a heterologous UDP-glucosyltransferases (UGT) having glycosylation activity towards one or more cannabinoid compounds operably linked to a promotor, wherein said heterologous UGT comprises a heterologous UGT selected from the group of amino acid sequences consisting of: SEQ ID NOs. 1-9181, and a nucleotide sequence encoding an amino acid sequence having 90% sequence identity with SEQ ID NOs. 1-9181;

introducing at least one cannabinoid to said suspension cell culture of genetically modified yeast cells; and glycosylating the cannabinoid through the action of said heterologous UGT forming a water-soluble cannabinoid glycoside.

2. The method of embodiment 1, wherein said genetically modified yeast cells comprise genetically modified yeast cells selected from the group consisting of: genetically modified *Pichia pastoris* cells, genetically modified *Saccharomyces cerevisiae* cells, and genetically modified *Kluyveromyces marxianus* cells.

3. The method of embodiment 1, wherein said step of introducing at least one cannabinoid to said suspension cell culture of genetically modified yeast cells comprises the step of introducing at least one cannabinoid to the suspension cell culture selected from the group consisting of: cannabidiol (CBD), cannabidiolic acid (CBDA), delta-9-tetrahydrocannabinol (THC), and tetrahydrocannabinolic acid (THCA).

4. The method of embodiment 2, wherein said CBD or said CBDA are glycosylated to form a 2×CBD Glycoside, and a 2×CBDA Glycoside respectively.

5. The method of embodiment 1, wherein said step of introducing comprises the step of introducing selected from the group consisting of: introducing a cannabinoid extract containing a spectrum of cannabinoids to said suspension cell culture of genetically modified yeast cells, introducing one or more non-psychoactive cannabinoids to said suspension cell culture of genetically modified yeast cells, introducing one or more cannabinoid precursors to said suspension cell culture of genetically modified yeast cells, and introducing one or more cannabinoid acids to said suspension cell culture of genetically modified yeast cells.

6. The method of embodiment 1, and further comprising isolating said water-soluble cannabinoid glycoside.

7. The method of embodiments 1 and 6, wherein said isolated water-soluble cannabinoid glycoside comprises the compound 10C:

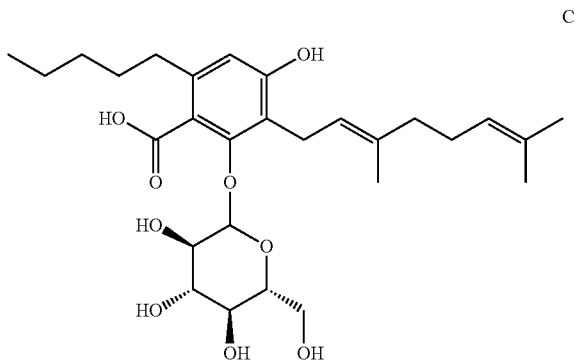 [SMILES: CCCCCc1cc(O)c(C/C=C(\C)CCC=C(C)C)c(OC2O[C@H](CO)[C@@H](O)[C@H](O)[C@H]2O)c1C(=O)O]

and/or a pharmaceutically acceptable salt.

8. The method of embodiments 1 and 6, wherein said isolated water-soluble cannabinoid glycoside comprises the compound 10D:

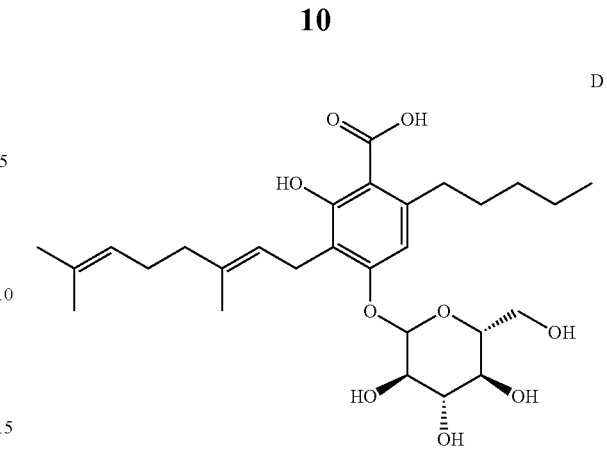

and/or a pharmaceutically acceptable salt.

9. The method of embodiments 1 and 6, wherein said isolated water-soluble cannabinoid glycoside comprises the compound 11B:

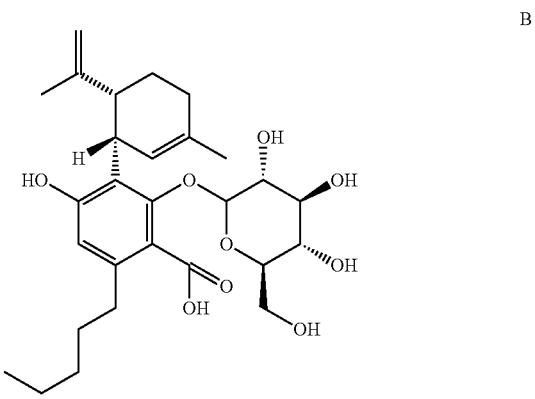 [SMILES: C=C(C)[C@@H]1CCC(C)=C[C@@H]1c1c(O)cc(CCCCC)c(C(=O)O)c1OC1O[C@H](CO)[C@@H](O)[C@H](O)[C@H]1O]

and/or a pharmaceutically acceptable salt.

10. The method of embodiments 1 and 6, wherein said isolated water-soluble cannabinoid glycoside comprises the compound 11C:

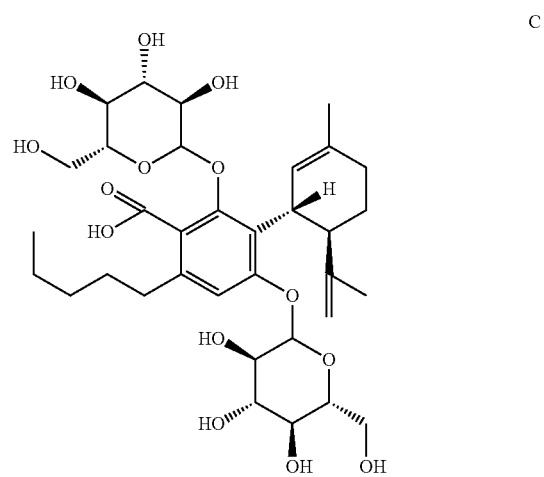

and/or a pharmaceutically acceptable salt.

11. The method of embodiments 1 and 6, wherein said isolated water-soluble cannabinoid glycoside comprises the compound 11D:

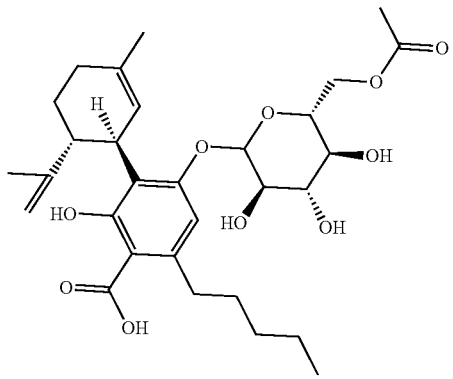

D and/or a pharmaceutically acceptable salt.

12. The method of embodiments 1 and 6, wherein said isolated water-soluble cannabinoid glycoside comprises the compound 11E:

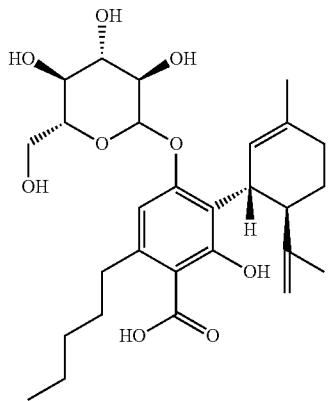

E and/or a pharmaceutically acceptable salt.

13. The method of embodiments 1 and 6, wherein said isolated water-soluble cannabinoid glycoside comprises the compound 11F:

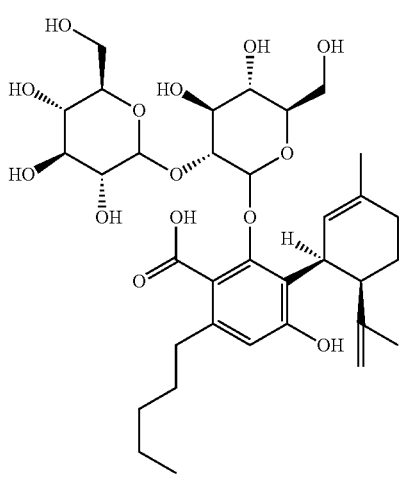

F and/or a pharmaceutically acceptable salt.

14. A method of generating a water-soluble cannabinoid comprising the step of introducing a cannabinoid compound to a UDP-glucosyltransferases (UGT) having glycosylation activity towards said cannabinoid wherein said UGT comprises a UGT selected from the group of amino acid sequences consisting of: SEQ ID NOs. 1-9181, and an amino acid sequence having 90% sequence identity with SEQ ID NOs. 1-9181, forming a cannabinoid glycoside.

15. The method of embodiment 14, wherein said step of introducing comprises the step of introducing selected from the group consisting of:
introducing a cannabinoid compound to a UGT having glycosylation activity towards said cannabinoid in an in vitro system;
introducing a cannabinoid compound to a UGT having glycosylation activity towards said cannabinoid in an ex vitro system; and
introducing a cannabinoid compound to a UGT having glycosylation activity towards said cannabinoid in an in vivo system.

16. The method of embodiment 15, wherein said ex vivo system comprises a bioreactor system, and said in vivo system comprises a cell culture, wherein said cell culture is further selected from the group consisting of a yeast cell culture, a bacterial cell culture, an algal cell culture, a fungi cell culture, and a plant cell culture.

17. The method of embodiment 14, wherein said cannabinoid compound is selected from the group consisting of: cannabidiol (CBD), cannabidiolic acid (CBDA), delta-9-tetrahydrocannabinol (THC), and tetrahydrocannabinolic acid (THCA).

18. The method of embodiment 17, wherein said CBD or said CBDA are glycosylated to form a 2×CBD Glycoside, and a 2×CBDA Glycoside respectively.

19. The method of embodiment 14, wherein said step of introducing comprises the step of introducing selected from the group consisting of: a cannabinoid extract containing a spectrum of cannabinoids, introducing one or more non-psychoactive cannabinoids, introducing one or more cannabinoid precursors, or introducing one and introducing one or more cannabinoid acids.

20. The method of embodiment 14, and further comprising isolating said water-soluble cannabinoid glycoside.

21. The method of embodiments 14 and 20, wherein said isolated water-soluble cannabinoid glycoside comprises the compound 10C:

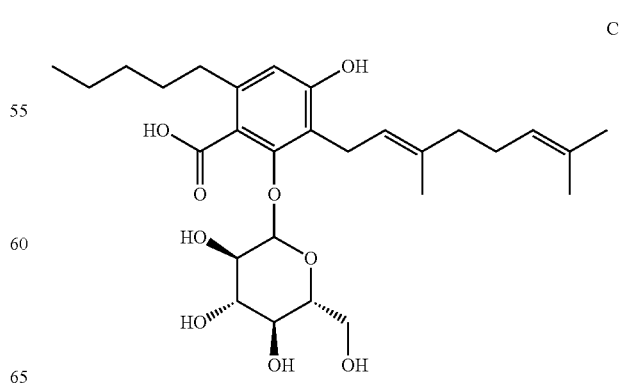

C and/or a pharmaceutically acceptable salt.

22. The method of embodiments 14 and 20, wherein said isolated water-soluble cannabinoid glycoside comprises the compound 10D:

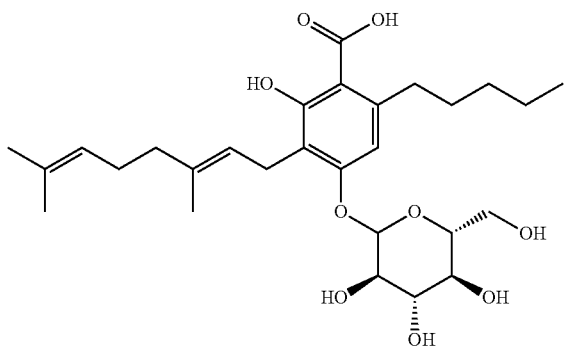

and/or a pharmaceutically acceptable salt.

23. The method of embodiments 14 and 20, wherein said isolated water-soluble cannabinoid glycoside comprises the compound 11B:

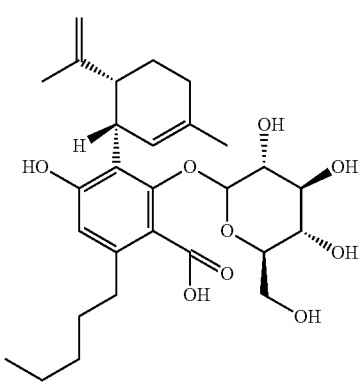

and/or a pharmaceutically acceptable salt.

24. The method of embodiments 14 and 20, wherein said isolated water-soluble cannabinoid glycoside comprises the compound 11C:

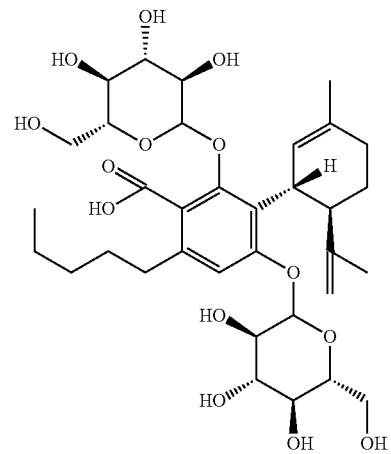

and/or a pharmaceutically acceptable salt.

25. The method of embodiments 14 and 20, wherein said isolated water-soluble cannabinoid glycoside comprises the compound 11D:

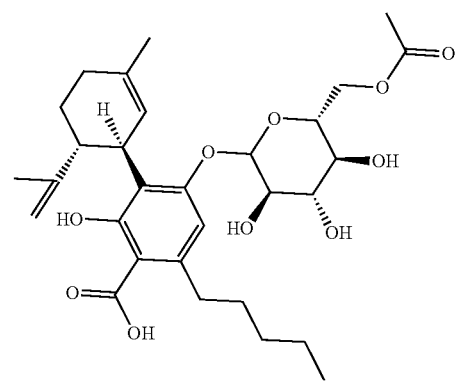

and/or a pharmaceutically acceptable salt.

26. The method of embodiments 14 and 20, wherein said isolated water-soluble cannabinoid glycoside comprises the compound 11E:

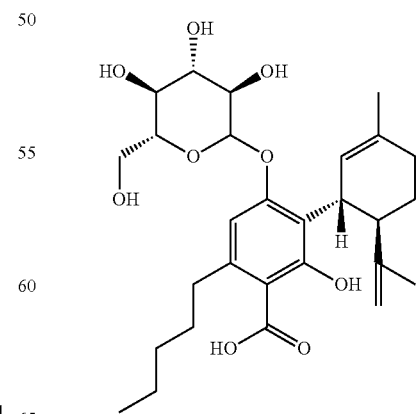

and/or a pharmaceutically acceptable salt.

27. The method of embodiments 14 and 20, wherein said isolated water-soluble cannabinoid glycoside comprises the compound 11F:

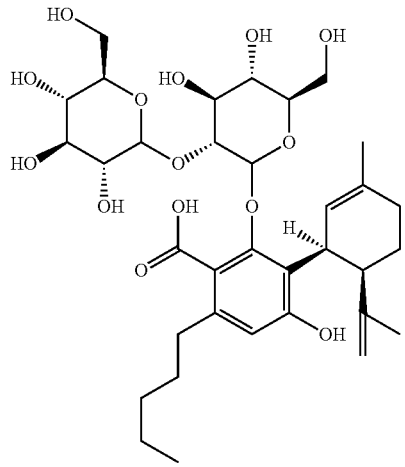

and/or a pharmaceutically acceptable salt.

28. A pharmaceutical preparations having at least one cannabinoid glycoside generated in an in vitro, ex vivo, or in vivo system by the action of one or more UDP-glucosyltransferases (UGT) having glycosylation activity towards one or more cannabinoid compounds according to SEQ ID NOs. 1-9181, and a nucleotide sequence encoding an amino acid sequence having 90% sequence identity with SEQ ID NOs. 1-9181.

29. A cannabinoid glycoside generated in an in vitro, ex vivo, or in vivo system by the action of one or more UDP-glucosyltransferases (UGT) have glycosylation activity towards one or more cannabinoid compounds according to SEQ ID NOs. 1-9181, and a nucleotide sequence encoding an amino acid sequence having 90% sequence identity with SEQ ID NOs. 1-9181, and/or a pharmaceutically acceptable salt.

30. A genetically modified cell that express a nucleotide sequence encoding a heterologous UDP-glucosyltransferases (UGT) having glycosylation activity towards one or more cannabinoid compounds operably linked to a promotor, wherein said heterologous UGT comprises a heterologous UGT selected from the group of amino acid sequences consisting of: SEQ ID NOs. 1-9181, and a nucleotide sequence encoding an amino acid sequence having 90% sequence identity with SEQ ID NOs. 1-9181.

31. The genetically modified cell of embodiment 30, wherein said genetically modified cell is selected from the group consisting of: a plant cell, a yeast cell, a bacterial cell, a fungi cell, and an algal cell.

32. The genetically modified cell of embodiment 30, wherein said genetically modified cell is selected from the group consisting of: a *Cannabis* plant cell, and a tobacco plant cell.

33. A method of generating a water-soluble cannabinoid comprising the step of introducing a cannabinoid compound to a UDP-glucosyltransferases (UGT) having glycosylation activity towards said cannabinoid forming a cannabinoid glycoside, wherein said UGT comprises a UGT selected from the group of amino acid sequences consisting of: a UGT from the structural group Gram+UGTs, structural group GT-A UGTs, and a UGT from the structural group GT-B UGTs.

34. The method of embodiment 33, wherein said step of introducing comprises the step of introducing selected from the group consisting of:
   introducing a cannabinoid compound to a UGT having glycosylation activity towards said cannabinoid forming a cannabinoid glycoside, in an in vitro system;
   introducing a cannabinoid compound to a UGT having glycosylation activity towards said cannabinoid forming a cannabinoid glycoside, in an ex vitro system; and
introducing a cannabinoid compound to a UGT having glycosylation activity towards said cannabinoid forming a cannabinoid glycoside, in an in vivo system.

35. The method of embodiment 34, wherein said ex vivo system comprises a bioreactor system, and said in vivo system comprises a cell culture, wherein said cell culture is further selected from the group consisting of a yeast cell culture, a bacterial cell culture, an algal cell culture, a fungi cell culture, and a plant cell culture.

36. The method of embodiment 33, wherein said cannabinoid compound is selected from the group consisting of: cannabidiol (CBD), cannabidiolic acid (CBDA), delta-9-tetrahydrocannabinol (THC), and tetrahydrocannabinolic acid (THCA).

37. The method of embodiment 33, wherein said structural group Gram+UGTs is selected from the group of UGT structural groups consisting of: 5tzk (SEQ ID NOs. 1-1182), 3bcv (SEQ ID NOs. 1183-1222), 5hea (SEQ ID NOs. 1223-1805), 6h21 (SEQ ID NOs. 1806-1825), and UGTs having 90% sequence identity with SEQ ID NOs. 1-1825, that have glycosylation activity towards one or more cannabinoid compounds.

38. The method of embodiment 33, wherein said structural group GT-A UGTs is selected from the group of UGT structural groups consisting of: 1g9r (SEQ ID NOs. 1826-1828), 2286 (SEQ ID NOs. 1829-1985), 3ckj (SEQ ID NOs. 1986-2453), 3e25 (SEQ ID NOs. 2454-3126), 3fly (SEQ ID NOs. 3127-3430), 4dec (SEQ ID NOs. 3431-3481), 5mlz (SEQ ID NOs. 3482-3639), 5nv4 (SEQ ID NOs. 3640-3693), 6fsn (SEQ ID NOs. 3694-4699), 6p61 (SEQ ID NOS. 4700-5259) and UGTs having 90% sequence identity with SEQ ID NOs. 1826-5259, that have glycosylation activity towards one or more cannabinoid compounds.

39. The method of embodiment 33, wherein said structural group GT-B UGTs is selected from the group of UGT structural groups consisting of: 2acv (SEQ ID NOs. 5260-6290), 2iya (SEQ ID NOs. 6290-6953), 3hbf (SEQ ID NOs. 6954-7484), 5g15 (SEQ ID NOs. 7485-7998), 3c48 (SEQ ID NOs. 7999-8243), 5nlm (SEQ ID NOs. 8244-8486), 5du2 (SEQ ID NOs. 8487-8612), 2clx (SEQ ID NOs. 8613-8688), 5zfk (SEQ ID NOs. 8689-8758), 4rel (SEQ ID NOs. 8759-8816), 3otg (SEQ ID NOs. 8817-8873), 5v2j (SEQ ID NOs. 8874-8921), 2r60 (SEQ ID NOs. 8922-8965), 4amg (SEQ ID NOs. 8966-9007), 4n9w (SEQ ID NOs. 9008-9046), 2pq6 (SEQ ID NOs. 9047-9082), 4wyi (SEQ ID NOs. 9083-9111), 6bk0 (SEQ ID NOs. 9112-9133), 6inf (SEQ ID NOs. 9134-9149), 3ia7 (SEQ ID NOs. 9150-9158), 5d01 (SEQ ID NOs. 9159-9165), 6ij9 (SEQ ID NOs. 9166-9170), 6d9t (SEQ ID NOs. 9171-9175), 2jjm (SEQ ID NOs. 9176-9180), 3mbo (SEQ ID NO. 9181) and UGTs having 90% sequence identity with SEQ ID NOs. 5260-9181, that have glycosylation activity towards one or more cannabinoid compounds.

40. An isolated nucleotide sequence operably linked to a promoter sequencer encoding at least one UDP-glucosyltransferases (UGT) having glycosylation activity towards at least one cannabinoid wherein said UGT comprises a UGT selected from the group of amino acid sequences consisting of: SEQ ID NOs. 1-9181, and a nucleotide sequence encoding an amino acid sequence having 90% sequence identity with SEQ ID NOs. 1-9181.

41. An isolated UDP-glucosyltransferases (UGT) having glycosylation activity towards THC and CBD, wherein said UGT comprises a UGT having a GT-A fold consisting of a single domain with a seven-stranded β-sheet flanked on both sides of the sheet by several a-helices.

42. The isolated UGT of embodiment 41, wherein the UGT having glycosylation activity towards THC and CBD is selected from the group consisting of: 5tzk (SEQ ID NOs. 1-1182), 3bcv (SEQ ID NOs. 1183-1222), 5hea (SEQ ID NOs. 1223-1805), 6h21 (SEQ ID NOs. 1806-1825), and UGTs having 90% sequence identity with SEQ ID NOs. 1-1825, that have glycosylation activity towards one or more cannabinoid compounds 43. An isolated UDP-glucosyltransferases (UGT) having glycosylation activity towards THC and CBD, wherein said UGT comprises a UGT having a GT-A fold consisting of a single domain with a seven-stranded β-sheet flanked on both sides of the sheet by several a-helices and also an additional tetratricopeptide repeat (TPR) motif that mediates the assembly of oligomers.

44. The isolated UGT of embodiment 43, wherein the UGT having glycosylation activity towards THC and CBD is selected from the group consisting of: 1g9r (SEQ ID NOs. 1826-1828), 2286 (SEQ ID NOs. 1829-1985), 3ckj (SEQ ID NOs. 1986-2453), 3e25 (SEQ ID NOs. 2454-3126), 3fly (SEQ ID NOs. 3127-3430), 4dec (SEQ ID NOs. 3431-3481), 5mlz (SEQ ID NOs. 3482-3639), 5nv4 (SEQ ID NOs. 3640-3693), 6fsn (SEQ ID NOs. 3694-4699), 6p61 (SEQ ID NOs. 4700-5259) and UGTs having 90% sequence identity with SEQ ID NOs. 1826-5259, that have glycosylation activity towards one or more cannabinoid compounds.

45. An isolated UGT having glycosylation activity towards THC and CBD, wherein said UGT comprises a UGT having a GT-B fold consisting of two distinct N-terminal and C-terminal domains that both adopt Rossmann-like folds.

46. The isolated UGT of embodiment 45, wherein the UGT having glycosylation activity towards THC and CBD is selected from the group consisting of: 2acv (SEQ ID NOs. 5260-6290), 2iya (SEQ ID NOs. 6290-6953), 3hbf (SEQ ID NOs. 6954-7484), 5g15 (SEQ ID NOs. 7485-7998), 3c48 (SEQ ID NOs. 7999-8243), 5nlm (SEQ ID NOs. 8244-8486), 5du2 (SEQ ID NOs. 8487-8612), 2clx (SEQ ID NOs. 8613-8688), 5zfk (SEQ ID NOs. 8689-8758), 4rel (SEQ ID NOs. 8759-8816), 3otg (SEQ ID NOs. 8817-8873), 5v2j (SEQ ID NOs. 8874-8921), 2r60 (SEQ ID NOs. 8922-8965), 4amg (SEQ ID NOs. 8966-9007), 4n9w (SEQ ID NOs. 9008-9046), 2pq6 (SEQ ID NOs. 9047-9082), 4wyi (SEQ ID NOs. 9083-9111), 6bk0 (SEQ ID NOs. 9112-9133), 6inf (SEQ ID NOs. 9134-9149), 3ia7 (SEQ ID NOs. 9150-9158), 5d01 (SEQ ID NOs. 9159-9165), 6ij9 (SEQ ID NOs. 9166-9170), 6d9t (SEQ ID NOs. 9171-9175), 2jjm (SEQ ID NOs. 9176-9180), 3mbo (SEQ ID NO. 9181) and UGTs having 90% sequence identity with SEQ ID NOs. 5260-9181, that have glycosylation activity towards one or more cannabinoid compounds.

47. An isolated nucleotide sequence operably linked to a promoter sequencer encoding at least one UDP-glucosyltransferases (UGT) having glycosylation activity towards THC or CBD wherein said UGT comprises a UGT selected from the group of amino acid sequences consisting of: SEQ ID NOs. 1-9181, and a nucleotide sequence encoding an amino acid sequence having 90% sequence identity with SEQ ID NOs. 1-9181.

Additional aspects of the invention may become evident based on the specification and figures presented below.

BRIEF DESCRIPTION OF THE FIGURES

FIG. 12. Shows the structural difference between UDP-glucuronic acid and UDP-glucose.

DETAILED DESCRIPTION OF THE INVENTION

Figure 1:
FIG. 1: CBD bound to Gram Positive Bacteria UDP-UGT 5tzk structure representative including a cannabinoid with the UDP co-factor of the UDP-glucose substrate.
Figure 2:
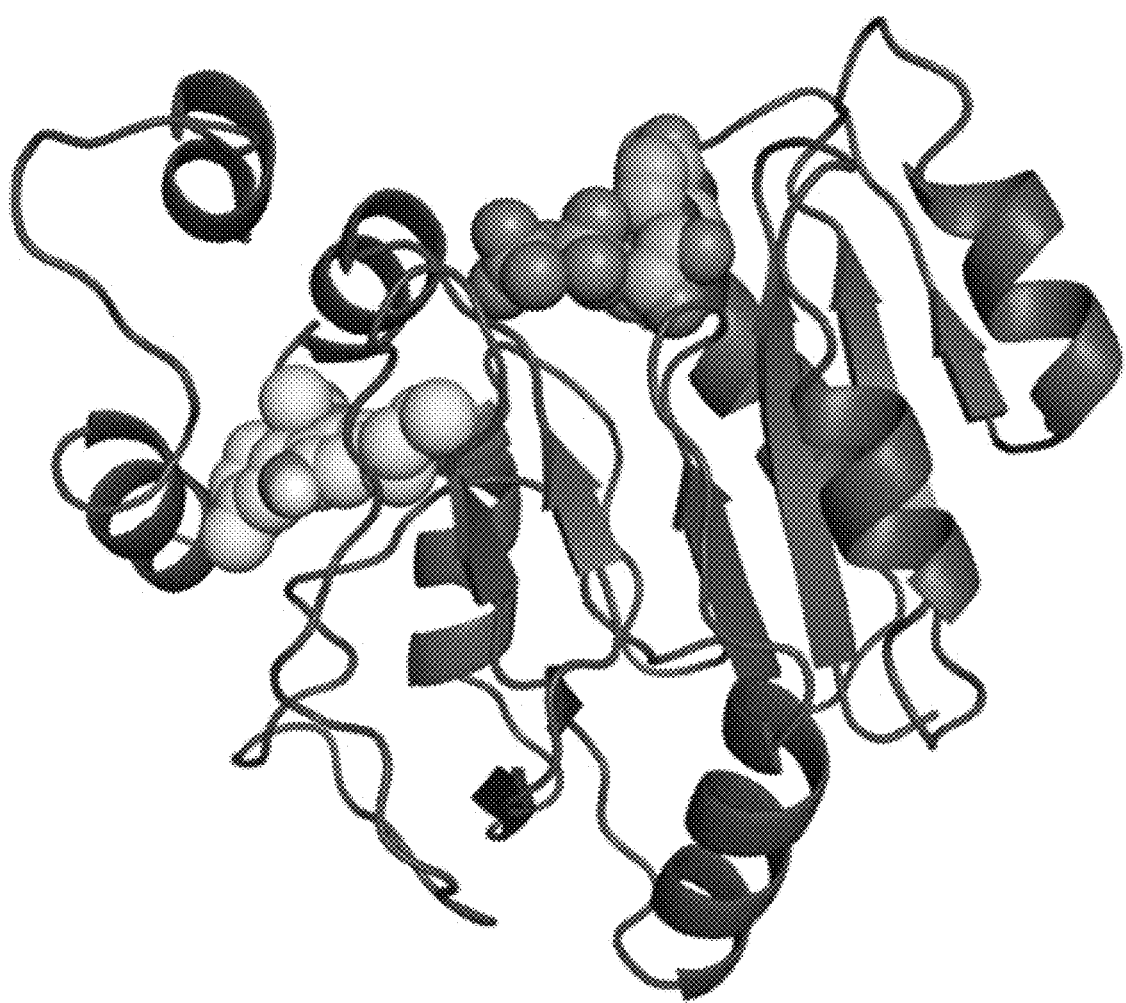
FIG. 2: THC bound to Gram Positive Bacteria UDP-UGT 5tzk structure representative including a cannabinoid with the UDP co-factor of the UDP-glucose substrate.
Figure 3:
FIG. 3: CBD bound to GT-A UDP-UGT 6p61c1 structure representative including a cannabinoid with the UDP co-factor of the UDP-glucose substrate.
Figure 4:
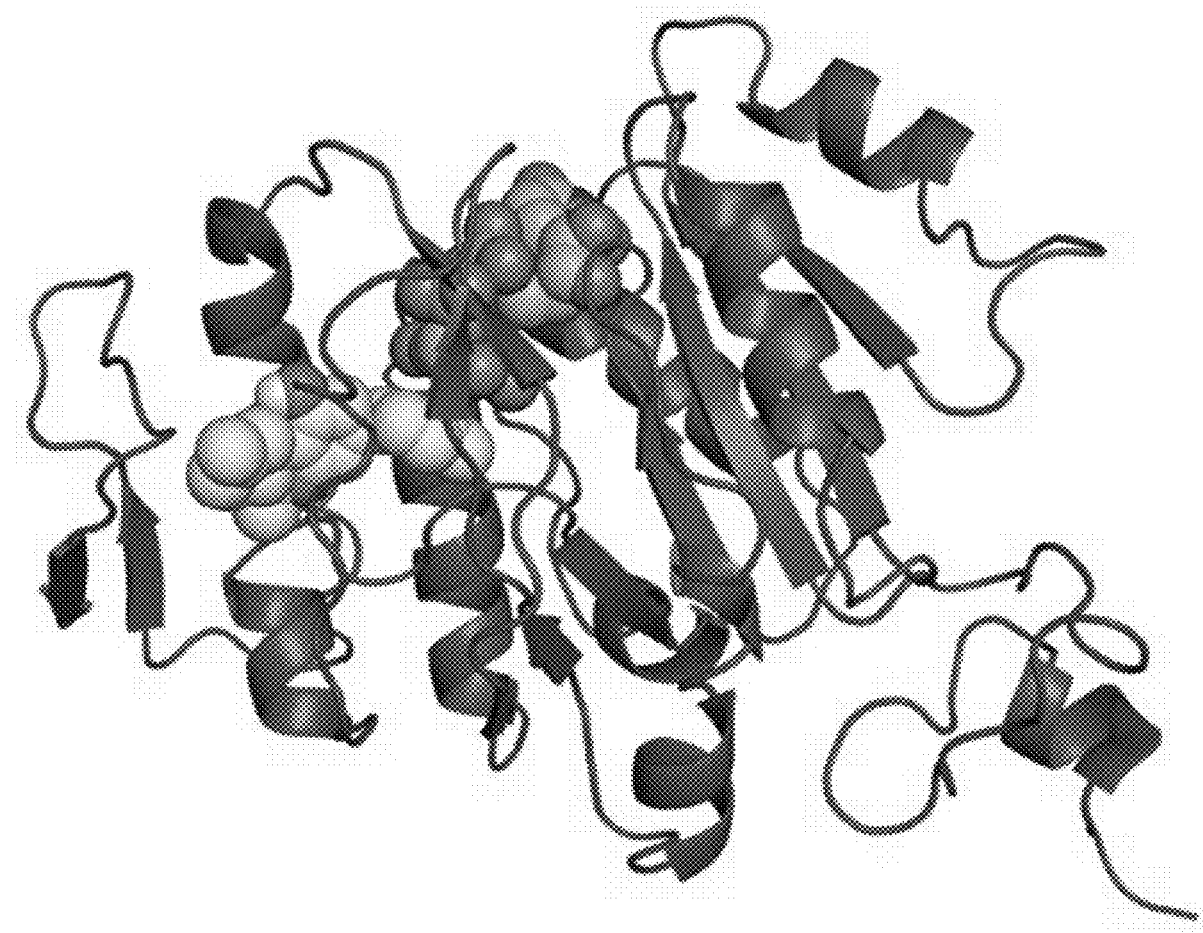
FIG. 4: THC bound to GT-A UDP-UGT 2286 structure representative including a cannabinoid with the UDP co-factor of the UDP-glucose substrate.
Figure 5:
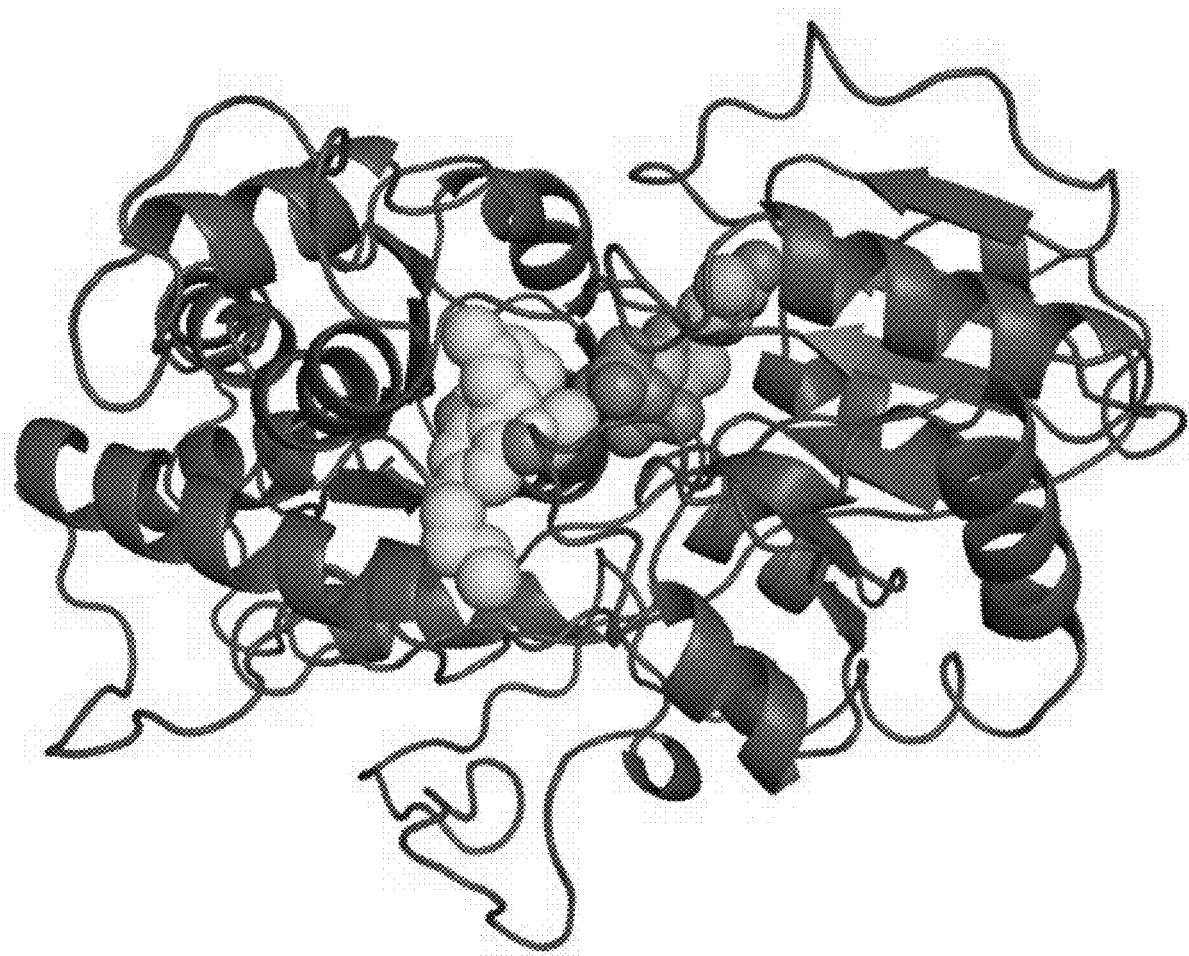
FIG. 5: CBD bound to GT-B UDP-UGT structure 3otg representative including a cannabinoid with the UDP co-factor of the UDP-glucose substrate.
Figure 6:
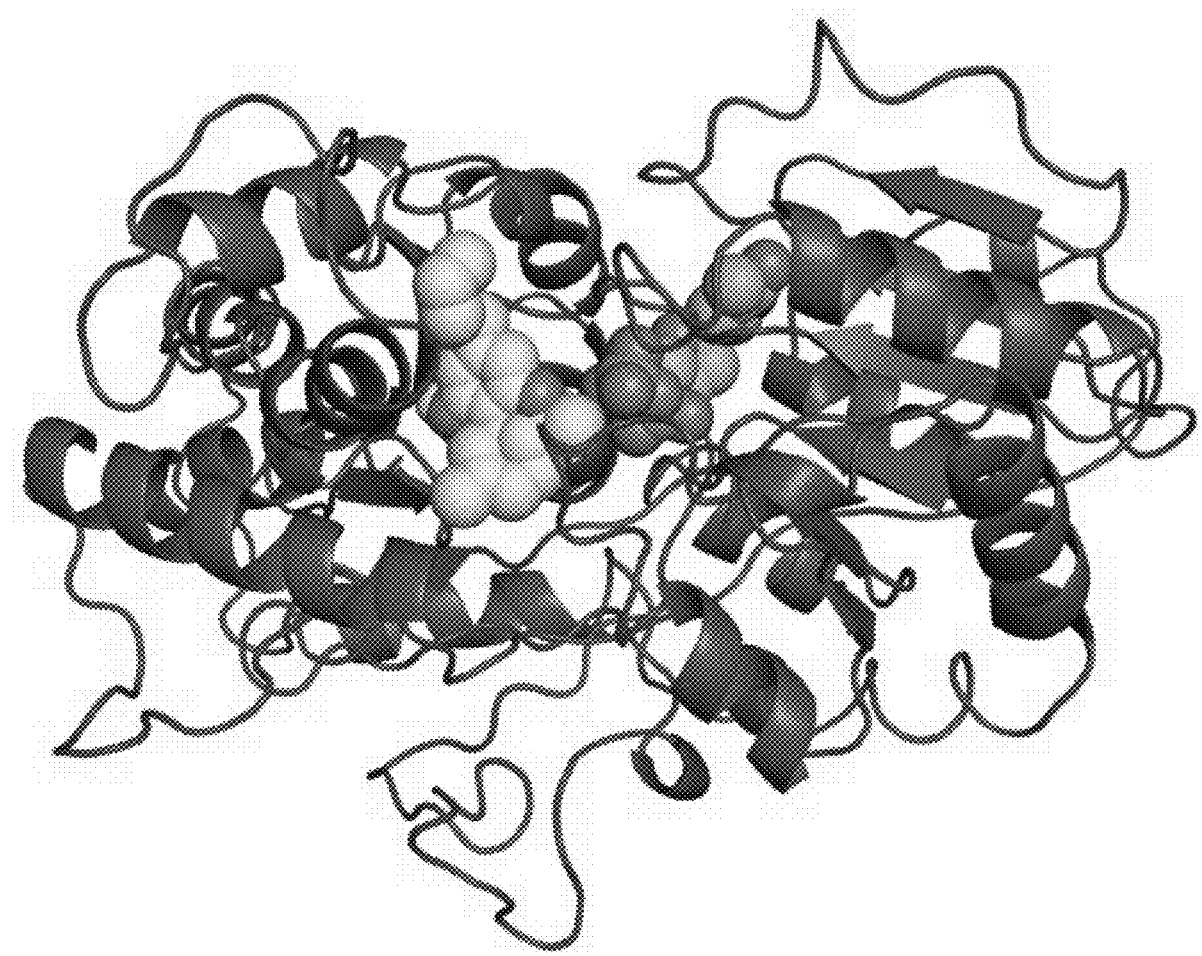
FIG. 6: THC bound to GT-B UDP-UGT structure 3otg representative including a cannabinoid with the UDP co-factor of the UDP-glucose substrate.

One embodiment of the present invention relates generally to the identification novel UDP-glucosyltransferases (UDP-UGTs or UGTs) enzymes having glycosylation activity towards one or more cannabinoid compounds. In one preferred embodiment, the present invention includes the identification of novel UGTs according to the amino acid sequences identified as SEQ ID NOs. 1-9181, and UGTs having 90% sequence identity with SEQ ID NOs. 1-9181, that have glycosylation activity towards one or more cannabinoid compounds, and preferably THC and CBD.

One embodiment of the present invention further relates generally to the use of novel UGT enzymes having specific activity towards one or more cannabinoid compounds to generate water-soluble cannabinoid glycoside compounds in in vitro, ex vivo, and in vivo systems. In one preferred embodiment, the present invention use of novel UGT enzymes according to the amino acid sequences identified as SEQ ID NOs. 1-9181, and UGTs having 90% sequence identity with SEQ ID NOs. 1-9181, that have glycosylation activity towards one or more cannabinoid compounds, and preferably THC and CBD, in in vitro, ex vivo, and in vivo systems. In one preferred embodiment of the invention, an in vivo system may include a whole organism system, such as a plant, or cell culture, such as a plant cell culture, an algal cell culture, a fungi cell culture, or a microorganism cell culture, such as a bacterial or yeast cell culture.

One embodiment of the present invention further relates generally to novel methods of generating water-soluble cannabinoid glycoside compounds, and preferably THC-glycosides and CBD-glycosides, comprising the step of introducing one or more cannabinoids to a UGT enzyme having specific activity towards one or more cannabinoid compounds according to the amino acid sequences identified as SEQ ID NOs. 1-9181, and UGTs having 90% sequence identity with SEQ ID NOs. 1-9181, that have glycosylation activity towards one or more cannabinoid compounds, in in vitro, ex vivo, and in vivo systems. In one preferred embodiment of the invention, an in vivo system may include a whole organism system, such as a plant, or cell culture, such as a plant cell culture, an algal cell culture, a fungi cell culture, or a microorganism cell culture, such as a bacterial or yeast cell culture. In other embodiments, an ex vivo system may include a bioreactor system. In other embodiments, an in vitro system may include chemical conversion of cannabinoids into water-soluble cannabinoid glycoside compounds.

Yet, another embodiment of the current inventive technology may include the generation of genetically modified organisms configured to produce water-soluble cannabinoid glycoside compounds. In one preferred embodiment, a plant, a plant cell, an algal cell, a fungi, a bacteria, or a yeast cell, may be genetically modified to express a nucleotide sequence encoding one or more UGTs that have glycosylation activity towards one or more cannabinoid compounds, and preferably a UGT selected from the group of nucleotide sequences consisting of: a nucleotide sequence encoding an amino acid sequence according to SEQ ID NOs. 1-9181, and a nucleotide sequence encoding an amino acid sequence having 90% sequence identity with SEQ ID NOs. 1-9181.

Another embodiment of the current inventive technology includes the isolated amino acid sequences encoding one or more UGTs that have glycosylation activity towards one or more cannabinoid compounds according to SEQ ID NOs. 1-9181, and amino acid sequence having 90% sequence identity with SEQ ID NOs. 1-9181.

Another embodiment of the current inventive technology includes a nucleotide sequence encoding one or more UGTs that have glycosylation activity towards one or more cannabinoid compounds according to SEQ ID NOs. 1-9181, and a nucleotide sequence encoding an amino acid sequence having 90% sequence identity with SEQ ID NOs. 1-9181.

Another embodiment of the current inventive technology includes an expression vector having a nucleotide sequence encoding one or more UGTs that have glycosylation activity towards one or more cannabinoid compounds according to SEQ ID NOs. 1-9181, and a nucleotide sequence encoding an amino acid sequence having 90% sequence identity with SEQ ID NOs. 1-9181, operably linked to a promoter.

Another embodiment of the current inventive technology includes one or more organisms, such as a plant, plant cell, bacteria, algae, fungi, or yeast cell, transformed by an expression vector having a nucleotide sequence encoding one or more UGTs that have glycosylation activity towards one or more cannabinoid compounds according to SEQ ID NOs. 1-9181, and a nucleotide sequence encoding an amino acid sequence having 90% sequence identity with SEQ ID NOs. 1-9181, operably linked to a promoter.

One embodiment of the present invention further relates generally to novel methods of generating water-soluble cannabinoid glycoside compounds, and preferably THC-glycosides and CBD-glycosides, comprising the step of introducing one or more cannabinoids to a UGT enzyme having specific activity towards one or more cannabinoid compounds according to the amino acid sequences identified as belonging to the Gram+of class of UGTs as described herein, in an in vitro, ex vivo, and in vivo systems. In this preferred embodiment, the Gram+of class of UGTs may include the following structural groups: 5tzk (SEQ ID NOs. 1-1182), 3bcv (SEQ ID NOs. 1183-1222), 5hea (SEQ ID NOs. 1223-1805), 6h21 (SEQ ID NOs. 1806-1825), and UGTs having 90% sequence identity with SEQ ID NOs. 1-1825, that have glycosylation activity towards one or more cannabinoid compounds. In one preferred embodiment of the invention, an in vivo system may include a whole organism system, such as a plant, or cell culture, such as a plant cell culture, an algal cell culture, a fungi cell culture, or a microorganism cell culture, such as a bacterial or yeast cell culture. In other embodiments, an ex vivo system may include a bioreactor system. In other embodiments, an in vitro system may include chemical conversion of cannabinoids into water-soluble cannabinoid glycoside compounds.

In another embodiment, one or more of cannabinoid glycoside compounds identified as: 10B, 10C, 10D, 11A, 11B, 11C, 11D, 11E and 11F, may be generated through the step of introducing one or more cannabinoids to a UGT enzyme having specific activity towards one or more cannabinoid compounds according to the amino acid sequences identified as belonging to the Gram+of class of UGTs as described herein, in an in vitro, ex vivo, and in vivo systems. In this preferred embodiment, the Gram+of class of UGTs may include the following structural groups: 5tzk (SEQ ID NOs. 1-1182), 3bcv (SEQ ID NOs. 1183-1222), 5hea (SEQ ID NOs. 1223-1805), 6h21 (SEQ ID NOs. 1806-1825), and UGTs having 90% sequence identity with SEQ ID NOs. 1-1825, that have glycosylation activity towards one or more cannabinoid compounds.

Yet, another embodiment of the current inventive technology may include the generation of genetically modified organisms configured to produce water-soluble cannabinoid glycoside compounds. In one preferred embodiment, a plant, a plant cell, an algal cell, a fungi, a bacteria, or a yeast cell, may be genetically modified to express a nucleotide sequence encoding one or more Gram+class of UGTs that have glycosylation activity towards one or more cannabinoid compounds, and preferably a UGT selected from the group of nucleotide sequences consisting of: a nucleotide sequence encoding an amino acid sequence according to SEQ ID NOs. 1-1825, and a nucleotide sequence encoding an amino acid sequence having 90% sequence identity with SEQ ID NOs. 1-1825.

Another embodiment of the current inventive technology includes the isolated amino acid sequences encoding one or more Gram+class of UGTs that have glycosylation activity towards one or more cannabinoid compounds according to SEQ ID NOs. 1-1825, and amino acid sequence having 90% sequence identity with SEQ ID NOs. 1-1825.

Another embodiment of the current inventive technology includes a nucleotide sequence encoding one or more Gram+class of UGTs that have glycosylation activity towards one or more cannabinoid compounds according to SEQ ID NOs. 1-1825, and a nucleotide sequence encoding an amino acid sequence having 90% sequence identity with SEQ ID NOs. 1-1825.

Another embodiment of the current inventive technology includes an expression vector having a nucleotide sequence encoding one or more Gram+class of UGTs that have glycosylation activity towards one or more cannabinoid compounds according to SEQ ID NOs. 1-9181, and a nucleotide sequence encoding an amino acid sequence having 90% sequence identity with SEQ ID NOs. 1-1825, operably linked to a promoter.

Another embodiment of the current inventive technology includes one or more organisms, such as a plant, plant cell, bacteria, algae, fungi, or yeast cell, transformed by an expression vector having a nucleotide sequence encoding one or more Gram+class of UGTs that have glycosylation activity towards one or more cannabinoid compounds according to SEQ ID NOs. 1-1825, and a nucleotide sequence encoding an amino acid sequence having 90% sequence identity with SEQ ID NOs. 1-1825, operably linked to a promoter.

One embodiment of the present invention further relates generally to novel methods of generating water-soluble cannabinoid glycoside compounds, and preferably THC-glycosides and CBD-glycosides, comprising the step of introducing one or more cannabinoids to a UGT enzyme having specific activity towards one or more cannabinoid compounds according to the amino acid sequences identified as belonging to the GT-A of class of UGTs as described herein, in an in vitro, ex vivo, and in vivo systems. In this preferred embodiment, the GT-A of class of UGTs may include the following structural groups: 1g9r (SEQ ID NOs. 1826-1828), 2286 (SEQ ID NOs. 1829-1985), 3ckj (SEQ ID NOs. 1986-2453), 3e25 (SEQ ID NOs. 2454-3126), 3fly (SEQ ID NOs. 3127-3430), 4dec (SEQ ID NOs. 3431-3481), 5mlz (SEQ ID NOs. 3482-3639), 5nv4 (SEQ ID NOs. 3640-3693), 6fsn (SEQ ID NOs. 3694-4699), 6p61 (SEQ ID NOs. 4700-5259) and UGTs having 90% sequence identity with SEQ ID NOs. 1826-5259, that have glycosylation activity towards one or more cannabinoid compounds.

In one preferred embodiment of the invention, an in vivo system may include a whole organism system, such as a plant, or cell culture, such as a plant cell culture, an algal cell culture, a fungi cell culture, or a microorganism cell culture, such as a bacterial or yeast cell culture. In other embodiments, an ex vivo system may include a bioreactor system. In other embodiments, an in vitro system may include chemical conversion of cannabinoids into water-soluble cannabinoid glycoside compounds.

In another embodiment, one or more of cannabinoid glycoside compounds identified as: 10B, 10C, 10D, 11A, 11B, 11C, 11D, 11E and 11F, may be generated through the step of introducing one or more cannabinoids to a UGT enzyme having specific activity towards one or more cannabinoid compounds according to the amino acid sequences identified as belonging to the Gram+of class of UGTs as described herein, in an in vitro, ex vivo, and in vivo systems. In this preferred embodiment, the GT-A of class of UGTs may include the following structural groups: 1g9r (SEQ ID NOs. 1826-1828), 2286 (SEQ ID NOs. 1829-1985), 3ckj (SEQ ID NOs. 1986-2453), 3e25 (SEQ ID NOs. 2454-3126), 3fly (SEQ ID NOs. 3127-3430), 4dec (SEQ ID NOs. 3431-3481), 5mlz (SEQ ID NOs. 3482-3639), 5nv4 (SEQ ID NOs. 3640-3693), 6fsn (SEQ ID NOs. 3694-4699), 6p61 (SEQ ID NOs. 4700-5259) and UGTs having 90% sequence identity with SEQ ID NOs. 1826-5259, that have glycosylation activity towards one or more cannabinoid compounds.

Yet, another embodiment of the current inventive technology may include the generation of genetically modified organisms configured to produce water-soluble cannabinoid glycoside compounds. In one preferred embodiment, a plant, a plant cell, an algal cell, a fungi, a bacteria, or a yeast cell, may be genetically modified to express a nucleotide sequence encoding one or more GT-A class of UGTs that have glycosylation activity towards one or more cannabinoid compounds, and preferably a UGT selected from the group of nucleotide sequences consisting of: a nucleotide sequence encoding an amino acid sequence according to SEQ ID NOs. 1826-5259, and a nucleotide sequence encoding an amino acid sequence having 90% sequence identity with SEQ ID NOs. 1826-5259.

Another embodiment of the current inventive technology includes the isolated amino acid sequences encoding one or more GT-A class of UGTs that have glycosylation activity towards one or more cannabinoid compounds according to SEQ ID NOs. 1826-5259, and amino acid sequence having 90% sequence identity with SEQ ID NOs. 1826-5259.

Another embodiment of the current inventive technology includes a nucleotide sequence encoding one or more GT-A class of UGTs that have glycosylation activity towards one or more cannabinoid compounds according to SEQ ID NOs. 1826-5259, and a nucleotide sequence encoding an amino acid sequence having 90% sequence identity with SEQ ID NOs. 1826-5259.

Another embodiment of the current inventive technology includes an expression vector having a nucleotide sequence encoding one or more GT-A class of UGTs that have glycosylation activity towards one or more cannabinoid compounds according to SEQ ID NOs. 1826-5259, and a nucleotide sequence encoding an amino acid sequence having 90% sequence identity with SEQ ID NOs. 1826-5259, operably linked to a promoter.

Another embodiment of the current inventive technology includes one or more organisms, such as a plant, plant cell, bacteria, algae, fungi, or yeast cell, transformed by an expression vector having a nucleotide sequence encoding one or more GT-A class of UGTs that have glycosylation activity towards one or more cannabinoid compounds according to SEQ ID NOs. 1826-5259, and a nucleotide sequence encoding an amino acid sequence having 90% sequence identity with SEQ ID NOs. 1826-5259, operably linked to a promoter.

One embodiment of the present invention further relates generally to novel methods of generating water-soluble cannabinoid glycoside compounds, and preferably THC-glycosides and CBD-glycosides, comprising the step of introducing one or more cannabinoids to a UGT enzyme having specific activity towards one or more cannabinoid compounds according to the amino acid sequences identified as belonging to the GT-B of class of UGTs as described herein, in an in vitro, ex vivo, and in vivo systems. In this preferred embodiment, the GT-B of class of UGTs may include the following structural groups: 2acv (SEQ ID NOs. 5260-6290), 2iya (SEQ ID NOs. 6290-6953), 3hbf (SEQ ID NOs. 6954-7484), 5g15 (SEQ ID NOs. 7485-7998), 3c48 (SEQ ID NOs. 7999-8243), 5nlm (SEQ ID NOs. 8244-8486), 5du2 (SEQ ID NOs. 8487-8612), 2clx (SEQ ID NOS. 8613-8688), 5zfk (SEQ ID NOs. 8689-8758), 4rel (SEQ ID NOs. 8759-8816), 3otg (SEQ ID NOs. 8817-8873), 5v2j (SEQ ID NOs. 8874-8921), 2r60 (SEQ ID NOs. 8922-8965), 4amg (SEQ ID NOs. 8966-9007), 4n9w (SEQ ID NOs. 9008-9046), 2pq6 (SEQ ID NOs. 9047-9082), 4wyi (SEQ ID NOs. 9083-9111), 6bk0 (SEQ ID NOs. 9112-9133), 6inf (SEQ ID NOs. 9134-9149), 3ia7 (SEQ ID NOs. 9150-9158), 5d01 (SEQ ID NOs. 9159-9165), 6ij9 (SEQ ID NOs. 9166-9170), 6d9t (SEQ ID NOs. 9171-9175), 2jjm (SEQ ID NOs. 9176-9180), 3mbo (SEQ ID NO. 9181) and UGTs having 90% sequence identity with SEQ ID NOs. 5260-9181, that have glycosylation activity towards one or more cannabinoid compounds. In one preferred embodiment of the invention, an in vivo system may include a whole organism system, such as a plant, or cell culture, such as a plant cell culture, an algal cell culture, a fungi cell culture, or a microorganism cell culture, such as a bacterial or yeast cell culture. In other embodiments, an ex vivo system may include a bioreactor system. In other embodiments, an in vitro system may include chemical conversion of cannabinoids into water-soluble cannabinoid glycoside compounds.

In another embodiment, one or more of cannabinoid glycoside compounds identified as: 10B, 10C, 10D, 11A, 11B, 11C, 11D, 11E and 11F, may be generated through the step of introducing one or more cannabinoids to a UGT enzyme having specific activity towards one or more cannabinoid compounds according to the amino acid sequences identified as belonging to the Gram+of class of UGTs as described herein, in an in vitro, ex vivo, and in vivo systems. In this preferred embodiment, the GT-B of class of UGTs may include the following structural groups: 2acv (SEQ ID NOs. 5260-6290), 2iya (SEQ ID NOs. 6290-6953), 3hbf (SEQ ID NOs. 6954-7484), 5g15 (SEQ ID NOs. 7485-7998), 3c48 (SEQ ID NOs. 7999-8243), 5nlm (SEQ ID NOs. 8244-8486), 5du2 (SEQ ID NOs. 8487-8612), 2clx (SEQ ID NOs. 8613-8688), 5zfk (SEQ ID NOs. 8689-8758), 4rcl (SEQ ID NOs. 8759-8816), 3otg (SEQ ID NOs. 8817-8873), 5v2j (SEQ ID NOs. 8874-8921), 2r60 (SEQ ID NOs. 8922-8965), 4amg (SEQ ID NOs. 8966-9007), 4n9w (SEQ ID NOs. 9008-9046), 2pq6 (SEQ ID NOs. 9047-9082), 4wyi (SEQ ID NOs. 9083-9111), 6bk0 (SEQ ID NOs. 9112-9133), 6inf (SEQ ID NOs. 9134-9149), 3ia7 (SEQ ID NOs. 9150-9158), 5d01 (SEQ ID NOs. 9159-9165), 6ij9 (SEQ ID NOs. 9166-9170), 6d9t (SEQ ID NOs. 9171-9175), 2jjm (SEQ ID NOs. 9176-9180), 3mbo (SEQ ID NO. 9181) and UGTs having 90% sequence identity with SEQ ID NOs. 5260-9181, that have glycosylation activity towards one or more cannabinoid compounds.

Yet, another embodiment of the current inventive technology may include the generation of genetically modified organisms configured to produce water-soluble cannabinoid glycoside compounds. In one preferred embodiment, a plant, a plant cell, an algal cell, a fungi, a bacteria, or a yeast cell, may be genetically modified to express a nucleotide sequence encoding one or more GT-B class of UGTs that have glycosylation activity towards one or more cannabinoid compounds, and preferably a GT-B class of UGT selected from the group of nucleotide sequences consisting of: a nucleotide sequence encoding an amino acid sequence according to SEQ ID NOs. 5260-9181, and a nucleotide sequence encoding an amino acid sequence having 90% sequence identity with SEQ ID NOs. 1-9181.

Another embodiment of the current inventive technology includes the isolated amino acid sequences encoding one or more GT-B class of UGTs that have glycosylation activity towards one or more cannabinoid compounds according to SEQ ID NOs. 5260-9181, and amino acid sequence having 90% sequence identity with SEQ ID NOs. 5260-9181.

Another embodiment of the current inventive technology includes a nucleotide sequence encoding one or more GT-B class of UGTs that have glycosylation activity towards one or more cannabinoid compounds according to SEQ ID NOs. 5260-9181, and a nucleotide sequence encoding an amino acid sequence having 90% sequence identity with SEQ ID NOs. 5260-9181.

Another embodiment of the current inventive technology includes an expression vector having a nucleotide sequence encoding one or more GT-B class of UGTs that have glycosylation activity towards one or more cannabinoid compounds according to SEQ ID NOs. 1-9181, and a nucleotide sequence encoding an amino acid sequence having 90% sequence identity with SEQ ID NOs. 5260-9181, operably linked to a promoter.

Another embodiment of the current inventive technology includes one or more organisms, such as a plant, plant cell, bacteria, algae, fungi, or yeast cell, transformed by an expression vector having a nucleotide sequence encoding one or more GT-B class of UGTs that have glycosylation activity towards one or more cannabinoid compounds according to SEQ ID NOs. 5260-9181, and a nucleotide sequence encoding an amino acid sequence having 90% sequence identity with SEQ ID NOs. 5260-9181, operably linked to a promoter.

One embodiment of the current inventive technology includes improved systems and methods for the bioconversion of cannabinoid compounds into water-soluble cannabinoid glycosides, or water-soluble acetyl cannabinoid glycosides in a bacterial, yeast, or plant cell culture system. In another preferred embodiment, a preferred plant cell culture system may include a *Cannabis* suspension cell culture, or a tobacco plant cell culture.

Another embodiment of the current inventive technology includes one or more consumer products, or pharmaceutical preparations having at least one cannabinoid glycoside generated in an in vitro, ex vivo, or in vivo system by the action of one or more UGTs that have glycosylation activity towards one or more cannabinoid compounds according to SEQ ID NOs. 1-9181, and a nucleotide sequence encoding an amino acid sequence having 90% sequence identity with SEQ ID NOs. 1-9181.

In one embodiment, the invention novel systems, methods and compositions for the production of water-soluble cannabinoid glycosides in plant cells. In one preferred embodiment, a plant, such as *Cannabis* or tobacco plant or cell, may be genetically modified to express one or more heterologous UGTs, preferably a UGT selected from the group consisting of SEQ ID NO. 1-9181).

In another embodiment, the invention novel systems, methods and compositions for the production of water-soluble cannabinoid glycosides in yeast or bacteria cells. In one preferred embodiment, a plant, such as yeast or bacterial cell, may be genetically modified to express one or more heterologous UGTs, preferably a UGT selected from the group consisting of SEQ ID NO. 1-9181). In one preferred embodiment, a culture of yeast cells, such as *Saccharomyces cerevisiae, Kluyveromyces marxianus*, or *Pichia pastoris* or other suitable yeast species, may be established in a fermenter or other similar apparatus. It should be noted that the use of the above identified example in this embodiment is exemplary only, as various yeast strains, mixes of strains, hybrids of different strains or clones may be used to generate a suspension culture. In certain cases, such fermenters may include large industrial-scale fermenters allowing for a large quantity of yeast cells to be grown. In this embodiment, it may be possible to culture a large quantity of cells from a single-strain of, for example, *S. cerevisiae, P. pastoris*, or *K. marxianus*, which may establish a cell culture having a consistent rate of cannabinoid modification. Such cultured growth may be continuously sustained with the continual addition of nutrient and other growth factors being added to the culture. Such features may be automated or accomplished manually.

As noted above, cannabinoid producing strains of *Cannabis*, such as *Cannabis sativa* or hemp, as well as other plants may be utilized with the inventive technology. In certain preferred embodiments, *Cannabis* plant material may be harvested and undergo cannabinoid extraction through one or more of the methods generally known in the art. These extracted cannabinoids may be introduced into a genetically modified yeast suspension cell culture to be further modified, in some embodiment to express one or more heterologous UGTs having glycosylation activity directed towards one or more cannabinoids such as CBD or THC and the like.

As noted above, accumulation of high-levels of cannabinoids may be toxic for the yeast cell. As such, the inventive technology may modify the cannabinoids produced in a cell culture in vivo. In one preferred embodiment, cytochrome P450's (CYP) monooxygenases may be utilized to functionalize the chemical structure of the cannabinoids to more efficiently produce water-soluble cannabinoid glycosides. CYPs constitute a major enzyme family capable of catalyzing the oxidative biotransformation of many pharmacologically active chemical compounds and other lipophilic xenobiotics. For example, the most common reaction catalyzed by cytochromes P450 is a monooxygenase reaction, e.g., insertion of one atom of oxygen into the aliphatic position of an organic substrate (RH) while the other oxygen atom is reduced to water:

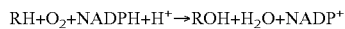

$RH+O_2+NADPH+H^+ \rightarrow ROH+H_2O+NADP^+$

Several cannabinoids, including THC, have been shown to serve as a substrate for human CYPs (CYP2C9 and CYP3A4). Similarly, CYPs have been identified that metabolize cannabidiol (CYPs 2C19, 3A4); cannabinol (CYPs 2C9, 3A4); JWH-018 (CYPs 1A2, 2C9); and AM2201 (CYPs 1A2, 2C9). For example, as shown generally below, in one exemplary system, CYP2C9 may hydroxylate a THC molecule resulting in a hydroxyl form of THC. Further oxidation of the hydroxyl form of THC by CYP2C9 may convert it into a carboxylic acid form, which loses its psychoactive capabilities rendering it an inactive metabolite.

In one embodiment, a cell, and preferably a yeast cell may be transformed with a nucleotide sequence operably linked to a promoter encoding one or more heterologous CYPs. In one preferred embodiment, genes encoding one or more non-human isoforms and/or analogs, as well as possibly other CYPs that may functionalize cannabinoids may be expressed in transgenic yeast grown in a culture. In this preferred embodiment, NADPH-cytochrome P450 oxidoreductase (CPR) may be used to assist in the activity/function of one or more of the CYPs expressed within a genetically modified cell, and preferably a yeast cell. In this embodiment, CPR may serve as an electron donor to eukaryotic CYPs facilitating their enzymatic function within the transgenic yeast strain(s) described above. In one preferred embodiment, genes encoding a heterologous CPR, or one or more non-human isoforms and/or analogs of CPR that may act as an electron donor to CYPs may be expressed in transgenic yeast grown in a suspension culture.

Additional steps may be taken to further convert the functionalized cannabinoids into water-soluble cannabinoid glycosides. In an exemplary embodiment shown below, the inventive technology may utilize one or more UGT to catalyze the UGT to catalyze the transfer of the glucuronic acid component of UDP-glucuronic acid to a small hydrophobic molecule such as a cannabinoid.

In one preferred embodiment, the inventive technology may include the generation of transgenic yeast strains having artificial genetic constructs that that may express one or more UGT, or other enzymes capable converting hydrophobic and insoluble cannabinoids into water-soluble cannabinoid glycosides. In one preferred embodiment, artificial genetic constructs having genes encoding one or more UDP-UGTs, including non-human analogues of those described above, as well as other isoforms, may be expressed in transgenic yeast cells and grown in suspension or other cell cultures. In this embodiment, one or more cannabinoids may be added to the yeast cell culture where they are introduced to the heterologous expressed UGTs, for example one of SEQ ID NO. 1-918, such that the cannabinoid compound is glycosylated and converted into a water-soluble cannabinoid glycoside. This water-soluble cannabinoid glycoside may preferably be a THC-glycoside or a CBD glycoside, or even a THCA-glycoside or a CBDA-glycoside.

The water-soluble cannabinoids may be extracted from the cell cultures supernatant/media, or from the cells. In this preferred embodiment, a transformed yeast cells may be lysed such that accumulated cannabinoid glycosides are released to the surrounding lysate. Additional steps may include treating this lysate. Examples of such treatment may include filtering, centrifugation or screening to remove extraneous cellular material as well as chemical treatments to improve later cannabinoid glycoside yields.

The cannabinoid glycosides may be further isolated and purified. In one preferred embodiment, the culture's supernatant/media, or the cell's lysate may be processed utilizing affinity chromatography or other purification methods. In this preferred embodiment, an affinity column having a ligand configured to bind with one or more of the cannabinoid glycosides, for example, through association with the glucuronic acid functional group, among others, may be immobilized or coupled to a solid support. The material may then be passed over the column such that the cannabinoid glycosides, having specific binding affinity to the ligand become bound and immobilized. In some embodiments, non-binding and non-specific binding proteins that may have been present in the lysate may be removed. Finally, the cannabinoid glycosides may be eluted or displaced from the affinity column by, for example, a corresponding sugar or other compound that may displace or disrupt the cannabinoid-ligand bond. The eluted cannabinoid glycosides may be collected and further purified or processed.

In yet another separate embodiment, the water-soluble cannabinoid glycosides may be passively and/or actively excreted from a cell, and preferably a yeast cell. In one exemplary model, an ATP-binding cassette transporter (ABC transporters) or other similar molecular structure may recognize the glucuronic acid functional group (conjugate) on the transiently modified cannabinoid and actively transport it into the surrounding media. (Examples and sequences for ABC transporters are generally described in Sayre et al. PCT/US18/24409 and PCT/US18/41710, such examples and sequences being incorporated herein by reference). In this embodiment, a yeast cell culture may be allowed to grow until an output parameter is reached. In one example, an output parameter may include allowing the yeast cell culture to grow until a desired cell/optical density is reached, or a desired level of cannabinoid glycosides is reached. In this embodiment, the culture media containing the cannabinoid glycosides may be harvested for later cannabinoid extraction. In some embodiments, this harvested media may be treated in a manner similar to the lysate generally described above. Additionally, the transiently modified cannabinoids present in the raw and/or treated media may be isolated and purified, for example, through affinity chromatography in a manner similar to that described above.

The inventive technology may also include a system to convert or reconstitute cannabinoid glycosides. In one preferred embodiment, glycosylated cannabinoids may be converted into non-glycosylated cannabinoids through their treatment with one or more generalized or specific glycosidases. In this embodiment, these glycosidase enzymes may remove a sugar moiety. Specifically, these glycosidases may remove the glucuronic acid moiety reconstituting the cannabinoid compound to a form exhibiting psychoactive activity. This reconstitution process may generate a highly purified "entourage" of primary and secondary cannabinoids. These reconstituted cannabinoid compounds may also be incorporated into various solid and/or liquid compositions for use in a variety of pharmaceutical and other commercial applications.

Another aspect of the current invention may include systems, methods and compositions for the glycosylation in whole cannabinoid-producing plants and cell cultures, preferably *Cannabis*. In this embodiment, such *Cannabis* plants or cell cultures may be genetically modified to direct cannabinoid synthesis to the cytosol, as opposed to a trichome structure as described in PCT/US18/24409 and PCT/US18/41710, by Sayre et al., being incorporated herein by reference directed to such production localization in a *Cannabis* plant or plant cell. Such *Cannabis* plant or cell culture may be genetically modified to express one or more heterologous UGTs having glycosylation activity towards at least one cannabinoid, for example SEQ ID NOs. 1-9181. In additional embodiments, a plant or cell may be further genetically modified to express one or more heterologous UGTs, wherein in said polynucleotides encoding such UGTs may be codon-optimized for expression in an exogenous system, such as in yeast. In additional embodiments, a heterologous or exogenous, the terms being generally interchangeable, cytochrome P450 and/or a P450 oxidoreductase may be expressed. In this configuration a heterologous cytochrome P450 (for example as described in PCT/US18/24409 and PCT/US18/41710, by Sayre et al., such sequences being incorporated herein by reference) may hydroxylate a cannabinoid to form a hydroxylated cannabinoid and/or oxidizes a hydroxylated cannabinoid to form a cannabinoid carboxylic acid. Further, in this embodiment, a heterologous P450 oxidoreductase may facilitate electron transfer from a nicotinamide adenine dinucleotide phosphate (NADPH) to said cytochrome P450.

As noted above, a heterologous UGT may glycosylate a cannabinoid compound and thereby produce a water-soluble cannabinoid glycoside that may be reconstituted to its original forms through the action of a glycosidase that may remove the sugar moiety.

Another aspect of the current invention may include systems, methods and compositions for the glycosylation of cannabinoid compounds in a cell cultures, preferably a microorganism cell culture, preferably yeast, bacteria, fungi or algal cell culture. In one embodiment, a yeast culture may be genetically modified to biosynthesize one or more cannabinoids. The yeast cell culture may be further genetically modified to express one or more heterologous UGTs having glycosylation activity towards at least one cannabinoid, for example SEQ ID NOs. 1-9181, as well as in some embodiments, a heterologous cytochrome P450 and/or a P450 oxidoreductase.

Another aspect of the current invention may include systems, methods and compositions for the coupled glycosylation cannabinoid compounds in a cell cultures, preferably yeast, bacteria, fungi or algal cell culture. In one embodiment, a yeast culture may be genetically modified to express one or more heterologous UGTs, for example SEQ ID NOs. 1-9181, having glycosylation activity towards at least one cannabinoid, as well as in some embodiments, a heterologous cytochrome P450 and/or a P450 oxidoreductase. As noted above, in one preferred embodiment, a quantity of cannabinoids may be added to the cell culture, and preferably a yeast cell culture, where heterologous UGTs may glycosylate the cannabinoid forming a water-soluble cannabinoid glycoside. This cannabinoid glycoside may be released from the carrier may be further isolated or reconstituted to their original forms through the action of a glycosidase.

Another embodiment of the current invention may include systems, methods and compositions for the generation of water soluble cannabinoid glycoside compounds in whole plants and plant cell cultures.

In this preferred embodiment, this N-terminal trichome targeting sequence or domain may generally include the first 28 amino acid residues of a generalized synthase and may be coupled with a UGT, and preferably a UGT selected from the group consisting of SEQ ID NO. 1-9181. Exemplary N-terminal trichome targeting sequence for THCA synthase and CBDA synthase are identified by Sayre et al., PCT/US18/41710, such sequences being specifically incorporated here by reference. This extracellular targeting sequence may be recognized by the plant cell and cause the transport of the UGT from the cytoplasm to the plant's trichome, and in particular the storage compartment of the plant trichome where extracellular cannabinoid glycosylation may occur. More specifically, in this preferred embodiment, one or more UGT, and preferably a UGT selected from the group consisting of SEQ ID NO. 1-9181, may either be engineered to express all or part of the N-terminal extracellular targeting sequence as present in an exemplary synthase enzyme.

Generally, a trichome structure, such as in *Cannabis*, will have limited substrate for a UGT to use to effectuate glycosylation. To resolve this problem, in one embodiment, the invention may include systems, methods and compositions to increase substrates for UGTs in a plant trichome structure. In this preferred embodiment, an exogenous or endogenous UDP-glucose/UDP-galactose transporter may be expressed in a trichome producing plant, such as *Cannabis* plant. exemplary sequences being identified by Sayre et al., PCT/US18/41710, such sequences being specifically incorporated here by reference. In this embodiment, the UDP-glucose/UDP-galactose transporter may be modified to include a plasma-membrane targeting sequence and/or domain, exemplary sequences being identified by Sayre et al., PCT/US18/41710, such sequences being specifically incorporated here by reference. With this targeting domain, the UDP-glucose/UDP-galactose transporter may allow the artificial fusion protein to be anchored to the plasma membrane. In this configuration, sugar substrates from the cytosol may pass through the plasma membrane bound UDP-glucose/UDP-galactose transporter into the trichome. In this embodiment, substrates for UGTs may be localized to the trichome and allowed to accumulate further allowing enhanced glycosylation of cannabinoids in the trichome.

In additional embodiments, such plants or cell cultures may be genetically modified to direct cannabinoid synthesis to the cytosol, as opposed to a trichome structure. In one preferred embodiment, cannabinoid biosynthesis may be redirected from the plant's trichome to be localized in the plant cell's cytosol. In certain embodiments, a cytosolic cannabinoid production system may be established as described in PCT/US18/24409 and PCT/US18/41710, both by Sayre et al. (these applications are both incorporated by reference with respect to their disclosure related to cytosolic cannabinoid production and/or modification in whole, and plant cell systems). In one embodiment, a cytosolic cannabinoid production system may include the in vivo creation of one or more recombinant proteins that may allow cannabinoid biosynthesis to be localized to the cytosol where one or more heterologous UGT proteins may also be expressed and present in the cytosol. This inventive feature allows not only higher levels of cannabinoid production and accumulation, but efficient production of cannabinoids in suspension cell cultures. Even more importantly, this inventive feature allows cannabinoid glycoside production and accumulation without a trichome structure in whole plants, allowing cells that would not traditionally produce cannabinoids, such as cells in *Cannabis* leaves and stalks, to become cannabinoid-producing cells More specifically, in this preferred embodiment, one or more cannabinoid synthases may be modified to remove all or part of an N-terminal extracellular trichome targeting. Exemplary N-terminal trichome targeting sequence for THCA synthase and CBDA synthase are identified by Sayre et al., PCT/US18/41710. Co-expression with this cytosolic-targeted synthase with a heterologous UGT may allow the localization of cannabinoid synthesis to the cytosol. As noted below, in certain embodiments cannabinoid biosynthesis may be coupled with cannabinoid glycosylation in a cell cytosol. For example, in one preferred embodiment a UGT (for example SEQ ID NOs. 1-9181) may be expressed in a cell, preferably a cannabinoid producing cell, and even more preferably a *Cannabis* cell and be further engineered to be directed to the cell's cytosol. Such cytosolic targeted UGT enzymes may be co-expressed with heterologous catalase and cannabinoid transporters or other genes that may reduce cannabinoid biosynthesis toxicity and/or facilitate transport through or out of the cell. In certain embodiments, a catalase enzyme may be co-expressed with a UGT of the invention. In one embodiment a heterologous catalase is selected from the group of catalase sequences identified in PCT/US18/24409 and PCT/US18/41710, both by Sayre et al., such catalase sequences being incorporated herein by reference. Such cytosolic targeted enzymes may also be co-expressed with one or more myb transcriptions factors that may enhance metabolite flux through the cannabinoid biosynthetic pathway which may increase cannabinoid production. In one embodiment a myb transcription factor may be endogenous to *Cannabis*, or an ortholog thereof. Examples of endogenous or endogenous like, myb transcription factor may include those identified by Sayre et al., PCT/US18/41710, such specific sequences being incorporated herein by reference.

Notably, in a preferred embodiment, one or more endogenous cannabinoid synthase genes may be disrupted and/or knocked out and replaced with cytosolic-targeted cannabinoid synthase proteins as described herein. The disrupted endogenous cannabinoid synthase gene(s) may be the same or different than the expressed cytosolic-targeted cannabinoid synthase protein. Methods of disrupting or knocking-out a gene are known in the art and could be accomplished by one of ordinary skill without undue experimentation, for example through CRISPR, Talen, and zinc-finger exonuclease systems, as well as heterologous recombination techniques.

In another embodiment, one or more endogenous cannabinoid synthase genes may be disrupted and/or knocked out in a *Cannabis* plant or suspension cell culture wherein one or more cannabinoid synthase genes has been disrupted and/or knocked out is selected from the group consisting of: a CBG synthase gene; a THCA synthase, a CBDA synthase, and a CBCA synthase. In this embodiment, the *Cannabis* plant or suspension cell culture may express a polynucleotide encoding one or more cannabinoid synthases having its trichome targeting sequence disrupted and/or removed which may be selected from the group consisting of: a CBG synthase gene having its trichome targeting sequence disrupted and/or removed; a THCA synthase having its trichome targeting sequence disrupted and/or removed; a CBDA synthase having its trichome targeting sequence disrupted and/or removed; and a CBCA synthase having its trichome targeting sequence disrupted and/or removed.

Figure 10:
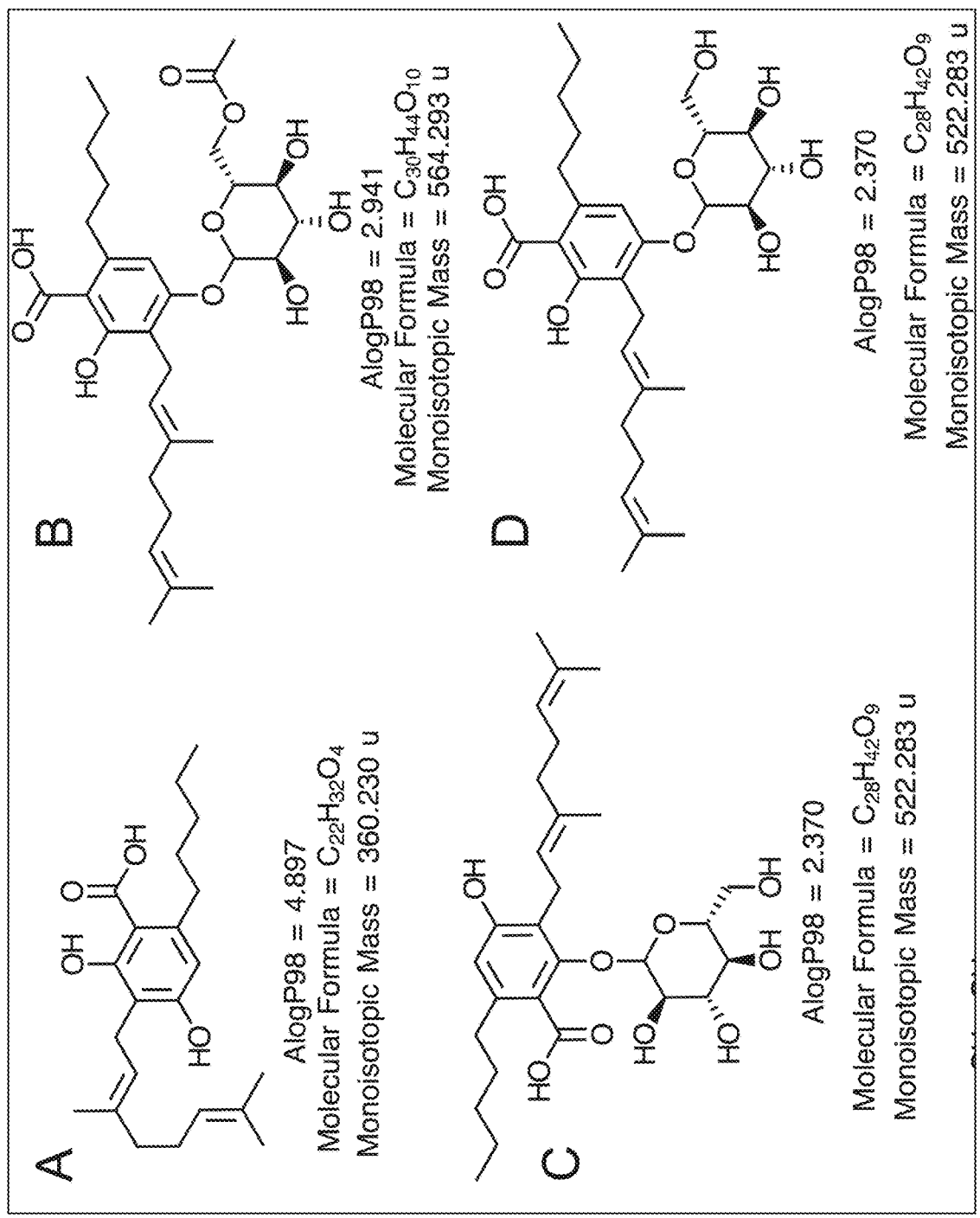
FIG. 10A-D. CBGA Glycoside Structures with Physiochemical and Constitutional Properties. A) CBGA, B) O Acetyl Glycoside, C) 1×Glycoside, D) 1×Glycoside FIG. 11A-F. CBDA Glycoside Structures with Physiochemical and Constitutional Properties. A) CBDA, B) 1×Glycoside, C) 2×Glycoside, D)O-Acetyl Glycoside, E) 1×Glycoside, F) 2×Glycoside, the disaccharide moiety can also be located on the opposite R—OH of CBDA as illustrated with the single glycoside product found in panels B & E.
Figure 11:
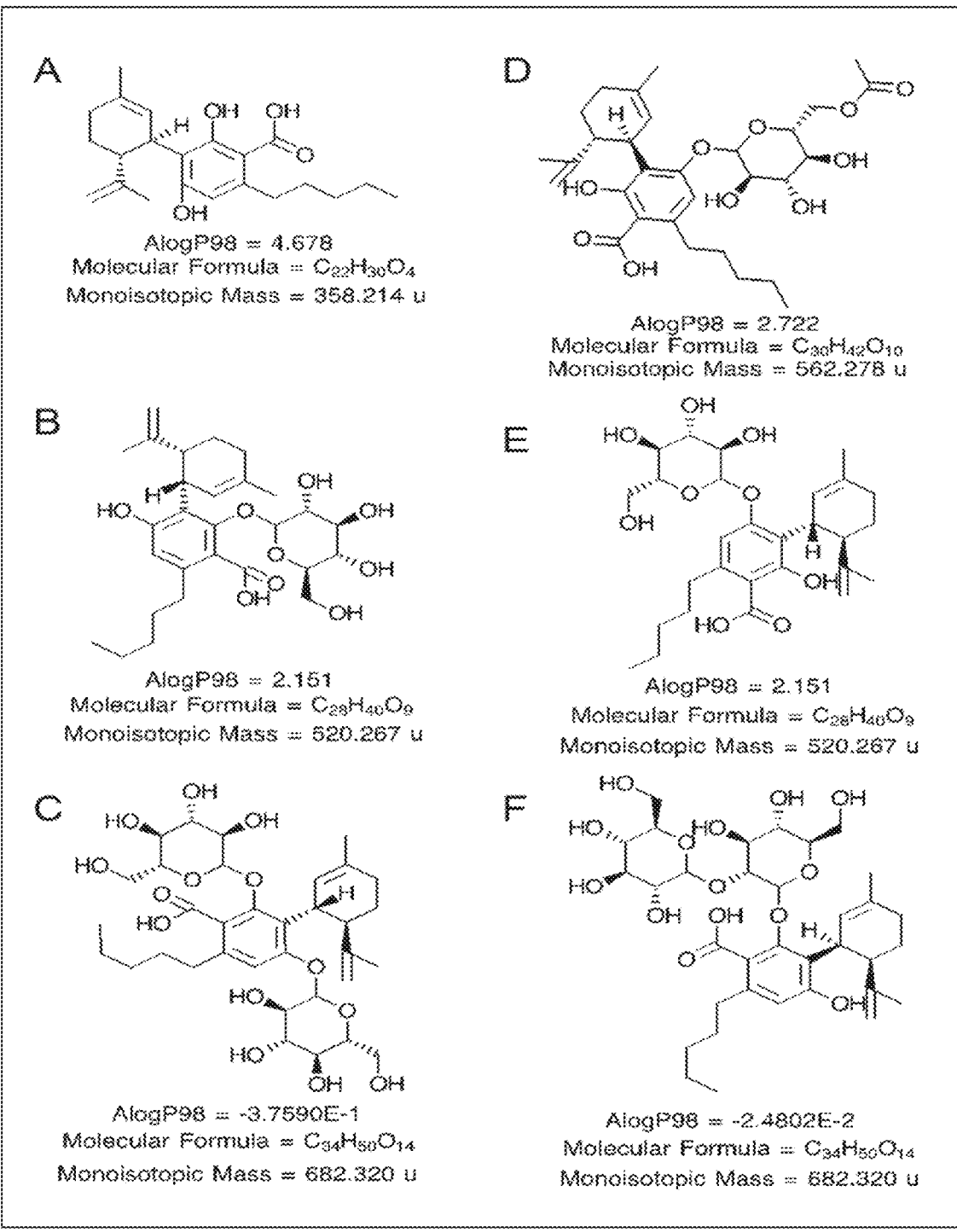
Figure 13:
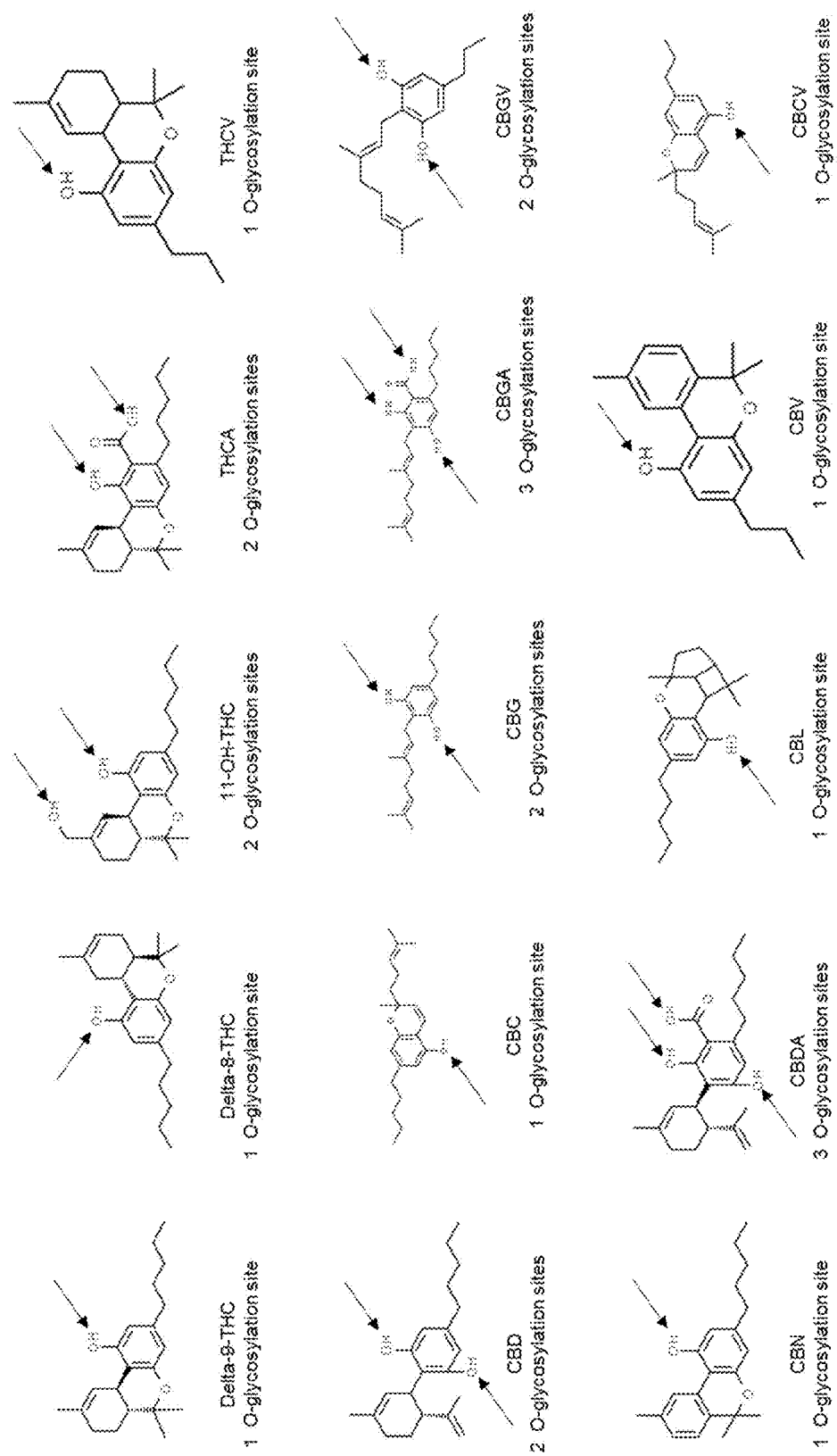
FIG. 13. Shows a representative number of cannabinoids having one or more identified glycosylation cites.
Figure 13:
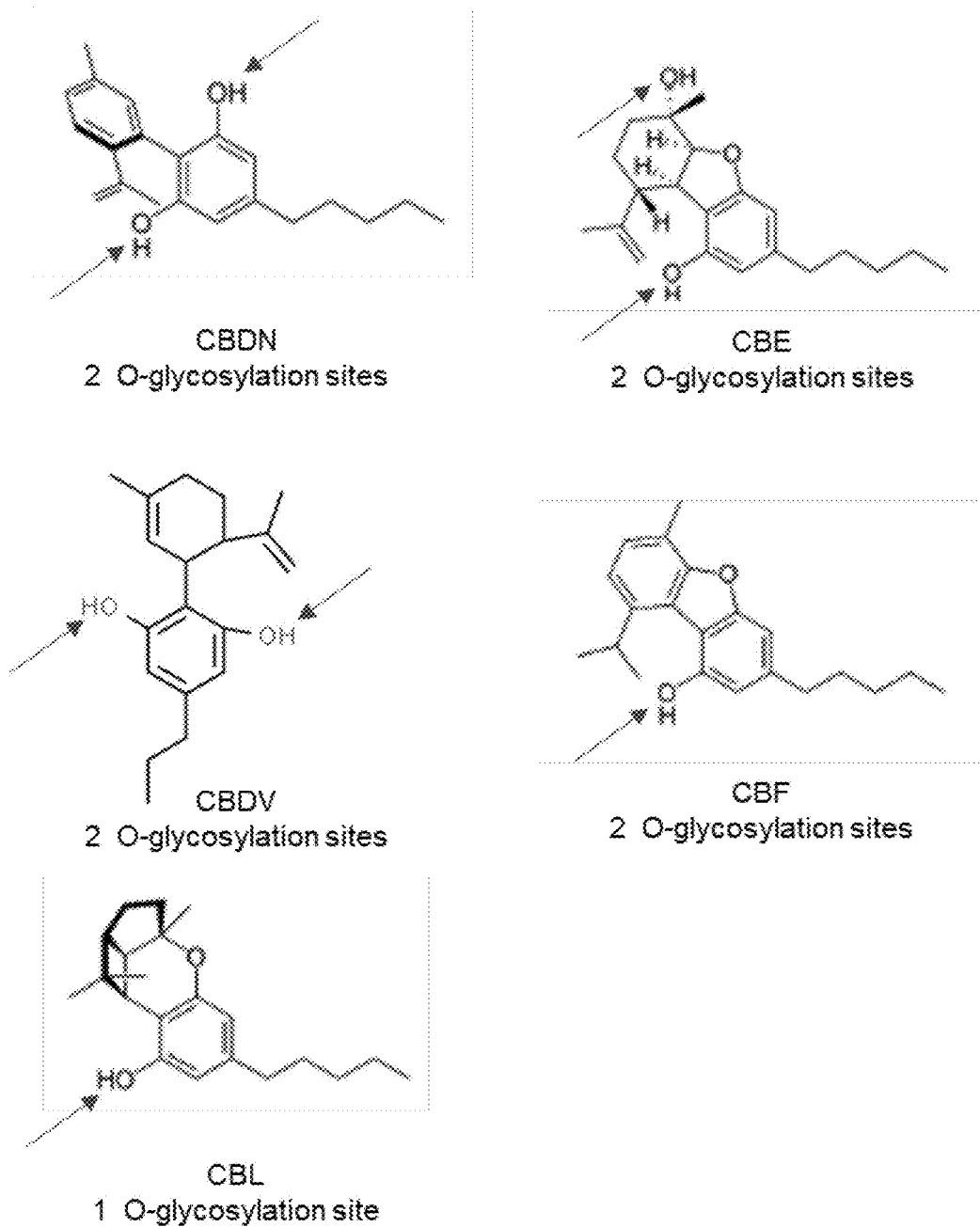

The inventive technology may further include novel cannabinoid compounds as well as their generation in vitro, in vivo, and in vivo. As demonstrated in FIGS. 10 and 11 respectively, the invention includes cannabinoid glycoside compounds identified as: 10B, 10C, 10D, 11A, 11B, 11C, 11D, 11E and 11F and/or a physiologically acceptable salt thereof. In this embodiment, one or more of cannabinoid glycoside compounds identified as: 10B, 10C, 10D, 11A, 11B, 11C, 11D, 11E and 11F, may be generated through the introduction of a UGT selected from the group consisting of the amino acid sequence according to SEQ ID NO. 9181.

In one preferred embodiment, the invention may include a pharmaceutical composition as active ingredient an effective amount or dose of one or more compounds identified as 10B, 10C, 10D, 11A, 11B, 11C, 11D, 11E and 11F and/or a physiologically acceptable salt thereof, wherein the active ingredient is provided together with pharmaceutically tolerable adjuvants and/or excipients in the pharmaceutical composition. Such pharmaceutical composition may optionally be in combination with one or more further active ingredients. In one embodiment, one of the aforementioned compositions may act as a prodrug. The term "prodrug" is taken to mean compounds according to the invention which have been modified by means of, for example, sugars and which are cleaved in the organism to form the effective compounds according to the invention. The terms "effective amount" or "effective dose" or "dose" are interchangeably used herein and denote an amount of the pharmaceutical compound having a prophylactically or therapeutically relevant effect on a disease or pathological conditions, i.e. which causes in a tissue, system, animal or human a biological or medical response which is sought or desired, for example, by a researcher or physician. Pharmaceutical formulations can be administered in the form of dosage units which comprise a predetermined amount of active ingredient per dosage unit. The concentration of the prophylactically or therapeutically active ingredient in the formulation may vary from about 0.1 to 100 wt %. Preferably, the compound of formula (I) or the pharmaceutically acceptable salts thereof are administered in doses of approximately 0.5 to 1000 mg, more preferably between 1 and 700 mg, most preferably 5 and 100 mg per dose unit. Generally, such a dose range is appropriate for total daily incorporation. In other terms, the daily dose is preferably between approximately 0.02 and 100 mg/kg of body weight. The specific dose for each patient depends, however, on a wide variety of factors as already described in the present specification (e.g. depending on the condition treated, the method of administration and the age, weight and condition of the patient). Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

In the meaning of the present invention, the compound is further defined to include pharmaceutically usable derivatives, solvates, prodrugs, tautomers, enantiomers, racemates and stereoisomers thereof, including mixtures thereof in all ratios.

It should be noted that in one embodiment, one or more UGTs may have an affinity for either of the hydroxy groups located at positions 2,4 on the pentylbenzoate/pentlybenzoic ring of a cannabinoid, compound, such a CBDA (2,4-dihydroxy-3-[(6R)-3-methyl-6-(prop-1-en-2-yl) cyclohex-2-en-1-yl]-6-pentylbenzoate) and/or CBGA ((E)-3-(3,7-Dimethyl-2,6-octadienyl)-2,4-dihydroxy-6-pentylbenzoic acid).

As noted above, present invention allows the scaled production of water-soluble cannabinoid glycosides, including acetylated cannabinoid glycosides, as well as acetylated cannabinoids through the introduction of a cannabinoids with a UGT having specific activity towards said cannabinoid, wherein said UGT is selected from the group consisting of: Gram+structural class of UGTs, GT-A structural class of UGTs, GT-B structural class of UGTs, and SEQ ID NO. 1-9181. Because of this enhanced solubility, the invention allows for the addition of such water-soluble cannabinoid to a variety of compositions without requiring oils and or emulsions that are generally required to maintain the non-modified cannabinoids in suspension. As a result, the present invention may all for the production of a variety of compositions for both the food and beverage industry, as well as pharmaceutical applications that do not required oils and emulsion suspensions and the like.

In one embodiment the invention may include aqueous compositions containing one or more water-soluble cannabinoids that may be introduced to a food or beverage. In a preferred embodiment, the invention may include an aqueous solution containing one or more dissolved water-soluble cannabinoids. In this embodiment, such water-soluble cannabinoid may include a glycosylated cannabinoid, and/or an acetylated cannabinoid, and/or a mixture of both. Here, the glycosylated cannabinoid, and/or said acetylated cannabinoid were generated in vivo as generally described herein, or in vitro. In additional embodiment, the water-soluble cannabinoid may be an isolated non-psychoactive, such as CBD and the like. Moreover, in this embodiment, the aqueous may contain one or more of the following: saline, purified water, propylene glycol, deionized water, and/or an alcohol such as ethanol as well as a pH buffer that may allow the aqueous solution to be maintained at a pH below 7.4. Additional embodiments may include the addition an acid of base, such as formic acid, or ammonium hydroxide.

In another embodiment, the invention may include a consumable food additive having at least one water-soluble cannabinoid, such as a glycosylated and/or an acetylated cannabinoid, and/or a mixture of both, where such water-soluble cannabinoids may be generated in vivo and/or in vitro. This consumable food additive may further include one or more a food additive polysaccharides, such as dextrin and/or maltodextrin, as well as an emulsifier. Example emulisifiers may include, but not be limited to: gum arabic, modified starch, pectin, xanthan gum, gum ghatti, gum tragacanth, fenugreek gum, mesquite gum, mono-glycerides and di-glycerides of long chain fatty acids, sucrose monoesters, sorbitan esters, polyethoxylated glycerols, stearic acid, palmitic acid, mono-glycerides, di-glycerides, propylene glycol esters, lecithin, lactylated mono- and di-glycerides, propylene glycol monoesters, polyglycerol esters, diacetylated tartaric acid esters of mono- and di-glycerides, citric acid esters of monoglycerides, stearoyl-2-lactylates, polysorbates, succinylated monoglycerides, acetylated monoglycerides, ethoxylated monoglycerides, *quillaia*, whey protein isolate, casein, soy protein, vegetable protein, pullulan, sodium alginate, guar gum, locust bean gum, tragacanth gum, tamarind gum, carrageenan, furcellaran, Gellan gum, *psyllium*, curdlan, konjac mannan, agar, and cellulose derivatives, or combinations thereof.

The consumable food additive of the invention may be a homogenous composition and may further comprising a flavoring agent. Exemplary flavoring agents may include: sucrose (sugar), glucose, fructose, sorbitol, mannitol, corn syrup, high fructose corn syrup, saccharin, aspartame, sucralose, acesulfame potassium (acesulfame-K), neotame. The consumable food additive of the invention may also contain one or more coloring agents. Exemplary coloring agents may include: FD&C Blue Nos. 1 and 2, FD&C Green No. 3, FD&C Red Nos. 3 and 40, FD&C Yellow Nos. 5 and 6, Orange B, Citrus Red No. 2, annatto extract, beta-carotene, grape skin extract, cochineal extract or carmine, paprika oleoresin, caramel color, fruit and vegetable juices, saffron, Monosodium glutamate (MSG), hydrolyzed soy protein, autolyzed yeast extract, disodium guanylate or inosinate.

The consumable food additive of the invention may also contain one or more surfactants, such as glycerol monostearate and polysorbate 80. The consumable food additive of the invention may also contain one or more preservatives. Exemplary preservatives may include ascorbic acid, citric acid, sodium benzoate, calcium propionate, sodium erythorbate, sodium nitrite, calcium sorbate, potassium sorbate, BHA, BHT, EDTA, tocopherols. The consumable food additive of the invention may also contain one or more nutrient supplements, such as: thiamine hydrochloride, riboflavin, niacin, niacinamide, folate or folic acid, beta carotene, potassium iodide, iron or ferrous sulfate, alpha tocopherols, ascorbic acid, Vitamin D, amino acids, multi-vitamin, fish oil, co-enzyme Q-10, and calcium.

In one embodiment, the invention may include a consumable fluid containing at least one dissolved water-soluble cannabinoid. In one preferred embodiment, this consumable fluid may be added to a drink or beverage to infused it with the dissolved water-soluble cannabinoid generated in an in vivo system as generally herein described, or through an in vitro process, for example as identified by Zipp et al. which is incorporated herein by reference. As noted above, such water-soluble cannabinoid may include a water-soluble glycosylated cannabinoid and/or a water-soluble acetylated cannabinoid, and/or a mixture of both. The consumable fluid may include a food additive polysaccharide such as maltodextrin and/or dextrin, which may further be in an aqueous form and/or solution. For example, in one embodiment, and aqueous maltodextrin solution may include a quantity of sorbic acid and an acidifying agent to provide a food grade aqueous solution of maltodextrin having a pH of 2-4 and a sorbic acid content of 0.02-0.1% by weight.

In certain embodiments, the consumable fluid may include water, as well as an alcoholic beverage; a nonalcoholic beverage, a noncarbonated beverage, a carbonated beverage, a cola, a root beer, a fruit-flavored beverage, a citrus-flavored beverage, a fruit juice, a fruit-containing beverage, a vegetable juice, a vegetable containing beverage, a tea, a coffee, a dairy beverage, a protein containing beverage, a shake, a sports drink, an energy drink, and a flavored water.

The consumable fluid may further include at least one additional ingredients, including but not limited to: xanthan gum, cellulose gum, whey protein hydrolysate, ascorbic acid, citric acid, malic acid, sodium benzoate, sodium citrate, sugar, phosphoric acid, and water.

In one embodiment, the invention may include a consumable gel having at least one water-soluble cannabinoid and gelatin in an aqueous solution. In a preferred embodiment, the consumable gel may include a water-soluble glycosylated cannabinoid and/or a water-soluble acetylated cannabinoid, or a mixture of both, generated in an in vivo system, such as a whole plant or cell suspension culture system as generally herein described.

Additional embodiments may include a liquid composition having at least one water-soluble cannabinoid solubilized in a first quantity of water; and at least one of: xanthan gum, cellulose gum, whey protein hydrolysate, ascorbic acid, citric acid, malic acid, sodium benzoate, sodium citrate, sugar, phosphoric acid, and/or a sugar alcohol. In this embodiment, a water-soluble cannabinoid may include a glycosylated water-soluble cannabinoid, an acetylated water-soluble cannabinoid, or a mixture of both. In one preferred embodiment, the composition may further include a quantity of ethanol. Here, the amount of water-soluble cannabinoid may include: less than 10 mass % water; more than 95 mass % water; about 0.1 mg to about 1000 mg of the water-soluble cannabinoid; about 0.1 mg to about 500 mg of the water-soluble cannabinoid; about 0.1 mg to about 200 mg of the water-soluble cannabinoid; about 0.1 mg to about 100 mg of the water-soluble cannabinoid; about 0.1 mg to about 100 mg of the water-soluble cannabinoid; about 0.1 mg to about 10 mg of the water-soluble cannabinoid; about 0.5 mg to about 5 mg of the water-soluble cannabinoid; about 1 mg/kg to 5 mg/kg (body weight) in a human of the water-soluble cannabinoid.

In alternative embodiment, the composition may include at least one water-soluble cannabinoid in the range of 50 mg/L to 300 mg/L; at least one water-soluble cannabinoid in the range of 50 mg/L to 100 mg/L; at least one water-soluble cannabinoid in the range of 50 mg/L to 500 mg/L; at least one water-soluble cannabinoid over 500 mg/L; at least one water-soluble cannabinoid under 50 mg/L. Additional embodiments may include one or more of the following additional components: a flavoring agent; a coloring agent; a coloring agent; and/or caffeine.

In one embodiment, the invention may include a liquid composition having at least one water-soluble cannabinoid solubilized in said first quantity of water and a first quantity of ethanol in a liquid state. In a preferred embodiment, a first quantity of ethanol in a liquid state may be between 1% to 20% weight by volume of the liquid composition. In this embodiment, a water-soluble cannabinoid may include a glycosylated water-soluble cannabinoid, an acetylated water-soluble cannabinoid, or a mixture of both. Such water-soluble cannabinoids may be generated in an in vivo and/or in vitro system as herein identified. In a preferred embodiment, the ethanol, or ethyl alcohol component may be up to about ninety-nine point nine-five percent (99.95%) by weight and the water-soluble cannabinoid about zero point zero five percent (0.05%) by weight. In another embodiment, Examples of the preferred embodiment may include liquid ethyl alcohol compositions having one or more water-soluble cannabinoids wherein said ethyl alcohol has a proof greater than 100, and/or less than 100. Additional examples of a liquid composition containing ethyl alcohol and at least one water-soluble cannabinoid may include, beer, wine and/or distilled spirit.

Additional embodiments of the invention may include a chewing gum composition having a first quantity of at least one water-soluble cannabinoid. In a preferred embodiment, a chewing gum composition may further include a gum base comprising a buffering agent selected from the group consisting of acetates, glycinates, phosphates, carbonates, glycerophosphates, citrates, borates, and mixtures thereof. Additional components may include at least one sweetening agent; and at least one flavoring agent. As noted above, in a preferred embodiment, a water-soluble cannabinoid may include at least one water-soluble acetylated cannabinoid, and/or at least one water-soluble glycosylated cannabinoid, or a mixture of the two. In this embodiment, such water soluble glycosylated cannabinoid, and/or said acetylated cannabinoid may have been glycosylated and/or acetylated in vivo respectively.

In one embodiment, the chewing gum composition described above may include:
  0.01 to 1% by weight of at least one water-soluble cannabinoid;
  25 to 85% by weight of a gum base;
  10 to 35% by weight of at least one sweetening agent; and
  1 to 10% by weight of a flavoring agent.

Here, such flavoring agents may include: menthol flavor, *eucalyptus*, mint flavor and/or L-menthol. Sweetening agents may include one or more of the following: xylitol, sorbitol, isomalt, aspartame, sucralose, acesulfame potassium, and saccharin. Additional preferred embodiment may include a chewing gum having a pharmaceutically acceptable excipient selected from the group consisting of: fillers, disintegrants, binders, lubricants, and antioxidants. The chewing gum composition may further be non-disintegrating and also include one or more coloring and/or flavoring agents.

The invention may further include a composition for a water-soluble cannabinoid infused solution comprising essentially of: water and/or purified water, at least one water-soluble cannabinoid, and at least one flavoring agent. A water-soluble cannabinoid infused solution of the invention may further include a sweetener selected from the group consisting of: glucose, sucrose, invert sugar, corn syrup, *stevia* extract powder, stevioside, steviol, aspartame, saccharin, saccharin salts, sucralose, potassium acetosulfam, sorbitol, xylitol, mannitol, erythritol, lactitol, alitame, miraculin, monellin, and thaumatin or a combination of the same. Additional components of the water-soluble cannabinoid infused solution may include, but not be limited to: sodium chloride, sodium chloride solution, glycerin, a coloring agent, and a demulcent. As to this last potential component, in certain embodiment, a demulcent may include: pectin, glycerin, honey, methylcellulose, and/or propylene glycol. As noted above, in a preferred embodiment, a water-soluble cannabinoid may include at least one water-soluble acetylated cannabinoid, and/or at least one water-soluble glycosylated cannabinoid, or a mixture of the two. In this embodiment, such water soluble glycosylated cannabinoid, and/or said acetylated cannabinoid may have been glycosylated and/or acetylated in vivo respectively.

The invention may further include a composition for a water-soluble cannabinoid infused anesthetic solution having water, or purified water, at least one water-soluble cannabinoid, and at least one oral anesthetic. In a preferred embodiment, an anesthetic may include benzocaine, and/or phenol in a quantity of between 0.1% to 15% volume by weight.

Additional embodiments may include a water-soluble cannabinoid infused anesthetic solution having a sweetener which may be selected from the group consisting of: glucose, sucrose, invert sugar, corn syrup, *stevia* extract powder, stevioside, steviol, aspartame, saccharin, saccharin salts, sucralose, potassium acetosulfam, sorbitol, xylitol, mannitol, erythritol, lactitol, alitame, miraculin, monellin, and thaumatin or a combination of the same. Additional components of the water-soluble cannabinoid infused solution may include, but not be limited to: sodium chloride, sodium chloride solution, glycerin, a coloring agent a demulcent. In a preferred embodiment, a demulcent may be selected from the group consisting of: pectin, glycerin, honey, methylcellulose, and propylene glycol. As noted above, in a preferred embodiment, a water-soluble cannabinoid may include at least one water-soluble acetylated cannabinoid, and/or at least one water-soluble glycosylated cannabinoid, or a mixture of the two. In this embodiment, such water soluble glycosylated cannabinoid, and/or said acetylated cannabinoid may have been glycosylated and/or acetylated in vivo respectively.

The invention may further include a composition for a hard lozenge for rapid delivery of water-soluble cannabinoids through the oral mucosa. In this embodiment, such a hard lozenge composition may include: a crystalized sugar base, and at least one water-soluble cannabinoid, wherein the hard lozenge has a moisture content between 0.1 to 2%. In this embodiment, the water-soluble cannabinoid may be added to the sugar based when it is in a liquefied form and prior to the evaporation of the majority of water content. Such a hard lozenge may further be referred to as a candy.

In a preferred embodiment, a crystalized sugar base may be formed from one or more of the following: sucrose, invert sugar, corn syrup, and isomalt or a combination of the same. Additional components may include at least one acidulant. Examples of acidulants may include, but not be limited to: citric acid, tartaric acid, fumaric acid, and malic acid. Additional components may include at least one pH adjustor. Examples of pH adjustors may include, but not be limited to: calcium carbonate, sodium bicarbonate, and magnesium trisilicate.

In another preferred embodiment, the composition may include at least one anesthetic. Example of such anesthetics may include benzocaine, and phenol. In this embodiment, first quantity of anesthetic may be between 1 mg to 15 mg per lozenge. Additional embodiments may include a quantity of menthol. In this embodiment, such a quantity of menthol may be between 1 mg to 20 mg. The hard lozenge composition may also include a demulcent, for example: pectin, glycerin, honey, methylcellulose, propylene glycol, and glycerin. In this embodiment, a demulcent may be in a quantity between 1 mg to 10 mg. As noted above, in a preferred embodiment, a water-soluble cannabinoid may include at least one water-soluble acetylated cannabinoid, and/or at least one water-soluble glycosylated cannabinoid, or a mixture of the two. In this embodiment, such water soluble glycosylated cannabinoid, and/or said acetylated cannabinoid may have been glycosylated and/or acetylated in vivo respectively.

The invention may include a chewable lozenge for rapid delivery of water-soluble cannabinoids through the oral mucosa. In a preferred embodiment, the compositions may include: a glycerinated gelatin base, at least one sweetener; and at least one water-soluble cannabinoid dissolved in a first quantity of water. In this embodiment, a sweetener may include sweetener selected from the group consisting of: glucose, sucrose, invert sugar, corn syrup, *stevia* extract powder, stevioside, steviol, aspartame, saccharin, saccharin salts, sucralose, potassium acetosulfam, sorbitol, xylitol, mannitol, erythritol, lactitol, alitame, miraculin, monellin, and thaumatin or a combination of the same.

Additional components may include at least one acidulant. Examples of acidulants may include, but not be limited to: citric acid, tartaric acid, fumaric acid, and malic acid. Additional components may include at least one pH adjustor. Examples of pH adjustors may include, but not be limited to: calcium carbonate, sodium bicarbonate, and magnesium trisilicate.

In another preferred embodiment, the composition may include at least one anesthetic. Example of such anesthetics may include benzocaine, and phenol. In this embodiment, first quantity of anesthetic may be between 1 mg to 15 mg per lozenge. Additional embodiments may include a quantity of menthol. In this embodiment, such a quantity of menthol may be between 1 mg to 20 mg. The chewable lozenge composition may also include a demulcent, for example: pectin, glycerin, honey, methylcellulose, propylene glycol, and glycerin. In this embodiment, a demulcent may be in a quantity between 1 mg to 10 mg. As noted above, in a preferred embodiment, a water-soluble cannabinoid may include at least one water-soluble acetylated cannabinoid, and/or at least one water-soluble glycosylated cannabinoid, or a mixture of the two. In this embodiment, such water soluble glycosylated cannabinoid, and/or said acetylated cannabinoid may have been glycosylated and/or acetylated in vivo respectively.

The invention may include a soft lozenge for rapid delivery of water-soluble cannabinoids through the oral mucosa. In a preferred embodiment, the compositions may include: polyethylene glycol base, at least one sweetener; and at least one water-soluble cannabinoid dissolved in a first quantity of water. In this embodiment, a sweetener may include sweetener selected from the group consisting of: glucose, sucrose, invert sugar, corn syrup, *stevia* extract powder, stevioside, steviol, aspartame, saccharin, saccharin salts, sucralose, potassium acetosulfam, sorbitol, xylitol, mannitol, erythritol, lactitol, alitame, miraculin, monellin, and thaumatin or a combination of the same. Additional components may include at least one acidulant. Examples of acidulants may include, but not be limited to: citric acid, tartaric acid, fumaric acid, and malic acid. Additional components may include at least one pH adjustor. Examples of pH adjustors may include, but not be limited to: calcium carbonate, sodium bicarbonate, and magnesium trisilicate.

In another preferred embodiment, the composition may include at least one anesthetic. Example of such anesthetics may include benzocaine, and phenol. In this embodiment, first quantity of anesthetic may be between 1 mg to 15 mg per lozenge. Additional embodiments may include a quantity of menthol. In this embodiment, such a quantity of menthol may be between 1 mg to 20 mg. The soft lozenge composition may also include a demulcent, for example: pectin, glycerin, honey, methylcellulose, propylene glycol, and glycerin. In this embodiment, a demulcent may be in a quantity between 1 mg to 10 mg. As noted above, in a preferred embodiment, a water-soluble cannabinoid may include at least one water-soluble acetylated cannabinoid, and/or at least one water-soluble glycosylated cannabinoid, or a mixture of the two. In this embodiment, such water soluble glycosylated cannabinoid, and/or said acetylated cannabinoid may have been glycosylated and/or acetylated in vivo respectively.

In another embodiment, the invention may include a tablet or capsule consisting essentially of a water-soluble glycosylated cannabinoid and a pharmaceutically acceptable excipient. Example may include solid, semi-solid and aqueous excipients such as: maltodextrin, whey protein isolate, xanthan gum, guar gum, diglycerides, monoglycerides, carboxymethyl cellulose, glycerin, gelatin, polyethylene glycol and water-based excipients.

In a preferred embodiment, a water-soluble cannabinoid may include at least one water-soluble acetylated cannabinoid, and/or at least one water-soluble glycosylated cannabinoid, or a mixture of the two. In this embodiment, such water soluble glycosylated cannabinoid, and/or said acetylated cannabinoid may have been glycosylated and/or acetylated in vivo respectively. Examples of such in vivo systems being generally described herein, including in plant, as well as cell culture systems including *cannabis* cell culture, tobacco cell culture and yeast cell culture systems. In one embodiment, a tablet or capsule may include an amount of water-soluble cannabinoid of 5 milligrams or less. Alternative embodiments may include an amount of water-soluble cannabinoid between 5 milligrams and 200 milligrams. Still other embodiments may include a tablet or capsule having amount of water-soluble cannabinoid that is more than 200 milligrams.

The invention may further include a method of manufacturing and packaging a cannabinoid dosage, consisting of the following steps: 1) preparing a fill solution with a desired concentration of a water-soluble cannabinoid in a liquid carrier wherein said cannabinoid solubilized in said liquid carrier; 2) encapsulating said fill solution in capsules; 3) packaging said capsules in a closed packaging system; and 4) removing atmospheric air from the capsules. In one embodiment, the step of removing of atmospheric air consists of purging the packaging system with an inert gas, such as, for example, nitrogen gas, such that said packaging system provides a room temperature stable product. In one preferred embodiment, the packaging system may include a plaster package, which may be constructed of material that minimizes exposure to moisture and air.

In one embodiment a preferred liquid carrier may include a water-based carrier, such as for example an aqueous sodium chloride solution. In a preferred embodiment, a water-soluble cannabinoid may include at least one water-soluble acetylated cannabinoid, and/or at least one water-soluble glycosylated cannabinoid, or a mixture of the two. In this embodiment, such water soluble glycosylated cannabinoid, and/or said acetylated cannabinoid may have been glycosylated and/or acetylated in vivo respectively. Examples of such in vivo systems being generally described herein, including in plant, as well as cell culture systems including *cannabis* cell culture, tobacco cell culture and yeast cell culture systems. In one embodiment, a desired cannabinoid concentration may be about 1-10% w/w, while in other embodiments it may be about 1.5-6.5% w/w. Alternative embodiments may include an amount of water-soluble cannabinoid between 5 milligrams and 200 milligrams. Still other embodiments may include a tablet or capsule having amount of water-soluble cannabinoid that is more than 200 milligrams.

The invention may include an oral pharmaceutical solution, such as a sub-lingual spray, consisting essentially of a water-soluble cannabinoid, 30-33% w/w water, about 50% w/w alcohol, 0.01% w/w butylated hydroxylanisole (BHA) or 0.1% w/w ethylenediaminetetraacetic acid (EDTA) and 5-21% w/w co-solvent, having a combined total of 100%, wherein said co-solvent is selected from the group consisting of propylene glycol, polyethylene glycol and combinations thereof, and wherein said water-soluble cannabinoid is a glycosylated cannabinoid, an acetylated cannabinoid or a mixture of the two. In an alternative embodiment, such an oral pharmaceutical solution may consist essentially of 0.1 to 5% w/w of said water-soluble cannabinoid, about 50% w/w alcohol, 5.5% w/w propylene glycol, 12% w/w polyethylene glycol and 30-33% w/w water. In a preferred composition, the alcohol component may be ethanol.

The invention may include an oral pharmaceutical solution, such as a sublingual spray, consisting essentially of about 0.1% to 1% w/w water-soluble cannabinoid, about 50% w/w alcohol, 5.5% w/w propylene glycol, 12% w/w polyethylene glycol, 30-33% w/w water, 0.01% w/w butylated hydroxyanisole, having a combined total of 100%, and wherein said water-soluble cannabinoid is a glycosylated cannabinoid, an acetylated cannabinoid or a mixture of the two wherein that were generated in vivo. In an alternative embodiment, such an oral pharmaceutical solution may consist essentially of 0.54% w/w water-soluble cannabinoid, 31.9% w/w water, 12% w/w polyethylene glycol 400, 5.5% w/w propylene glycol, 0.01% w/w butylated hydroxyanisole, 0.05% w/w sucralose, and 50% w/w alcohol, wherein the a the alcohol components may be ethanol.

The invention may include a solution for nasal and/or sublingual administration of a cannabinoid including: 1) an excipient of propylene glycol, ethanol anhydrous, or a mixture of both; and 2) a water-soluble cannabinoid which may include glycosylated cannabinoid an acetylated cannabinoid or a mixture of the two generated in vivo and/or in vitro. In a preferred embodiment, the composition may further include a topical decongestant, which may include phenylephrine hydrochloride, Oxymetazoline hydrochloride, and Xylometazoline in certain preferred embodiments. The composition may further include an antihistamine, and/or a steroid. Preferably, the steroid component is a corticosteroid selected from the group consisting of: neclomethasone dipropionate, budesonide, ciclesonide, flunisolide, fluticasone furoate, fluticasone propionate, mometasone, triamcinolone acetonide. In alternative embodiment, the solution for nasal and/or sublingual administration of a cannabinoid may further comprise at least one of the following: benzalkonium chloride solution, benzyl alcohol, boric acid, purified water, sodium borate, polysorbate 80, phenylethyl alcohol, microcrystalline cellulose, carboxymethylcellulose sodium, dextrose, dipasic, sodium phosphate, edetate disodium, monobasic sodium phosphate, propylene glycol.

The invention may further include an aqueous solution for nasal and/or sublingual administration of a cannabinoid comprising: a water and/or saline solution; and a water-soluble cannabinoid which may include a glycosylated cannabinoid, an acetylated cannabinoid or a mixture of the two generated in vivo and/or in vitro. In a preferred embodiment, the composition may further include a topical decongestant, which may include phenylephrine hydrochloride, Oxymetazoline hydrochloride, and Xylometazoline in certain preferred embodiments. The composition may further include an antihistamine, and/or a steroid. Preferably, the steroid component is a corticosteroid selected from the group consisting of: neclomethasone dipropionate, budesonide, ciclesonide, flunisolide, fluticasone furoate, fluticasone propionate, mometasone, triamcinolone acetonide. In alternative embodiment, the aqueous solution may further comprise at least one of the following: benzalkonium chloride solution, benzyl alcohol, boric acid, purified water, sodium borate, polysorbate 80, phenylethyl alcohol, microcrystalline cellulose, carboxymethylcellulose sodium, dextrose, dipasic, sodium phosphate, edetate disodium, monobasic sodium phosphate, propylene glycol.

The invention may include a topical formulation for the transdermal delivery of water-soluble cannabinoid. In a preferred embodiment, a topical formulation for the transdermal delivery of water-soluble cannabinoid may include a water-soluble glycosylated cannabinoid, and/or water-soluble acetylated cannabinoid, or a mixture of both, and a pharmaceutically acceptable excipient. Here, a glycosylated cannabinoid and/or acetylated cannabinoid may be generated in vivo and/or in vitro. Preferably a pharmaceutically acceptable excipient may include one or more: gels, ointments, cataplasms, poultices, pastes, creams, lotions, plasters and jellies or even polyethylene glycol. Additional embodiments may further include one or more of the following components: a quantity of capsaicin; a quantity of benzocaine; a quantity of lidocaine; a quantity of camphor; a quantity of benzoin resin; a quantity of methylsalicilate; a quantity of triethanolamine salicylate; a quantity of hydrocortisone; a quantity of salicylic acid.

The invention may include a gel for transdermal administration of a water soluble-cannabinoid which may be generated in vitro and/or in vivo. In this embodiment, the mixture preferably contains from 15% to about 90% ethanol, about 10% to about 60% buffered aqueous solution or water, about 0.1 to about 25% propylene glycol, from about 0.1 to about 20% of a gelling agent, from about 0.1 to about 20% of a base, from about 0.1 to about 20% of an absorption enhancer and from about 1% to about 25% polyethylene glycol and a water-soluble cannabinoid such as a glycosylated cannabinoid, and/or acetylated cannabinoid, and/or a mixture of the two.

In another embodiment, the invention may further include a transdermal composition having a pharmaceutically effective amount of a water-soluble cannabinoid for delivery of the cannabinoid to the bloodstream of a user. This transdermal composition may include a pharmaceutically acceptable excipient and at least one water-soluble cannabinoid, such as a glycosylated cannabinoid, an acetylated cannabinoid, and a mixture of both, wherein the cannabinoid is capable of diffusing from the composition into the bloodstream of the user. In a preferred embodiment, a pharmaceutically acceptable excipient to create a transdermal dosage form selected from the group consisting of: gels, ointments, cataplasms, poultices, pastes, creams, lotions, plasters and jellies. The transdermal composition may further include one or more surfactants. In one preferred embodiment, the surfactant may include a surfactant-lecithin organogel, which may further be present in an amount of between about between about 95% and about 98% w/w. In an alternative embodiment, a surfactant-lecithin organogel comprises lecithin and PPG-2 myristyl ether propionate and/or high molecular weight polyacrylic acid polymers. The transdermal composition may further include a quantity of isopropyl myristate.

The invention may further include transdermal composition having one or more permeation enhancers to facilitate transfer of the water-soluble cannabinoid across a dermal layer. In a preferred embodiment, a permeation enhancer may include one or more of the following: propylene glycol monolaurate, diethylene glycol monoethyl ether, an oleoyl macrogolglyceride, a caprylocaproyl macrogolglyceride, and an oleyl alcohol, The invention may also include a liquid cannabinoid liniment composition consisting of water, isopropyl alcohol solution and a water-soluble cannabinoid, such as glycosylated cannabinoid, and/or said acetylated cannabinoid which may further have been generated in vivo. This liquid cannabinoid liniment composition may further include approximately 97.5% to about 99.5% by weight of 70% isopropyl alcohol solution and from about 0.5% to about 2.5% by weight of a water-soluble cannabinoid mixture.

Based on the improved solubility and other physical properties, as well as cost advantage and scalability of the invention's in vivo water-soluble production platform, the invention may include one or more commercial infusions. For example, commercially available products, such a lip balm, soap, shampoos, lotions, creams and cosmetics may be infused with one or more water-soluble cannabinoids.

As generally described herein, the invention may include one or more plants, such as a tobacco plant and/or cell culture that may be genetically modified to produce, for example water-soluble glycosylated cannabinoids in vivo. As such, in one preferred embodiment, the invention may include a tobacco plant and or cell that contain at least one water-soluble cannabinoid. In a preferred embodiment, a tobacco plant containing a quantity of water-soluble cannabinoids may be used to generate a water-soluble cannabinoid infused tobacco product such as a cigarette, pipe tobacco, chewing tobacco, cigar, and smokeless tobacco. In one embodiment, the tobacco plant may be treated with one or more glycosidase inhibitors. In a preferred embodiment, since the cannabinoid being introduced to the tobacco plant may be controlled, the inventive tobacco plant may generate one or more selected water-cannabinoids. For example, in one embodiment, the genetically modified tobacco plant may be introduced to a single cannabinoid, such as a non-psychoactive CBD compound, while in other embodiment, the genetically modified tobacco plant may be introduced to a cannabinoid extract containing a full and/or partial entourage of cannabinoid compounds.

The invention may further include a novel composition that may be used to supplement a cigarette, or other tobacco-based product. In this embodiment, the composition may include at least one water-soluble cannabinoid dissolved in an aqueous solution. This aqueous solution may be wherein said composition may be introduced to a tobacco product, such as a cigarette and/or a tobacco leaf such that the aqueous solution may evaporate generating a cigarette and/or a tobacco leaf that contains the aforementioned water-soluble cannabinoid(s), which may further have been generated in vivo as generally described herein.

On one embodiment the invention may include one or more method of treating a medical condition in a mammal. In this embodiment, the novel method may include of administering a therapeutically effective amount of a water-soluble cannabinoid, such as an in vivo generated glycosylated cannabinoid, and/or an acetylated cannabinoid, and/or a mixture of both or a pharmaceutically acceptable salt thereof, wherein the medical condition is selected from the group consisting of: obesity, post-traumatic stress syndrome, anorexia, nausea, emesis, pain, wasting syndrome, HIV-wasting, chemotherapy induced nausea and vomiting, alcohol use disorders, anti-tumor, amyotrophic lateral sclerosis, glioblastoma multiforme, glioma, increased intraocular pressure, glaucoma, *cannabis* use disorders, Tourette's syndrome, dystonia, multiple sclerosis, inflammatory bowel disorders, arthritis, dermatitis, Rheumatoid arthritis, systemic lupus erythematosus, anti-inflammatory, anti-convulsant, anti-psychotic, anti-oxidant, neuroprotective, anti-cancer, immunomodulatory effects, peripheral neuropathic pain, neuropathic pain associated with post-herpetic neuralgia, diabetic neuropathy, shingles, burns, actinic keratosis, oral cavity sores and ulcers, post-episiotomy pain, psoriasis, pruritis, contact dermatitis, eczema, bullous dermatitis herpetiformis, exfoliative dermatitis, mycosis fungoides, pemphigus, severe erythema multiforme (e.g., Stevens-Johnson syndrome), seborrheic dermatitis, ankylosing spondylitis, psoriatic arthritis, Reiter's syndrome, gout, chondrocalcinosis, joint pain secondary to dysmenorrhea, fibromyalgia, musculoskeletal pain, neuropathic-postoperative complications, polymyositis, acute nonspecific tenosynovitis, bursitis, epicondylitis, post-traumatic osteoarthritis, synovitis, and juvenile rheumatoid arthritis. In a preferred embodiment, the pharmaceutical composition may be administered by a route selected from the group consisting of: transdermal, topical, oral, buccal, sublingual, intra-venous, intra-muscular, vaginal, rectal, ocular, nasal and follicular. The number of water-soluble cannabinoids may be a therapeutically effective amount, which may be determined by the patient's age, weight, medical condition cannabinoid-delivered, route of delivery and the like. In one embodiment, a therapeutically effective amount may be 50 mg or less of a water-soluble cannabinoid. In another embodiment, a therapeutically effective amount may be 50 mg or more of a water-soluble cannabinoid.

It should be noted that for any of the above composition, unless otherwise stated, an effective amount of water-soluble cannabinoids may include amounts between: 0.01 mg to 0.1 mg; 0.01 mg to 0.5 mg; 0.01 mg to 1 mg; 0.01 mg to 5 mg; 0.01 mg to 10 mg; 0.01 mg to 25 mg; 0.01 mg to 50 mg; 0.01 mg to 75 mg; 0.01 mg to 100 mg; 0.01 mg to 125 mg; 0.01 mg to 150 mg; 0.01 mg to 175 mg; 0.01 mg to 200 mg; 0.01 mg to 225 mg; 0.01 mg to 250 mg; 0.01 mg to 275 mg; 0.01 mg to 300 mg; 0.01 mg to 225 mg; 0.01 mg to 350 mg; 0.01 mg to 375 mg; 0.01 mg to 400 mg; 0.01 mg to 425 mg; 0.01 mg to 450 mg; 0.01 mg to 475 mg; 0.01 mg to 500 mg; 0.01 mg to 525 mg; 0.01 mg to 550 mg; 0.01 mg to 575 mg; 0.01 mg to 600 mg; 0.01 mg to 625 mg; 0.01 mg to 650 mg; 0.01 mg to 675 mg; 0.01 mg to 700 mg; 0.01 mg to 725 mg; 0.01 mg to 750 mg; 0.01 mg to 775 mg; 0.01 mg to 800 mg; 0.01 mg to 825 mg; 0.01 mg to 950 mg; 0.01 mg to 875 mg; 0.01 mg to 900 mg; 0.01 mg to 925 mg; 0.01 mg to 950 mg; 0.01 mg to 975 mg; 0.01 mg to 1000 mg; 0.01 mg to 2000 mg; 0.01 mg to 3000 mg; 0.01 mg to 4000 mg; 01 mg to 5000 mg; 0.01 mg to. 1 mg/kg.; 0.01 mg to 0.5 mg/kg; 01 mg to 1 mg/kg; 0.01 mg to 5 mg/kg; 0.01 mg to 10 mg/kg; 0.01 mg to 25 mg/kg; 0.01 mg to 50 mg/kg; 0.01 mg to 75 mg/kg; and 0.01 mg to 100 mg/kg.

The modified cannabinoids compounds of the present invention are useful for a variety of therapeutic applications. For example, the compounds are useful for treating or alleviating symptoms of diseases and disorders involving CB1 and CB2 receptors, including appetite loss, nausea and vomiting, pain, multiple sclerosis and epilepsy. For example, they may be used to treat pain (i.e. as analgesics) in a variety of applications including but not limited to pain management. In additional embodiments, such modified cannabinoids compounds may be used as an appetite suppressant. Additional embodiment may include administering the modified cannabinoids compounds.

By "treating" the present inventors mean that the compound is administered in order to alleviate symptoms of the disease or disorder being treated. Those of skill in the art will recognize that the symptoms of the disease or disorder that is treated may be completely eliminated or may simply be lessened. Further, the compounds may be administered in combination with other drugs or treatment modalities, such as with chemotherapy or other cancer-fighting drugs.

Implementation may generally involve identifying patients suffering from the indicated disorders and administering the compounds of the present invention in an acceptable form by an appropriate route. The exact dosage to be administered may vary depending on the age, gender, weight and overall health status of the individual patient, as well as the precise etiology of the disease. However, in general, for administration in mammals (e.g. humans), dosages in the range of from about 0.01 to about 300 mg of compound per kg of body weight per 24 hr., and more preferably about 0.01 to about 100 mg of compound per kg of body weight per 24 hr., are effective.

Administration may be oral or parenteral, including intravenously, intramuscularly, subcutaneously, intradermal injection, intraperitoneal injection, etc., or by other routes (e.g. transdermal, sublingual, oral, rectal and buccal delivery, inhalation of an aerosol, etc.). In a preferred embodiment of the invention, the water-soluble cannabinoid analogs are provided orally or intravenously.

In particular, the phenolic esters of the invention are preferentially administered systemically in order to afford an opportunity for metabolic activation via in vivo cleavage of the ester. In addition, the water soluble compounds with azole moieties at the pentyl side chain do not require in vivo activation and may be suitable for direct administration (e.g. site specific injection).

The compounds may be administered in the pure form or in a pharmaceutically acceptable formulation including suitable elixirs, binders, and the like (generally referred to a "carriers") or as pharmaceutically acceptable salts (e.g. alkali metal salts such as sodium, potassium, calcium or lithium salts, ammonium, etc.) or other complexes. It should be understood that the pharmaceutically acceptable formulations include liquid and solid materials conventionally utilized to prepare both injectable dosage forms and solid dosage forms such as tablets and capsules and aerosolized dosage forms. In addition, the compounds may be formulated with aqueous or oil based vehicles. Water may be used as the carrier for the preparation of compositions (e.g. injectable compositions), which may also include conventional buffers and agents to render the composition isotonic. Other potential additives and other materials (preferably those which are generally regarded as safe [GRAS]) include: colorants; flavorings; surfactants (TWEEN, oleic acid, etc.); solvents, stabilizers, elixirs, and binders or encapsulants (lactose, liposomes, etc.). Solid diluents and excipients include lactose, starch, conventional disintegrating agents, coatings and the like. Preservatives such as methyl paraben or benzalkium chloride may also be used. Depending on the formulation, it is expected that the active composition will consist of about 1% to about 99% of the composition and the vehicular "carrier" will constitute about 1% to about 99% of the composition. The pharmaceutical compositions of the present invention may include any suitable pharmaceutically acceptable additives or adjuncts to the extent that they do not hinder or interfere with the therapeutic effect of the active compound.

The administration of the compounds of the present invention may be intermittent, bolus dose, or at a gradual or continuous, constant or controlled rate to a patient. In addition, the time of day and the number of times per day that the pharmaceutical formulation is administered may vary are and best determined by a skilled practitioner such as a physician. Further, the effective dose can vary depending upon factors such as the mode of delivery, gender, age, and other conditions of the patient, as well as the extent or progression of the disease. The compounds may be provided alone, in a mixture containing two or more of the compounds, or in combination with other medications or treatment modalities. The compounds may also be added to blood ex vivo and then be provided to the patient.

Genes encoding by a combination polynucleotide and/or a homologue thereof, may be introduced into a plant, and/or plant cell using several types of transformation approaches developed for the generation of transgenic plants. Standard transformation techniques, such as Ti-plasmid *Agrobacterium*-mediated transformation, particle bombardment, microinjection, and electroporation may be utilized to construct stably transformed transgenic plants. Examples of stably transformed yeast may be described in Sayre et al. PCT/US18/41710, such techniques for yeast transformation being specifically incorporated herein by reference. Examples of stably transformed plants, such as *Cannabis* plants, may be described by Sayre et al. 62/885,349, such techniques for stable *Cannabis* transformation being specifically incorporated herein by reference)

As used herein, a "cannabinoid" is a chemical compound (such as cannabinol, THC or cannabidiol) that is found in the plant species *Cannabis* among others like: *Echinacea; Acmella Oleracea; Helichrysum Umbraculigerum; Radula marginata* (Liverwort) and *Theobroma cacao*, and metabolites and synthetic analogues thereof that may or may not have psychoactive properties. Cannabinoids therefore include (without limitation) compounds (such as THC) that have high affinity for the cannabinoid receptor (for example Ki<250 nM), and compounds that do not have significant affinity for the cannabinoid receptor (such as cannabidiol, CBD). Cannabinoids also include compounds that have a characteristic dibenzopyran ring structure (of the type seen in THC) and cannabinoids which do not possess a pyran ring (such as cannabidiol). Hence a partial list of cannabinoids includes THC, CBD, dimethyl heptylpentyl cannabidiol (DMHP-CBD), 6,12-dihydro-6-hydroxy-cannabidiol (described in U.S. Pat. No. 5,227,537, incorporated by reference); (3S,4R)-7-hydroxy-46-tetrahydrocannabinol homologs and derivatives described in U.S. Pat. No. 4,876, 276, incorporated by reference; (+)-4-[4-DMH-2,6-diacetoxy-phenyl]-2-carboxy-6,6-dimethylbicyclo[3.1.1]hept-2-en, and other 4-phenylpinene derivatives disclosed in U.S. Pat. No. 5,434,295, which is incorporated by reference; and cannabidiol (−)(CBD) analogs such as (−)CBD-monomethylether, (−)CBD dimethyl ether; (−)CBD diacetate; (−)3'-acetyl-CBD monoacetate; and ±AF11, all of which are disclosed in Consroe et al., J. Clin. Phannacol. 21: 428S-436S, 1981, which is also incorporated by reference. Many other cannabinoids are similarly disclosed in Agurell et al., Pharmacol. Rev. 38:31-43, 1986, which is also incorporated by reference.

Examples of cannabinoids are tetrahydrocannabinol, cannabidiol, cannabigerol, cannabichromene, cannabicyclol, cannabivarin, cannabielsoin, cannabicitran, cannabigerolic acid, cannabigerolic acid monomethylether, cannabigerol monomethylether, cannabigerovarinic acid, cannabigerovarin, cannabichromenic acid, cannabichromevarinic acid, cannabichromevarin, cannabidolic acid, cannabidiol monomethylether, cannabidiol-C4, cannabidivarinic acid, cannabidiorcol, delta-9-tetrahydrocannabinolic acid A, delta-9-tetrahydrocannabinolic acid B, delta-9-tetrahydrocannabinolic acid-C4, delta-9-tetrahydrocannabivarinic acid,delta-9-tetrahydrocannabivarin, delta-9-tetrahydrocannabiorcolic acid, delta-9-tetrahydrocannabiorcol,delta-7-cis-iso-tetrahydrocannabivarin, delta-8-tetrahydrocannabiniolic acid, delta-8-tetrahydrocannabinol, cannabicyclolic acid, cannabicylovarin, cannabielsoic acid A, cannabielsoic acid B, cannabinolic acid, cannabinol methylether, cannabinol-C4, cannabinol-C2, cannabiorcol, 10-ethoxy-9-hydroxy-delta-6a-tetrahydrocannabinol, 8,9-dihydroxy-delta-6a-tetrahydrocannabinol, cannabitriolvarin, ethoxy-cannabitriolvarin, dehydrocannabifuran, cannabifuran, cannabichromanon, cannabicitran, 10-oxo-delta-6a-tetrahydrocannabinol, delta-9-cis-tetrahydrocannabinol, 3, 4, 5, 6-tetrahydro-7-hydroxy-alpha-alpha-2-trimethyl-9-n-propyl-2, 6-methano-2H-1-benzoxocin-5-methanol-cannabiripsol,trihydroxy-delta-9-tetrahydrocannabinol, and cannabinol. Examples of cannabinoids within the context of this disclosure include tetrahydrocannabinol and cannabidiol. The term "cannabinoid" may also include different modified forms of a cannabinoid such as a hydroxylated cannabinoid or cannabinoid carboxylic acid. For example, if a UGT were to be capable of glycosylating a cannabinoid, it would include the term cannabinoid as defined elsewhere, as well as the aforementioned modified forms. It may further include multiple glycosylation moieties.

The term "endocannabinoid" refers to compounds including arachidonoyl ethanolamide (anandamide, AEA), 2-arachidonoyl ethanolamide (2-AG), 1-arachidonoyl ethanolamide (1-AG), and docosahexaenoyl ethanolamide (DHEA, synaptamide), oleoyl ethanolamide (OEA), cicsapentacnoyl ethanolamide, prostaglandin ethanolamide, docosahexaenoyl ethanolamide, linolenoyl cthanolamide, 5 (Z),8 (Z),1 1 (Z)-cicosatrienoic acid ethanolamide (mead acid ethanolamide), heptadecanoul ethanolamide, stearoyl ethanolamide, docosaenoyl ethanolamide, nervonoyl ethanolamide, tricosanoyl ethanolamide, lignoceroyl ethanolamide, myristoyl ethanolamide, pentadecanoyl ethanolamide, palmitoleoyl ethanolamide, docosahexaenoic acid (DHA). Particularly preferred endocannabinoids are AEA, 2-AG, 1-AG, and DHEA.

Hydroxylation is a chemical process that introduces a hydroxyl group (—OH) into an organic compound. Acetylation is a chemical reaction that adds an acetyl chemical group. Glycosylation is the coupling of a glycosyl donor, to a glycosyl acceptor forming a glycoside.

The term "prodrug" refers to a precursor of a biologically active pharmaceutical agent (drug). Prodrugs must undergo a chemical or a metabolic conversion to become a biologically active pharmaceutical agent. A prodrug can be converted ex vivo to the biologically active pharmaceutical agent by chemical transformative processes. In vivo, a prodrug is converted to the biologically active pharmaceutical agent by the action of a metabolic process, an enzymatic process or a degradative process that removes the prodrug moiety to form the biologically active pharmaceutical agent.

A polypeptide can be expressed in monocot plants and/or dicot plants. Techniques for introducing nucleic acids into plants are known in the art, and include, without limitation, *Agrobacterium*-mediated transformation, viral vector-mediated transformation, electroporation, and particle gun transformation (also referred to as biolistic transformation). See, for example, U.S. Pat. Nos. 5,538,880; 5,204,253; 6,329,571; and U.S. Pat. No. 6,013,863; Richards et al., Plant Cell. Rep. 20:48-20 54 (2001); Somleva et al., Crop Sci. 42:2080-2087 (2002); Sinagawa-Garcia et al., Plant Mol Biol (2009) 70:487-498; and Lutz et al., Plant Physiol., 2007, Vol. 145, pp. 1201-1210. In some instances, intergenic transformation of plastids can be used as a method of introducing a polynucleotide into a plant cell. In some instances, the method of introduction of a polynucleotide into a plant comprises chloroplast transformation. In some instances, the leaves and/or stems can be the target tissue of the introduced polynucleotide. If a cell or cultured tissue is used as the recipient tissue for transformation, plants can be regenerated from transformed cultures if desired, by techniques known to those skilled in the art.

Other suitable methods for introduce polynucleotides include electroporation of protoplasts, polyethylene glycol-mediated delivery of naked DNA into plant protoplasts, direct gene transformation through imbibition (e.g., introducing a polynucleotide to a dehydrated plant), transformation into protoplasts (which can comprise transferring a polynucleotide through osmotic or electric shocks), chemical transformation (which can comprise the use of a polybrene-spermidine composition), microinjection, pollen-tube pathway transformation (which can comprise delivery of a polynucleotide to the plant ovule), transformation via liposomes, shoot apex method of transformation (which can comprise introduction of a polynucleotide into the shoot and regeneration of the shoot), sonication-assisted *agrobacterium* transformation (SAAT) method of transformation, infiltration (which can comprise a floral dip, or injection by syringe into a particular part of the plant (e.g., leaf)), silicon-carbide mediated transformation (SCMT) (which can comprise the addition of silicon carbide fibers to plant tissue and the polynucleotide of interest), electroporation, and electrophoresis. Such expression may be from transient or stable transformations.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. (Thus, the term "homologous proteins" is defined to mean that the two proteins have similar amino acid sequences). More specifically, in certain embodiments, the term "homologous" with regard to a contiguous nucleic acid sequence, refers to contiguous nucleotide sequences that hybridize under appropriate conditions to the reference nucleic acid sequence. For example, homologous sequences may have from about 75%-100, or more generally 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target sequences under conditions where specific binding is desired, for example, under stringent hybridization conditions, and would fall within the range of a homolog. In another embodiment, expression optimization, for example for a mammalian lipocalin or odorant binding protein, to be expressed in yeast may be considered homologous and having a variable sequence identity due to the variable codon positions. Additional embodiments may also include homology to include redundant nucleotide codons.

The term "homolog", used with respect to an original enzyme or gene of a first family or species, refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

The term "operably linked," when used in reference to a regulatory sequence and a coding sequence, means that the regulatory sequence affects the expression of the linked coding sequence. "Regulatory sequences," or "control elements," refer to nucleotide sequences that influence the timing and level/amount of transcription, RNA processing or stability, or translation of the associated coding sequence. Regulatory sequences may include promoters; translation leader sequences; introns; enhancers; stem-loop structures; repressor binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule.

As used herein, the term "promoter" refers to a region of DNA that may be upstream from the start of transcription, and that may be involved in recognition and binding of RNA polymerase and other proteins to initiate transcription. A promoter may be operably linked to a coding sequence for expression in a cell, or a promoter may be operably linked to a nucleotide sequence encoding a signal sequence which may be operably linked to a coding sequence for expression in a cell. An "inducible" promoter may be a promoter which may be under environmental control. Tissue-specific, tissue-preferred, cell type specific, and inducible promoters constitute the class of "non-constitutive" promoters. A "constitutive" promoter is a promoter which may be active under most environmental conditions or in most cell or tissue types.

As used herein, the term "transformation" or "genetically modified" refers to the transfer of one or more nucleic acid molecule(s) into a cell. A plant is "transformed" or "genetically modified" by a nucleic acid molecule transduced into the plant when the nucleic acid molecule becomes stably replicated by the plant. As used herein, the term "transformation" or "genetically modified" encompasses all techniques by which a nucleic acid molecule can be introduced into, such as a plant.

The term "vector" refers to some means by which DNA, RNA, a protein, or polypeptide can be introduced into a host. The polynucleotides, protein, and polypeptide which are to be introduced into a host can be therapeutic or prophylactic in nature; can encode or be an antigen; or can be regulatory in nature, etc. There are various types of vectors including virus, plasmid, bacteriophages, cosmids, and bacteria. An "expression vector" is nucleic acid capable of replicating in a selected host cell or organism. An expression vector can replicate as an autonomous structure, or alternatively can integrate, in whole or in part, into the host cell chromosomes or the nucleic acids of an organelle, or it is used as a shuttle for delivering foreign DNA to cells, and thus replicate along with the host cell genome. Thus, an expression vector are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an "expression cassette." In contrast, as described in the examples herein, a "cassette" is a polynucleotide containing a section of an expression vector of this invention. The use of a cassette assists in the assembly of the expression vectors. An expression vector is a replicon, such as plasmid, phage, virus, chimeric virus, or cosmid, and which contains the desired polynucleotide sequence operably linked to the expression control sequence(s).

As is known in the art, different organisms preferentially utilize different codons for generating polypeptides. Such "codon usage" preferences may be used in the design of nucleic acid molecules encoding the proteins and chimeras of the invention in order to optimize expression in a particular host cell system. For example, all nucleotides of the present invention may be optimized for expression in a select organisms, such as a *Cannabis* plant, yeast, algae, fungi, and bacteria.

A polynucleotide sequence is operably linked to an expression control sequence(s) (e.g., a promoter and, optionally, an enhancer) when the expression control sequence controls and regulates the transcription and/or translation of that polynucleotide sequence.

Unless otherwise indicated, a particular nucleic acid sequence also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). Because of the degeneracy of nucleic acid codons, one can use various different polynucleotides to encode identical polypeptides. The Table below, contains information about which nucleic acid codons encode which amino acids.

Amino Acid Nucleic Acid Codons

| Amino Acid | Nucleic Acid Codons |
| --- | --- |
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |

Moreover, because the proteins are described herein, one can chemically synthesize a polynucleotide which encodes these polypeptides/chimeric proteins. Oligonucleotides and polynucleotides that are not commercially available can be chemically synthesized e.g., according to the solid phase phosphoramidite triester method first described by Beaucage and Caruthers, Tetrahedron Letts. 22:1859-1862 (1981), or using an automated synthesizer, as described in Van Devanter et al., Nucleic Acids Res. 12:6159-6168 (1984). Other methods for synthesizing oligonucleotides and polynucleotides are known in the art. Purification of oligonucleotides is by either native acrylamide gel electrophoresis or by anion-exchange HPLC as described in Pearson & Reanier, J. Chrom. 255:137-149 (1983).

The term "plant" or "plant system" includes whole plants, plant organs, progeny of whole plants or plant organs, embryos, somatic embryos, embryo-like structures, protocorms, protocorm-like bodies (PLBs), and culture and/or suspensions of plant cells. Plant organs comprise, e.g., shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like). The invention may also include Cannabaceae and other *Cannabis* strains, such as *C. sativa* generally.

The term "expression," as used herein, or "expression of a coding sequence" (for example, a gene or a transgene) refer to the process by which the coded information of a nucleic acid transcriptional unit (including, e.g., genomic DNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

The term "nucleic acid" or "nucleic acid molecules" include single- and double-stranded forms of DNA; single-stranded forms of RNA; and double-stranded forms of RNA (dsRNA). The term "nucleotide sequence" or "nucleic acid sequence" refers to both the sense and antisense strands of a nucleic acid as either individual single strands or in the duplex. The term "ribonucleic acid" (RNA) is inclusive of iRNA (inhibitory RNA), dsRNA (double stranded RNA), siRNA (small interfering RNA), mRNA (messenger RNA), miRNA (micro-RNA), hpRNA (hairpin RNA), lRNA (transfer RNA), whether charged or discharged with a corresponding acetylated amino acid), and cRNA (complementary RNA). The term "deoxyribonucleic acid" (DNA) is inclusive of cDNA, genomic DNA, and DNA-RNA hybrids. The terms "nucleic acid segment" and "nucleotide sequence segment," or more generally "segment," will be understood by those in the art as a functional term that includes both genomic sequences, ribosomal RNA sequences, transfer RNA sequences, messenger RNA sequences, operon sequences, and smaller engineered nucleotide sequences that encoded or may be adapted to encode, peptides, polypeptides, or proteins.

The term "gene" or "sequence" refers to a coding region operably joined to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (down-stream) the coding region (open reading frame, ORF) as well as, where applicable, intervening sequences (i.e., introns) between individual coding regions (i.e., exons). The term "structural gene" as used herein is intended to mean a DNA sequence that is transcribed into mRNA which is then translated into a sequence of amino acids characteristic of a specific polypeptide. It should be noted that any reference to a SEQ ID, or sequence specifically encompasses that sequence, as well as all corresponding sequences that correspond to that first sequence. For example, for any amino acid sequence identified, the specific specifically includes all compatible nucleotide (DNA and RNA) sequences that give rise to that amino acid sequence or protein, and vice versa.

A nucleic acid molecule may include either or both naturally occurring and modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hair-pinned, circular, and padlocked conformations.

The term "sequence identity" or "identity," as used herein in the context of two nucleic acid or polypeptide sequences, refers to the residues in the two sequences that are the same when aligned for maximum correspondence over a specified comparison window.

The terms "approximately" and "about" refer to a quantity, level, value, or amount that varies by as much as 30%, or in another embodiment by as much as 20%, and in a third embodiment by as much as 10% to a reference quantity, level, value or amount. As used herein, the singular form "a," "an," and "the" include plural references unless the context clearly dictates otherwise.

As used herein, "heterologous" or "exogenous" in reference to a nucleic acid is a nucleic acid that originates from a foreign species, or is synthetically designed, or, if from the same species, is substantially modified from its native form in composition and/or genomic locus by deliberate human intervention. A heterologous protein may originate from a foreign species or, if from the same species, is substantially modified from its original form by deliberate human intervention. By "host cell" is meant a cell which contains an introduced nucleic acid construct and supports the replication and/or expression of the construct.

EXAMPLES

Example 1: Identification of UGT Enzymes Having Activity Towards Cannabinoid Compounds The present inventors identified 171,569 UDP-UGTs from the literature and as characterized in publicly available databases. The sequences contained a total of 52,613 unique, characterized UDP-UGT sequences. Using proprietary filtering and unsupervised machine learning, it was established that these 52,613 sequences may be represented by 23,062 high potential representative sequences protecting groupings of 90% homology around each sequence. The large number of representative sequences is indicative of extreme diversity in sequence homology within the protein class. Due to this diversity, representative sequences were further grouped based on homology to known characterized structures of UDP-UGTs with a 30% sequence homology threshold to the structural template, a value well within field standards for structure homology. Structural homology of the enzymes appears to be much better conserved within the proteins than sequence homology. This allowed the present inventors to capture 9299 representative sequences in 40 structural groupings classified further into 3 larger structural groupings (Gram+Bacteria, GT-A, and GT-B). The representative sequence for each structural grouping was then docked in silico with both THC and CBD and ranked by strength of predicted interaction.

The present inventors have identified 9299 representatives (representing 90% homology to a larger number of sequences) UDP-UGTs predicted to have some action on cannabinoids including THC and CBD. These can be further represented in 40 structural groupings including primarily GT-A and GT-B fold enzymes but also including a few other unique structural groupings from gram positive bacteria that do not fit within GT-A/GT-B classification. While each sequence homology representative assigned to each structural group is expected to have some activity on cannabinoids based on known or computationally predicted activity of the structural representative, efficiency variation from sequence to sequence is expected and each sequence may be either more or less effective in glycosylation that the tested structural representative sequence. All predicted binding affinities presented here are representative of acceptably strong molecular interactions.

All 90% sequence homology representatives are provided as amino acid sequence in the appropriate structural grouping identified below. Structural groupings Identified by 4-digit RCSB PBD ID code representing best structural template with number of sequences in group:

GRAM+
- 1182 sequences_30/5tzk_sequences (SEQ ID NO. 1-1182)
- 40 sequences_30/3bcv_sequences (SEQ ID NO. 1183-1222)
- 583 sequences_30/5hea_sequences (SEQ ID NO. 1223-1805)
- 20 sequences_30/6h21_sequences (SEQ ID NO. 1806-1825)

GT-A
- 3 sequences_30/1g9r_sequences (SEQ ID NO. 1826-1828)
- 157 sequences_30/2z86_sequences (SEQ ID NO. 1829-1985)
- 468 sequences_30/3ckj_sequences (SEQ ID NO. 1986-2453)
- 673 sequences_30/3e25_sequences (SEQ ID NO. 2454-3126)
- 304 sequences_30/3fly_sequences (SEQ ID NO. 3127-3430)
- 51 sequences_30/4dec_sequences (SEQ ID NO. 3431-3481)
- 158 sequences_30/5mlz_sequences (SEQ ID NO. 3482-3639)
- 54 sequences_30/5nv4_sequences (SEQ ID NO. 3640-3693)
- 1006 sequences_30/6fsn_sequences (SEQ ID NO. 3694-4699)
- 560 sequences_30/6p61_sequences (SEQ ID NO. 4700-5259)

GT-B
- 1031 sequences_30/2acv_sequences (SEQ ID NO. 5260-6290)
- 663 sequences_30/2iya_sequences (SEQ ID NO. 6290-6953)
- 531 sequences_30/3hbf_sequences (SEQ ID NO. 6954-7484)
- 514 sequences_30/5g15_sequences (SEQ ID NO. 7485-7998)
- 245 sequences_30/3c48_sequences (SEQ ID NO. 7999-8243)
- 243 sequences_30/5nlm_sequences (SEQ ID NO. 8244-8486)
- 126 sequences_30/5du2_sequences (SEQ ID NO. 8487-8612)
- 76 sequences_30/2clx_sequences (SEQ ID NOs. 8613-8688)
- 70 sequences_30/5zfk_sequences (SEQ ID NOs. 8689-8758)
- 58 sequences_30/4rel_sequences (SEQ ID NOs. 8759-8816)
- 57 sequences_30/3otg_sequences (SEQ ID NOs. 8817-8873)
- 48 sequences_30/5v2j_sequences (SEQ ID NOs. 8874-8921)
- 44 sequences_30/2r60_sequences (SEQ ID NOs. 8922-8965)
- 42 sequences_30/4amg_sequences (SEQ ID NOs. 8966-9007)
- 39 sequences_30/4n9w_sequences (SEQ ID NOs. 9008-9046)
- 36 sequences_30/2pq6_sequences (SEQ ID NOs. 9047-9082)
- 29 sequences_30/4wyi_sequences (SEQ ID NOs. 9083-9111)
- 22 sequences_30/6bk0_sequences (SEQ ID NOs. 9112-9133)
- 16 sequences_30/6inf_sequences (SEQ ID NOs. 9134-9149)
- 9 sequences_30/3ia7_sequences (SEQ ID NOs. 9150-9158)
- 7 sequences_30/5d01_sequences (SEQ ID NOs. 9159-9165)
- 5 sequences_30/6ij9_sequences (SEQ ID NOs. 9166-9170)
- 5 sequences_30/6d9t_sequences (SEQ ID NOs. 9171-9175)
- 5 sequences_30/2jjm_sequences (SEQ ID NOs. 9176-9180)
- 1 sequences_30/3mbo_sequences (SEQ ID NO. 9181)

Example 2: Functional-Structural Grouping of UGT Enzymes

Figure 7:
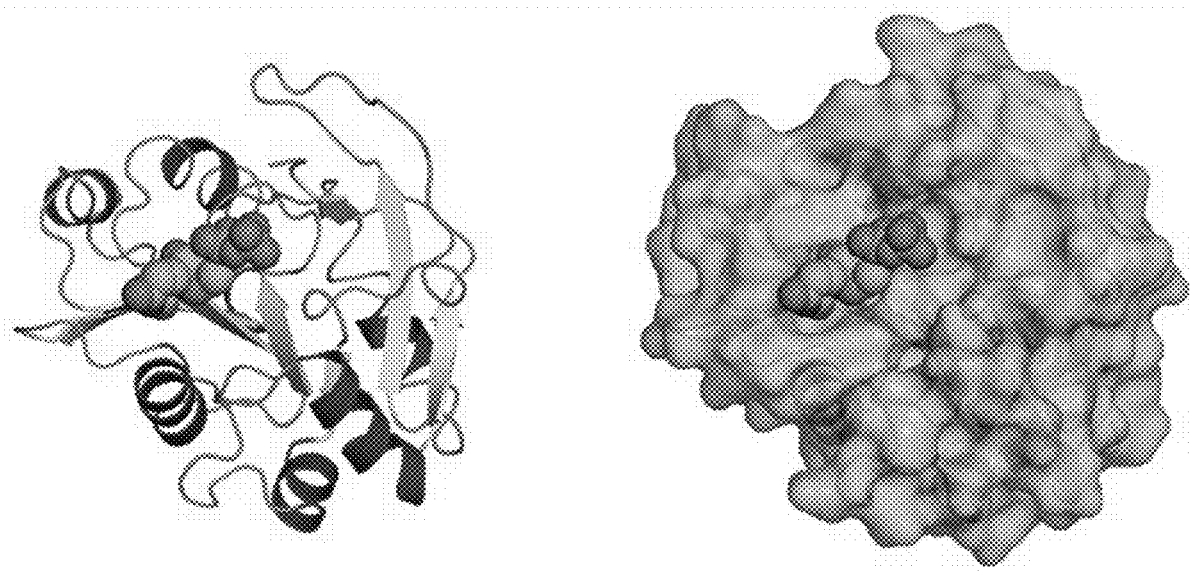
FIG. 7. Example of a GT adopting the GT-A fold (PDB ID 6P61). In the left panel, the enzyme is drawn as cartoons with the α-helices, β-sheet, and loops. Bound UDP is shown. In the right panel, the same protein view is shown but with the protein surface. The binding site for substrates is found on the surface pocket to the right of the UDP moiety.
Figure 8:
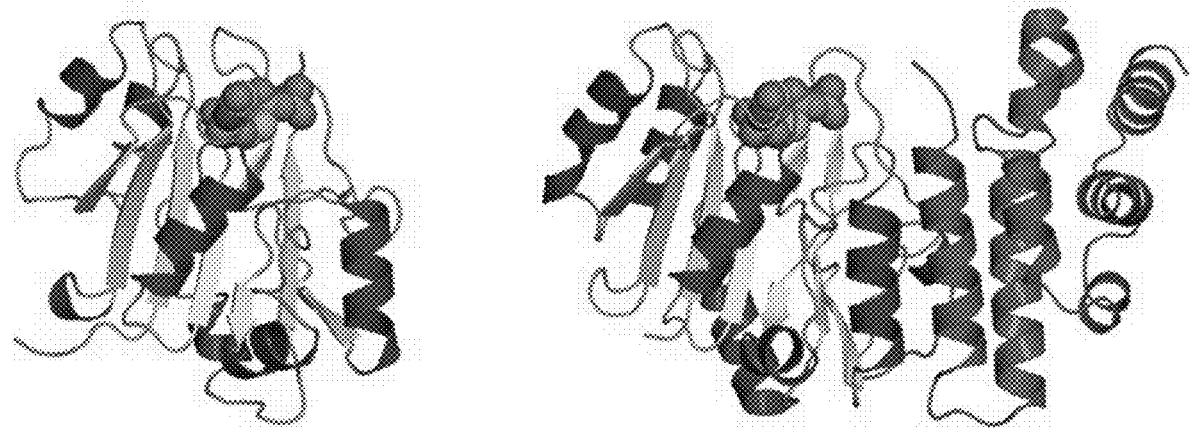
FIG. 8. Comparison of GT-A folds. The left panel shows the same enzyme (PDB ID 6P61) as in FIG. 1 but at a different orientation. The right panel shows another enzyme (PDB ID 5TZK; from *Staphylococcus aureus*) that has been structurally aligned with the protein on the left to highlight the similarity of their GT-A folds. The bacterial enzyme additionally contains an α-helical TPR motif that is involved in oligomerization.
Figure 9:
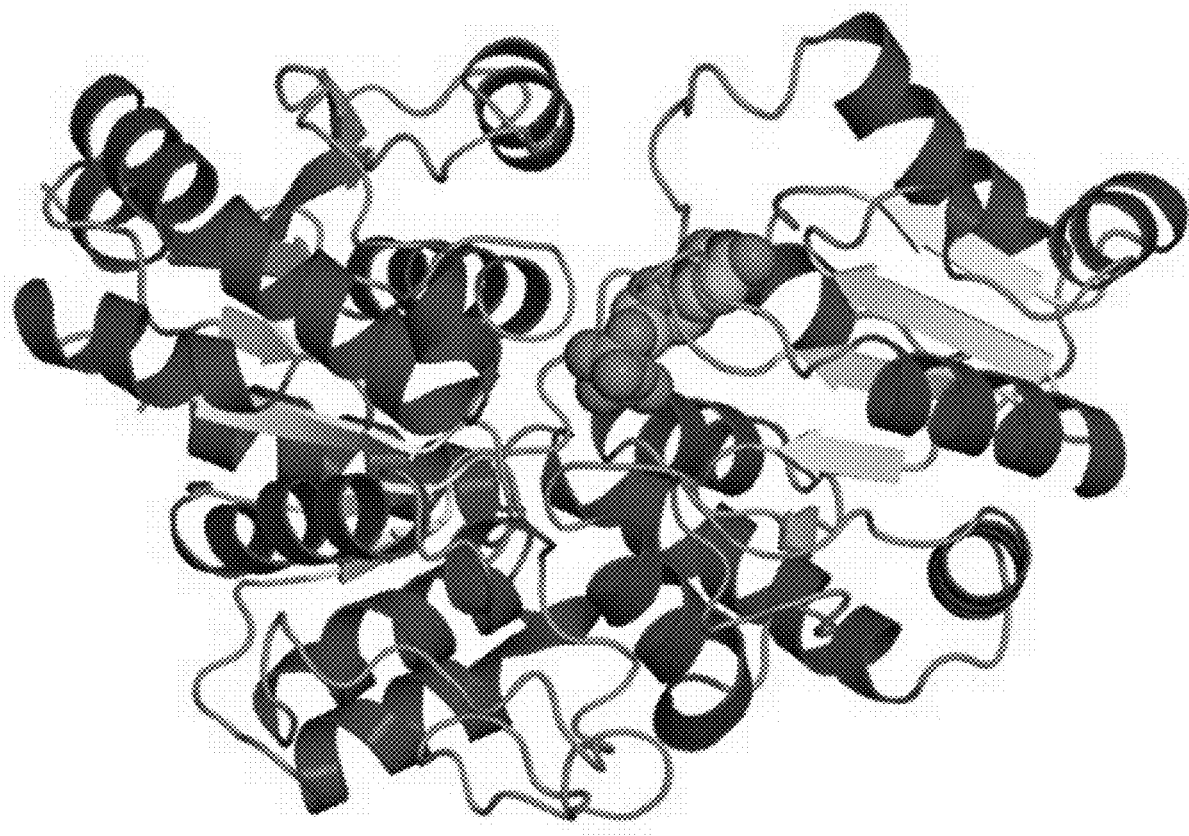
FIG. 9. Example of a GT adopting the GT-A fold (PDB ID 2ACV). The enzyme is drawn as cartoons with the α-helices, β-sheet, and loops colored red, yellow, and green, respectively. The N-terminal and C-terminal domains are on the left and right sides of the protein in this view. Bound UDP is shown in contact with the C-terminal domain. The binding site for substrates is found to the bottom-left of the UDP moiety, closer to the N-terminal domain.

The Carbohydrate-Active enZyme database (CAZy) currently groups UGTs (GTs) into 110 functional families comprising the so-called Leloir GTs (dependent on sugar nucleotides like UDP-glucose) and the non-Leloir GTs (non-sugar nucleotide-dependent). The Leloir GTs, which are the focus in this application, have been found to adopt one of two structural folds, termed the GT-A and GT-B folds. The GT-A fold consists of a single domain with a seven-stranded β-sheet flanked on both sides of the sheet by several a-helices (FIG. 7). Some bacterial GTs that adopt the GT-A fold also contain an additional tetratricopeptide repeat (TPR) motif that mediates the assembly of oligomers (FIG. 8). The GT-B fold consists of two distinct N-terminal and C-terminal domains that both adopt Rossmann-like folds (FIG. 9). The substrate is bound closer to the N-terminal domain while the sugar nucleotide is bound closer to the C-terminal domain. Of the 110 functional families listed in the CAZy database, 21 and 18 of these were respectively found to adopt the GT-B and GT-A folds.

TABLES

TABLE 1

UDP-UGT Structural Representative Cannabinoid Predicted Binding Affinity Tables:

| Structure | Affinity | Units |
|---|---|---|
| Gram+ Bacterial UDP-UGTs CBD Binding | | |
| 5tzk/min_ligand_CBD_01.pdbqt.log | −9.18445 | (kcal/mol) |
| 3bcv/min_ligand_CBD_01.pdbqt.log | −8.87895 | (kcal/mol) |
| 5hea/min_ligand_CBD_10.pdbqt.log | −8.58535 | (kcal/mol) |
| 6h21/min_ligand_CBD_10.pdbqt.log | −8.02499 | (kcal/mol) |
| Gram+ Bacterial UDP-UGTs THC Binding | | |
| 5tzk/min_ligand_THC_04.pdbqt.log | −10.76935 | (kcal/mol) |
| 5hea/min_ligand_THC_01.pdbqt.log | −9.44755 | (kcal/mol) |
| 6h21/min_ligand_THC_04.pdbqt.log | −8.46399 | (kcal/mol) |
| 3bcv/min_ligand_THC_01.pdbqt.log | −7.63992 | (kcal/mol) |

TABLE 1-continued

UDP-UGT Structural Representative Cannabinoid Predicted Binding Affinity Tables:

| Structure | Affinity | Units |
|---|---|---|
| GT-A UDP-UGTs CBD Binding | | |
| 6p61c1/min_ligand_CBD_04.pdbqt.log | −10.94076 | (kcal/mol) |
| 2z86c1/min_ligand_CBD_05.pdbqt.log | −10.7412 | (kcal/mol) |
| 5nv4/min_ligand_CBD_08.pdbqt.log | −10.473 | (kcal/mol) |
| 3fly/min_ligand_CBD_04.pdbqt.log | −10.18567 | (kcal/mol) |
| 3ckj/min_ligand_CBD_03.pdbqt.log | −8.43406 | (kcal/mol) |
| 6fsn/min_ligand_CBD_1.pdbqt.log | −7.49086 | (kcal/mol) |
| 1g9r/min_ligand_CBD_01.pdbqt.log | −7.3355 | (kcal/mol) |
| 3e25/min_ligand_CBD_03.pdbqt.log | −6.68012 | (kcal/mol) |
| 5mlz/min_ligand_CBD_2.pdbqt.log | −6.35057 | (kcal/mol) |
| 4dec/min_ligand_CBD_05.pdbqt.log | −4.73222 | (kcal/mol) |
| GT-A UDP-UGTs THC Binding | | |
| 2z86/min_ligand_THC_01.pdbqt.log | −10.78944 | (kcal/mol) |
| 3fly/min_ligand_THC_04.pdbqt.log | −10.65424 | (kcal/mol) |
| 6p61/min_ligand_THC_03.pdbqt.log | −10.64424 | (kcal/mol) |
| 5nv4/min_ligand_THC_10.pdbqt.log | −9.39469 | (kcal/mol) |
| 3ckj/min_ligand_THC_08.pdbqt.log | −8.40829 | (kcal/mol) |
| 6fsn/min_ligand_THC_2.pdbqt.log | −7.73952 | (kcal/mol) |
| 3e25/min_ligand_THC_10.pdbqt.log | −6.95711 | (kcal/mol) |
| 1g9r/min_ligand_THC_02.pdbqt.log | −6.65493 | (kcal/mol) |
| 4dec/min_ligand_THC_01.pdbqt.log | −6.05658 | (kcal/mol) |
| GT-B UDP-UGTs CBD Binding | | |
| 3otg/min_ligand_CBD_01.pdbqt.log | −15.46188 | (kcal/mol) |
| 3hbf/min_ligand_CBD_06.pdbqt.log | −11.14495 | (kcal/mol) |
| 5nlm/min_ligand_CBD_07.pdbqt.log | −9.32883 | (kcal/mol) |
| 2c1x/min_ligand_CBD_06.pdbqt.log | −8.6653 | (kcal/mol) |
| 6d9t/min_ligand_CBD_02.pdbqt.log | −8.23633 | (kcal/mol) |
| 5v2j/min_ligand_CBD_07.pdbqt.log | −8.21936 | (kcal/mol) |
| 4rel/min_ligand_CBD_05.pdbqt.log | −7.98206 | (kcal/mol) |
| 6inf/min_ligand_CBD_10.pdbqt.log | −7.9467 | (kcal/mol) |
| 5gl5/min_ligand_CBD_05.pdbqt.log | −7.8509 | (kcal/mol) |
| 6ij9/min_ligand_CBD_06.pdbqt.log | −7.61328 | (kcal/mol) |
| 2jjm/min_ligand_CBD_05.pdbqt.log | −7.52191 | (kcal/mol) |
| 5du2/min_ligand_CBD_04.pdbqt.log | −7.32558 | (kcal/mol) |
| 2pq6/min_ligand_CBD_05.pdbqt.log | −7.27422 | (kcal/mol) |
| 2iya/min_ligand_CBD_07.pdbqt.log | −6.92545 | (kcal/mol) |
| 3ia7/min_ligand_CBD_02.pdbqt.log | −6.76971 | (kcal/mol) |
| 4amg/min_ligand_CBD_09.pdbqt.log | −6.72897 | (kcal/mol) |
| 5d01/min_ligand_CBD_09.pdbqt.log | −6.55769 | (kcal/mol) |
| 3c48/min_ligand_CBD_3.pdbqt.log | −6.52731 | (kcal/mol) |
| 2r60/min_ligand_CBD_07.pdbqt.log | −6.43231 | (kcal/mol) |
| 4wyi/min_ligand_CBD_01.pdbqt.log | −6.3941 | (kcal/mol) |
| 6bk0/min_ligand_CBD_06.pdbqt.log | −6.0637 | (kcal/mol) |
| 3mbo/min_ligand_CBD_02.pdbqt.log | −5.92157 | (kcal/mol) |
| 2acv/min_ligand_CBD_02.pdbqt.log | −5.37595 | (kcal/mol) |
| 4n9w/min_ligand_CBD_09.pdbqt.log | −5.32776 | (kcal/mol) |
| 5zfk/min_ligand_CBD_10.pdbqt.log | −5.1177 | (kcal/mol) |
| GT-B UDP-UGTs THC Binding | | |
| 3otg/min_ligand_THC_4.pdbqt.log | −15.36588 | (kcal/mol) |
| 3hbf/min_ligand_THC_02.pdbqt.log | −10.84724 | (kcal/mol) |
| 5v2j/min_ligand_THC_08.pdbqt.log | −9.85188 | (kcal/mol) |
| 4amg/min_ligand_THC_02.pdbqt.log | −9.13889 | (kcal/mol) |
| 2c1x/min_ligand_THC_02.pdbqt.log | −8.50937 | (kcal/mol) |
| 2jjm/min_ligand_THC_09.pdbqt.log | −8.32614 | (kcal/mol) |
| 6d9t/min_ligand_THC_08.pdbqt.log | −8.12303 | (kcal/mol) |
| 4rel/min_ligand_THC_07.pdbqt.log | −7.83388 | (kcal/mol) |
| 2pq6/min_ligand_THC_01.pdbqt.log | −7.68854 | (kcal/mol) |
| 2r60/min_ligand_THC_01.pdbqt.log | −7.60612 | (kcal/mol) |
| 5nlm/min_ligand_THC_08.pdbqt.log | −7.58146 | (kcal/mol) |
| 6inf/min_ligand_THC_09.pdbqt.log | −7.08419 | (kcal/mol) |
| 5gl5/min_ligand_THC_01.pdbqt.log | −7.03571 | (kcal/mol) |
| 5d01/min_ligand_THC_5.pdbqt.log | −6.98384 | (kcal/mol) |
| 5du2/min_ligand_THC_01.pdbqt.log | −6.78902 | (kcal/mol) |
| 6ij9/min_ligand_THC_1.pdbqt.log | −6.60719 | (kcal/mol) |
| 2iya/min_ligand_THC_07.pdbqt.log | −6.36888 | (kcal/mol) |
| 2acv/min_ligand_THC_01.pdbqt.log | −6.26508 | (kcal/mol) |
| 6bk0/min_ligand_THC_04.pdbqt.log | −5.81022 | (kcal/mol) |
| 4wyi/min_ligand_THC_1.pdbqt.log | −5.72502 | (kcal/mol) |
| 3ia7/min_ligand_THC_02.pdbqt.log | −5.70649 | (kcal/mol) |
| 3c48/min_ligand_THC_3.pdbqt.log | −5.65728 | (kcal/mol) |
| 5zfk/min_ligand_THC_1.pdbqt.log | −5.63526 | (kcal/mol) |
| 3mbo/min_ligand_THC_02.pdbqt.log | −5.544 | (kcal/mol) |
| 4n9w/min_ligand_THC_02.pdbqt.log | −5.3822 | (kcal/mol) |

TABLE 2

Amino Acid sequences of cannabinoid-binding UDP-UGTs according to structural groupings

| | SEQ ID NO. |
|---|---|
| GRAM+ | |
| 5tzk | (SEQ ID NOs. 1-1182) |
| 3bcv | (SEQ ID NOs. 1183-1222) |
| 5hea | (SEQ ID NOs. 1223-1805) |
| 6h21 | (SEQ ID NOs. 1806-1825) |
| GT-A | |
| 1g9r | (SEQ ID NOs. 1826-1828) |
| 2z86 | (SEQ ID NOs. 1829-1985) |
| 3ckj | (SEQ ID NOs. 1986-2453) |
| 3e25 | (SEQ ID NOs. 2454-3126) |
| 3fly | (SEQ ID NOs. 3127-3430) |
| 4dec | (SEQ ID NOs. 3431-3481) |
| 5mlz | (SEQ ID NOs. 3482-3639) |
| 5nv4 | (SEQ ID NOs. 3640-3693) |
| 6fsn | (SEQ ID NOs. 3694-4699) |
| 6p61 | (SEQ ID NOs. 4700-5259) |
| GT-B | |
| 2acv | (SEQ ID NOs. 5260-6290) |
| 2iya | (SEQ ID NOs. 6290-6953) |
| 3hbf | (SEQ ID NOs. 6954-7484) |
| 5gl5 | (SEQ ID NOs. 7485-7998) |
| 3c48 | (SEQ ID NOs. 7999-8243) |
| 5nlm | (SEQ ID NOs. 8244-8486) |
| 5du2 | (SEQ ID NOs. 8487-8612) |
| 2c1x | (SEQ ID NOs. 8613-8688) |
| 5zfk | (SEQ ID NOs. 8689-8758) |
| 4rel | (SEQ ID NOs. 8759-8816) |
| 3otg | (SEQ ID NOs. 8817-8873) |
| 5v2j | (SEQ ID NOs. 8874-8921) |
| 2r60 | (SEQ ID NOs. 8922-8965) |
| 4amg | (SEQ ID NOs. 8966-9007) |
| 4n9w | (SEQ ID NOs. 9008-9046) |
| 2pq6 | (SEQ ID NOs. 9047-9082) |
| 4wyi | (SEQ ID NOs. 9083-9111) |
| 6bk0 | (SEQ ID NOs. 9112-9133) |
| 6inf | (SEQ ID NOs. 9112-9133) |
| 3ia7 | (SEQ ID NOs. 9150-9158) |
| 5d01 | (SEQ ID NOs. 9159-9165) |
| 6ij9 | (SEQ ID NOs. 9166-9170) |
| 6d9t | (SEQ ID NOs. 9171-9175) |
| 2jjm | (SEQ ID NOs. 9176-9180) |
| 3mbo | (SEQ ID NO. 9181) |

SEQUENCE LISTING

The patent contains a lengthy sequence listing. A copy of the sequence listing is available in electronic form from the USPTO web site (https://seqdata.uspto.gov/?pageRequest=docDetail&DocID=US12378586B2). An electronic copy of the sequence listing will also be available from the USPTO upon request and payment of the fee set forth in 37 CFR 1.19(b)(3).

What is claimed is:

1. A system for producing glycosylated cannabidiol (CBD) comprising:
    a yeast cell culture, where the yeast cells express a heterologous nucleotide sequence, operably linked to a promoter, encoding a UDP-glucosyltransferases (UGT) according to the amino acid sequence SEQ ID NO. 1, or a sequence having at least 95% sequence identity with SEQ ID NO. 1826; and
    wherein CBD is introduced to the culture where the UGT glycosylates said CBD generating a CBD glycoside.

2. The system of claim 1, wherein the yeast is *Picha pastoris*.

3. A system for producing glycosylated tetrahydrocannabinol (THC) comprising:
    a yeast cell culture, where the yeast cells express a heterologous nucleotide sequence, operably linked to a promoter, encoding a UDP-glucosyltransferases (UGT) according to the amino acid sequence SEQ ID NO. 1, or a sequence having at least 95% sequence identity with SEQ ID NO. 1826; and
    wherein THC is introduced to the culture where the UGT glycosylates said THC generating a CBD glycoside.

4. The system of claim 3, wherein the yeast is *Picha pastoris*.

* * * * *